United States Patent
Howard et al.

(10) Patent No.: US 7,741,319 B2
(45) Date of Patent: Jun. 22, 2010

(54) 11-HYDROXY-5H-PYRROLO[2,1-C][1,4]BENZODIAZEPIN-5-ONE DERIVATIVES AS KEY INTERMEDIATES FOR THE PREPARATION OF C2 SUBSTITUTED PYRROLOBENZODIAZEPINES

(75) Inventors: Philip Wilson Howard, St Albans (GB); Stephen John Gregson, London (GB)

(73) Assignee: Spirogen Limited, Ryde, Isle of Wight (GB)

( * ) Notice: Subject to any disclaimer, the term of this patent is extended or adjusted under 35 U.S.C. 154(b) by 372 days.

(21) Appl. No.: 10/598,518

(22) PCT Filed: Mar. 1, 2005

(86) PCT No.: PCT/GB2005/000768

§ 371 (c)(1), (2), (4) Date: Feb. 6, 2007

(87) PCT Pub. No.: WO2005/085251

PCT Pub. Date: Sep. 15, 2005

(65) Prior Publication Data

US 2007/0173497 A1 Jul. 26, 2007

(30) Foreign Application Priority Data

Mar. 1, 2004 (GB) .................................. 0404575.3
Dec. 1, 2004 (GB) .................................. 0426392.7

(51) Int. Cl.
C07D 487/04 (2006.01)
C07D 519/00 (2006.01)
A61K 31/5517 (2006.01)
A61P 35/00 (2006.01)

(52) U.S. Cl. ...................................... 514/220; 540/496
(58) Field of Classification Search ................. 540/496; 514/220
See application file for complete search history.

(56) References Cited

U.S. PATENT DOCUMENTS

| | | | |
|---|---|---|---|
| 3,523,941 A | 8/1970 | Leimgruber et al. |
| 3,524,849 A | 8/1970 | Batcho et al. |
| 4,185,016 A | 1/1980 | Takanabe et al. |
| 4,239,683 A | 12/1980 | Takanabe et al. |
| 4,309,437 A | 1/1982 | Ueda et al. |
| 5,418,241 A | 5/1995 | Jegham et al. |
| 6,562,806 B1 | 5/2003 | Thurston et al. |
| 6,608,192 B1 | 8/2003 | Thurston et al. |
| 6,660,856 B2 | 12/2003 | Wang |
| 6,747,144 B1 | 6/2004 | Thurston et al. |
| 6,909,006 B1 | 6/2005 | Thurston et al. |
| 7,049,311 B1 | 5/2006 | Thurston et al. |
| 7,067,511 B2 | 6/2006 | Thurston et al. |
| 7,265,105 B2 | 9/2007 | Thurston et al. |
| 7,407,951 B2 | 8/2008 | Thurston et al. |

(Continued)

FOREIGN PATENT DOCUMENTS

EP  1193270  4/2002

(Continued)

OTHER PUBLICATIONS

Adams et al., "Molecular modelling of a sequence-specific DNA-binding agent based on the pyrrolo[2,1-c][1,4]benzodiazepines," Pharm. Pharmacol. Commun. (1999) 5:555-560.

(Continued)

Primary Examiner—Bruck Kifle
(74) Attorney, Agent, or Firm—Michael Best & Friedrich LLP

(57) ABSTRACT

The present inventors have developed a key intermediate for the production of C2 substituted PBDs, which has a leaving group at the C2 position, a carbamate protecting group at the N10 position and a protected hydroxy group at the C11 position. In a first aspect, the present invention comprises a compound with a formula (I), wherein: $R^{10}$ is a carbamate-based nitrogen protecting group; $R^{11}$ is an oxygen protecting group; and $R^2$ is a labile leaving group. In a further aspect, the present invention comprises a method of synthesising a compound of formula (III), or a solvate thereof, from a compound of formula (I) as defined in the first aspect, $R^{16}$ is either O—R11, wherein $R^{11}$ is as defined in the first aspect, or OH, or $R^{10}$ and $R^{16}$ together form a double bond between N10 and C11; and $R^{15}$ is R. The other substituents are defined in the claims. Further aspects of the present invention relate to compounds of formula (III) (including solvates thereof when $R^{10}$ and $R^{16}$ form a double bond between N10 and C11, and pharmaceutical salts thereof), pharmaceutical compositions comprising these, and their use in the manufacture of a medicament for the treatment of a proliferative disease.

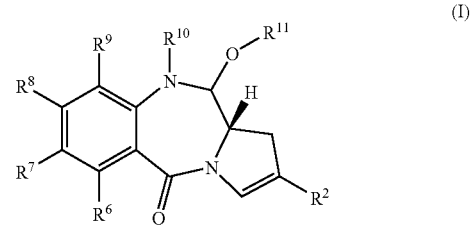

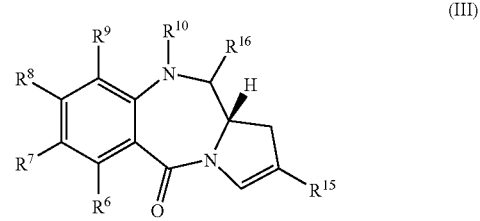

28 Claims, No Drawings

U.S. PATENT DOCUMENTS

| | | |
|---|---|---|
| 2003/0195196 A1 | 10/2003 | Thurston et al. |
| 2004/0092736 A1 | 5/2004 | Thurston et al. |
| 2004/0138269 A1 | 7/2004 | Sun et al. |
| 2004/0198722 A1 | 10/2004 | Thurston et al. |
| 2006/0264622 A1 | 11/2006 | Howard et al. |
| 2007/0185073 A1 | 8/2007 | Howard et al. |
| 2007/0191309 A1 | 8/2007 | Howard et al. |
| 2007/0191349 A1 | 8/2007 | Howard et al. |
| 2007/0249591 A1 | 10/2007 | Howard et al. |
| 2008/0090812 A1 | 4/2008 | Pepper et al. |
| 2008/0167293 A1 | 7/2008 | Howard et al. |
| 2008/0214525 A1 | 9/2008 | Howard et al. |

FOREIGN PATENT DOCUMENTS

| | | |
|---|---|---|
| FR | 2027356 | 12/1969 |
| FR | 2586683 | 3/1987 |
| GB | 1299198 | 12/1972 |
| JP | 53-82792 | 7/1978 |
| JP | 57131791 | 8/1982 |
| JP | 58180487 | 10/1983 |
| WO | WO 92/19620 | 11/1992 |
| WO | WO 93/18045 | 9/1993 |
| WO | 00/12506 | 3/2000 |
| WO | 00/12509 | 3/2000 |
| WO | WO 00/12507 | 3/2000 |
| WO | WO 00/12508 | 3/2000 |
| WO | WO 2004/043963 | 5/2004 |
| WO | WO 2005/023814 | 3/2005 |
| WO | 2005/042535 | 5/2005 |
| WO | WO 2005/040170 | 5/2005 |
| WO | WO 2005/085250 | 9/2005 |
| WO | WO 2005/085251 | 9/2005 |
| WO | WO 2005/085259 | 9/2005 |
| WO | WO 2005/085260 | 9/2005 |
| WO | 2005/110423 | 11/2005 |

OTHER PUBLICATIONS

Althius, T. H. and Hess, H. J., "Synthesis and Identification of the Major Metabolites of Prazosin Formed in Dog and Rat," *J. Medicinal Chem.* (1977) 20(1):146-148.

Arima et al., "Studies on Tomaymycin, a New Antibiotic. I. Isolation and Properties of Tomaymycin," *J. Antibiotics* (1972) 25:437-444.

Berge et al., "Pharmaceutical Salts," J. Pharm. Sci. (1977) 66:1-19.

Berry, J. M. et al., "Solid-phase synthesis of DNA-interactive pyrrolo[2,1-c][1,4]benzodiazepines," *Tetrahedron Letters* (2000) 41:6171-6174.

Bose et al., "New Approaches to Pyrrolo[2,1-c][1,4]benzodiazepines: Synthesis, DNA-binding and cytotoxicity of DC-81," *Tetrahedron*, 48, 751-758 (1992).

Bose, D.S. et al., "Rational Design of a Highly Efficient Irreversible DNA Interstrand Cross-Linking Agent Based on the Pyrrolobenzodiazepine Ring System," *J. Am. Chem. Soc.*, 114, 4939-4941 (1992).

Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.

Chen, Z. et al., "A novel approach to the synthesis of cytotoxic C2-C3 unsaturated pyrrolo[2,1-c][1,4]benzodiazepines (PBDs) with conjugated acrylyl C2-substituents," Biorg. Med. Chem. Lett. (2004) 14:1547-1549.

Cooper, N. et al., "Synthesis of novel PBDs as anti-tumour agents," Chem. Commun. (2002) 16:1764-1765.

Courtney, S. M. et al., "A new convenient procedure for the synthesis of pyrrolo[2,1-c][1,4]benzodiazepines", *Tetrahedron Letters*, vol. 34, No. 33, 5327-28 (1993).

Farmer, J.D. et al., "DNA binding properties of a new class of linked anthramycin analogs,", *Chemical Abstracts*, Abstract No. 239940r, vol. 114, No. 25, 899-903 (1991).

Foloppe, M.P. et al., "DNA-binding properties of pyrrolo[2,1-c][1,4]benzodiazephine N10-C11 amidines," *Eur. J. Med. Chem.*, 31, 407-410 (1996).

Fujisawa Pharmaceutical Co., Ltd., Abstract No. 139983k, " Benzodiazepine derivatives", *Chemical Abstracts*, vol. 99, No. 17, 603 (1983).

Fujisawa Pharmaceutical Co., Ltd., Abstract No. 72145x, "Benzodiazepine derivatives", *Chemical Abstracts*, vol. 98, No. 9, 638 (1983).

Fujisawa Pharmaceutical Co. Ltd., "Benzodiazepine derivatives," *SciFinder Scholar*, 2-3 (2002).

Fukuyama, T. et al., "Total Synthesis of (+)-Porothramycin B," *Tetrahedron Letters*, vol. 34, 16, 2577-2580 (1993).

Greene, T.W. and Wuts, P.G.M., *Protective Groups in Organic Synthesis*, John Wiley & Sons, 2nd ed., Ch 7, 315-345 (1991).

Gregson, S. et al., "Synthesis of a novel C2/C2'-exo unsaturated pyrrolobenzodiazepine cross-linking agent with remarkable DNA binding affinity and cytotoxicity," *Chemical Communications*, 797-798 (1999).

Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.

Gregson, S.J. et al., "Design, Synthesis and Evaluation of a Novel Pyrrolobenzodiazepine DNA-Interactive Agent with Highly Efficient Cross-Linking Ability and Potent Cytotoxicity", *J. Med. Chem.*, 44: 737-748 (2001).

Gregson, S.J. et al., "Effect of C2-*exo* Unsaturation on the Cytotoxicity and DNA-Binding Reactivity of Pyrrolo[2,1-c]1,4]benzodiazepines", *Bioorganic & Medicinal Chemistry Letters*, 10: 1845-1847 (2000).

Gregson, S.J. et al., "Linker length modulates DNA cross-linking reactivity and cytotoxic potency of C8/C8' ether-linked C2-exo-unsaturated pyrrolo[2,1-c][1,4]benzodiazepine (PBD) dimers," J. Med. Chem. (2004) 1161-1174.

Gregson, S.J. et al., "Synthesis of the first example of a C2-C3/C2'-C3'-endo unsaturated pyrrolo[2,1-c][1,4]benzodiazepine dimer," Biorg. Med. Chem. Lett. (2001) 11:2859-2862.

Gregson, S.J. et al., "Synthesis of the first examples of A-C8/C-C2 amide-linked pyrrolo[2,1-c][1,4]benzodiazepine dimers," Biorg. Med. Chem. Lett. (2003) 13:2277-2280.

Guiotto, A. et al., "Synthesis of novel C7-aryl substituted pyrrolo[2,1-c][1,4]benzodiazepines (PBDs) via Pro-N10-troc protection and suzuki coupling," *Bioorganic & Medicinal Chemistry Letters*, 8, No. 21, 3017-3018 (1998).

Hara et al., "DC 102, a new glycosidic pyrrolo(1,4)benzodiazepine antibiotic produced by *streptomyces* sp.", *J. Antibiotics*, 41, 702-704 (1988).

Hochlowski, J. et al., "Abbeymycin, a new anthramycin-type antibiotic produced by a streptomycete," *J. Antibiotics*, 40, 145-148 (1987).

Hurley, L. and Needham-Vandevanter, D., "Covalent Binding of Antitumor Antibiotics in the Minor Groove of DNA. Mechanism of Action of CC-1065 and the Pyrrolo(1,4)benzodiazepines," *Acc. Chem. Res.*, 19, 230-237 (1986).

Itoh et al., "Sibanomicin, a new pyrrolo(1,4)benzodiazepine antitumor antibiotic produced by a *micromonospora* sp." *J. Antibiotics*, 41, 1281-1284 (1988).

Kamal, A., et al., "An Efficient Synthesis of Pyrrolo[2,1-c][1,4] Benzodiazepine Antibiotics via Reductive Cyclization," *Bioorg. Med. Chem. Ltrs*, 7, No. 14, 1825-1828 (1997).

Kamal, A., et al., "Synthesis of Pyrrolo [2,1-c][1,4]-Benzodiazepene Antibiotics: Oxidation of Cyclic Secondary Amine with TPAP", *Tetrahedron*, v. 53, No. 9, 3223-3230 (1997).

Kamal et al., "Synthesis and DNA-binding affinity of A-C8/C-C2 alkoxyamido-linked pyrrolo[2,1-c][1,4]benzodiazepine dimers" Biorg. Med. Chem. Lett. (2003) 13(22):3955-3958.

Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.

Kaneko, T. et al., "Bicyclic and tricyclic analogues of anthramycin," J. Med. Chem. (1985) 28:388-392.

Kang, G.-D. et al., "Synthesis of a novel C2-aryl substituted 1,2-unsaturated pyrrolobenzodiazepine," Chem. Commun. (2003) 1688-1689.

Kohn, K., "Anthramycin," *Antibiotics III*, Springer-Verlag, NY, 3-11 (1975).

Konishi, M. et al., "Chicamycin, a new antitumor antibiotic II. Structure determination of chicamycins A and B," *J. Antibiotics*, 37, 200-206 (1984).

Kunimoto et al., "Mazethramycin, a new member of anthramycin group antibiotics," *J. Antibiotics*, 33, 665-667 (1980).

Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," *J. Org. Chem.*, 52, 91-97 (1987).

Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.

Leber, J.D. et al., "A revised structure for sibiromycin," *J. Am. Chem. Soc.*, 110, 2992-2993 (1988).

Leimgruber, W. et al., "Isolation and characterization of anthramycin, a new antitumor antibiotic," *J. Am. Chem. Soc.*, 87, 5791-5793 (1965).

Leimgruber, W. et al., "The structure of anthramycin," *J. Am. Chem. Soc.*, 87, 5793-5795 (1965).

Leimgruber, W. et al., "Total synthesis of anthramycin," *J. Am. Chem. Soc.*, 90, 5641-5643 (1968).

Lown et al., "Molecular Mechanism of Binding of Pyrrolo(1,4)benzodiazepine antitumour agents to deoxyribonucleic acid—anthramycin and tomaymycin," Biochem. Pharmacol. (1979), 28 (13), 2017-2026.

Mori, M. et al., "Total syntheses of prothracarcin and tomaymycin by use of palladium catalyzed carbonylation," Tetrahedron (1986) 42(14):3793-3806.

Mountzouris, J.A. et al., "Comparison of a DSB-120 DNA interstrand cross-linked adduct with the corresponding bis-Tomamycin adduct," J. Med. Chem. (1994) 37:3132-3140.

Nagasaka, T. and Koseki, Y, "Stereoselective Synthesis of Tilivalline," *Journal of Organic Chemistry*, vol. 63, No. 20, 6797-6801 (1998).

Nagasaka, T. et al., "Stereoselective Synthesis of Tilivalline," *Tetrahedron Letters*, 30:14, 1871-1872 (1989).

O'Neil, I.A., et al., "The Synthesis of Functionalized Pyrrolo-[2,1-c][1,4]-Benzodiazepines," *Synlett*, 75-78 (1997).

O'Neil, Chemical Abstract No. 171573p, "The synthesis of Functionalized Pyrrolo-[2,1-c][1,4]-Benzodiazepines", *Chemical Abstracts*, vol. 126, No. 13, 618 (1997).

O'Neil, I.A. et al., "DPPE: A Convenient Replacement for Triphenylphosphine in the Staudinger and Mitsunobu Reactions", *Tetrahedron Letters*, vol. 39, No. 42, 7787-7790 (1998).

Sagnou, M.J. et al., "Design and Synthesis of Novel Pyrrolobenzodiazepine (PDB) Prodrugs for ADEPT and GDEPT," *Bioorganic & Medicinal Chemistry Letters*, 10, 2083-2086 (2000).

Shimizu, K et al., "Prothracarcin, a Novel Antitumor Antibiotic," *J. Antibiotics*, 35, 972-978 (1982).

Smellie, M. et al., "Cellular pharmacology of novel C8-linked anthramycin-based sequence-selective DNA minor groove cross-linking agents," Br. J. Cancer (1994) 70:48-53.

Smellie, M. et al., "Sequence selective recognition of duplex DNA through covalent interstrand cross-linking," Biochem. (2003) 42:8232-8239.

Suggs, J.W. et al., "Synthesis and structure of anthramycin analogs via hydride reduction of dilactams," *Tetrahedron Letters*, 26, No. 40, 4871-4874 (1985).

Takeuchi, T. et al., "Neothramycins A and B, New Antitumor Antibiotics," *J. Antibiotics*, 29, 93-96 (1976).

Tercel, M. et al., "Unsymmetrical DNA cross-linking agents: combination of the CBI and PBD pharmacophores," J. Med. Chem. (2003) 46:2132-2151.

Thurston, D.E. and Thompson, A.S., "The molecular recognition of DNA," *Chem. Brit.*, 26, 767-772 (1990).

Thurston, D.E. and Bose, D.S., "Synthesis of DNA-Interactive Pyrrolo[2,1-c][1,4]benzodiazepines," *Chem. Rev.*, 94:433-465 (1994).

Thurston, D. E., "Advances in the study of Pyrrolo[2,1-c][1,4] benzodiazepine (PBD) Antitumour Antibiotics", *Molecular Aspects of Anticancer Drug-DNA Interaction*, Neidle, S. and Waring, M.J., Eds.; Macmillan Press Ltd, 1:54-88 (1993).

Thurston, D.E. et al., "Effect of A-ring modifications on the DNA-binding behavior and cytotoxicity of pyrrolo[2,1-c][1,4]benzodiazepines", *Journal of Medicinal Chemistry*, 42:1951-1964 (1999).

Thurston, D.E. et al., "Synthesis of Sequence-selective C8-linked Pyrrolo [2,1-c][1,4] Benzodiazepine DNA Interstrand Cross-linking Agent," *J. Org. Chem.*, 61:8141-8147 (1996).

Thurston, D.E. et al., "Synthesis of a novel GC-specific covalent-binding DNA affinity-cleavage agent based on pyrrolobenzodiazepines (PBDs)," Chemical Communications, 563-565 (1996).

Thurston, D.E., "Nucleic acid targeting: therapeutic strategies for the 21st century," Brit. J. Cancer (1999) 80(1):65-85.

Tiberghien, A.C. et al., "Application of the stille coupling reaction to the synthesis of C2-substituted endo-exo unsaturated pyrrolo[2,1-c][1,4]benzodiazepines (PBDs)," Biorg. Med. Chem. Lett. (2004) 14:5041-5044.

Tsunakawa, M. et al., "Porothramycin, a new antibiotic of the anthramycin group: Production, isolation, structure and biological activity," *J. Antibiotics*, 41:1366-1373 (1988).

Umezawa, H. et al., Chemical Abstract No. 4427a, "Mazethramycins" *Chemical Abstracts*, vol. 90, No. 1, 428 (1979).

Umezawa, H. et al., "Mazethramycins," *SciFinder Scholar*, 2-3 (2002).

Wilson, S.C. et al., "Design and Synthesis of a Novel Epoxide-Containing Pyrrolo[2,1-c][1,4]benzodiazepine (PBD) via a New Cyclization Procedure," *Tetrahedron Letters*, 36, No. 35, 6333-6336 (1995).

Wilson, S.C. et al., "Design, Synthesis, and Evaluation of a Novel Sequence-Selective Epoxide-Containing DNA Cross-Linking Agent Based on the Pyrrolo[2,1-c][1,4]benzodiazepine System", *J. Med. Chem.* 42:4028-4041 (1999).

United States Office Action for U.S. Appl. No. 09/763,813 dated Sep. 10, 2002 (11 pages).

United States Office Action for U.S. Appl. No. 09/763,813 dated Feb. 28, 2003 (8 pages).

United States Office Action for U.S. Appl. No. 09/763,813 dated May 21, 2003 (7 pages).

United States Office Action for U.S. Appl. No. 09/763,767 dated May 23, 2002 (20 pages).

United States Office Action for U.S. Appl. No. 09/763,767 dated Nov. 15, 2002 (19 pages).

United States Office Action for U.S. Appl. No. 09/763,767 dated May 20, 2003 (11 pages).

United States Office Action for U.S. Appl. No. 09/763,767 dated Jan. 14, 2004 (11 pages).

United States Office Action for U.S. Appl. No. 09/763,767 dated Aug. 4, 2004 (7 pages).

United States Office Action for U.S. Appl. No. 09/763,767 dated Jun. 9, 2005 (5 pages).

United States Office Action for U.S. Appl. No. 11/367,241 dated Jun. 22, 2006 (11 pages).

United States Office Action for U.S. Appl. No. 11/367,241 dated Nov. 24, 2006 (16 pages).

United States Office Action for U.S. Appl. No. 09/763,814 dated Sep. 13, 2001 (16 pages).

United States Office Action for U.S. Appl. No. 09/763,814 dated Apr. 23, 2002 (23 pages).

United States Office Action for U.S. Appl. No. 09/763,814 dated Jul. 24, 2002 (8 pages).

United States Office Action for U.S. Appl. No. 09/763,814 dated Sep. 23, 2002 (8 pages).

United States Office Action for U.S. Appl. No. 09/673,768 dated Dec. 14, 2001 (7 pages).

United States Office Action for U.S. Appl. No. 09/673,768 dated Jul. 12, 2002 (4 pages).

United States Office Action for U.S. Appl. No. 09/673,768 dated Dec. 24, 2002 (4 pages).
United States Office Action for U.S. Appl. No. 10/021,213 dated May 20, 2003 (10 pages).
United States Office Action for U.S. Appl. No. 10/379,049 dated Mar. 21, 2005 (14 pages).
United States Office Action for U.S. Appl. No. 10/379,049 dated Oct. 5, 2005 (17 pages).
United States Office Action for U.S. Appl. No. 10/379,049 dated Apr. 26, 2006 (9 pages).
United States Office Action for U.S. Appl. No. 10/602,521 dated Sep. 24, 2007 (12 pages).
United States Office Action for U.S. Appl. No. 10/602,521 dated Mar. 26, 2008 (8 pages).
United States Office Action for U.S. Appl. No. 10/602,521 dated May 31, 2008 (8 pages).
United States Office Action for U.S. Appl. No. 10/602,521 dated Jul. 15, 2008 (7 pages).
United States Office Action for U.S. Appl. No. 10/602,521 dated Dec. 10, 2008 (12 pages).
United States Office Action for U.S. Appl. No. 10/824,743 dated Jul. 31, 2006 (6 pages).
United States Office Action for U.S. Appl. No. 10/824,743 dated Jan. 17, 2007 (15 pages).
United States Office Action for U.S. Appl. No. 10/824,743 dated Oct. 9, 2007 (12 pages).
United States Office Action for U.S. Appl. No. 10/534,825 dated Sep. 7, 2006 (7 pages).
United States Office Action for U.S. Appl. No. 10/534,825 dated Mar. 2, 2007 (7 pages).
United States Office Action for U.S. Appl. No. 10/534,825 dated Sep. 20, 2007 (4 pages).
United States Office Action for U.S. Appl. No. 10/571,274 dated Oct. 31, 2007 (6 pages).
United States Office Action for U.S. Appl. No. 10/598,470 dated May 23, 2008 (6 pages).
United States Office Action for U.S. Appl. No. 10/598,482 dated May 22, 2008 (9 pages).
United States Office Action for U.S. Appl. No. 10/598,482 dated Nov. 24, 2008 (6 pages).
United States Office Action for U.S. Appl. No. 10/598,691 dated Mar. 21, 2008 (7 pages).
United States Office Action for U.S. Appl. No. 10/598,691 dated Sep. 29, 2008 (6 pages).
United States Office Action for U.S. Appl. No. 11/569,007 dated Oct. 15, 2008 (12 pages).
Farmer, J.D. et al., "Synthesis and CNA crosslinking ability of a dimeric anthramycin analog," Tetrahedron Letters (1988) 29(40):5105-5108 Abstract only.
Kamal, A. et al., "Design, synthesis and evaluation of new noncrosslinking pyrrolobenzodiazepine dimers with efficient DNA binding ability and potent antitumor activity," J. Med. Chem. (2002) 45:4679-4688.
Weidner-Wells, M.A. et al., "Photochemical approach to the synthesis of the pyrrolo[1,4]benzodiazepine antibiotics," J. Org. Chem. (1989) 54:5746-5758.
Dupont, C. et al., "Synthesis of rhazinilam analogue acting as an inhibitor of tubulin assembly," Tetrahedron Lett. (2000) 41:5853-5856.
Wolff, M.E., Burger's Medicinal Chemistry, 4th Edition, Part I, Wiley: New York (1979) 336-337.
United States Office Action for U.S. Appl. No. 11/569,007 dated Jun. 1, 2009 (10 pages).
United States Office Action for U.S. Appl. No. 10/591,140 dated Jul. 6, 2009 (16 pages).
United States Patent Office Action for U.S. Appl. No. 10/602,521 dated Sep. 9, 2009 (14 pages).

11-HYDROXY-5H-PYRROLO[2,1-C][1,4] BENZODIAZEPIN-5-ONE DERIVATIVES AS KEY INTERMEDIATES FOR THE PREPARATION OF C2 SUBSTITUTED PYRROLOBENZODIAZEPINES

CROSS-REFERENCE TO RELATED APPLICATIONS

This patent application is a national stage filing under 35 U.S.C. 371 of International Application No. PCT/GB2005/000768, filed on Mar. 1, 2005, which claims foreign priority benefits to United Kingdom Application No. 0404575.3, filed Mar. 1, 2004 and United Kingdom Application No. 0426392.7, filed Dec. 1, 2004.

The present invention relates to pyrrolobenzodiazepines (PBDs), and in particular pyrrolobenzodiazepines useful in the synthesis of C2 substituted compounds.

BACKGROUND TO THE INVENTION

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.,* 87, 5793-5795 (1965); Leimgruber, et al., *J. Am. Chem. Soc.,* 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994)). Family members include abbeymycin (Hochlowski, et al., *J. Antibiotics,* 40, 145-148 (1987)), chicamycin (Konishi, et al., *J. Antibiotics,* 37, 200-206 (1984)), DC-81 (Japanese Patent 58-180 487; Thurston, et al., *Chem. Brit.,* 26, 767-772 (1990); Bose, et al., *Tetrahedron,* 48, 751-758 (1992)), mazethramycin (Kuminoto, et al., *J. Antibiotics,* 33, 665-667 (1980)), neothramycins A and B (Takeuchi, et al., *J. Antibiotics,* 29, 93-96 (1976)), porothramycin (Tsunakawa, et al., *J. Antibiotics,* 41, 1366-1373 (1988)), prothracarcin (Shimizu, et al, *J. Antibiotics,* 29, 2492-2503 (1982); Langley and Thurston, *J. Org. Chem.,* 52, 91-97 (1987)), sibanomicin (DC-102)(Hara, et al., *J. Antibiotics,* 41, 702-704 (1988); Itoh, et al., *J. Antibiotics,* 41, 1281-1284 (1988)), sibiromycin (Leber, et al., *J. Am. Chem. Soc.,* 110, 2992-2993 (1988)) and tomamycin (Arima, et al., *J. Antibiotics,* 25, 437-444 (1972)). PBDs are of the general structure:

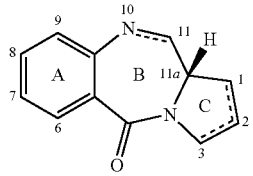

They differ in the number, type and position of substituents, in both their aromatic A rings and pyrrolo C rings, and in the degree of saturation of the C ring. In the B-ring there is either an imine(N═C), a carbinolamine(NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics* III. Springer-Verlag, New York, pp. 3-11 (1975); Hurley and Needham-VanDevanter, *Acc. Chem. Res.,* 19, 230-237 (1986)). Their ability to form an adduct in the minor groove, enables them to interfere with DNA processing, hence their use as antitumour agents.

The present inventors have previously disclosed, in PCT/GB2003/004963, cytotoxic compounds having an aryl group at the C2 position, for example:

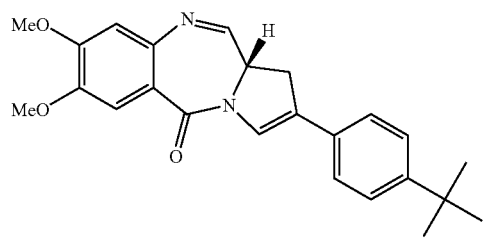

The synthesis of these compounds was achieved via the following intermediate:

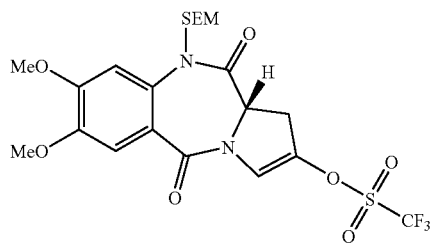

whose synthesis was described in detail in WO 00/12508. This method involves a reduction as a deprotection step, which can lead to overreduction of the compound which is not desirable. Also, with certain C2 groups, the reduction step does not proceed at all.

The following intermediate has also been disclosed:

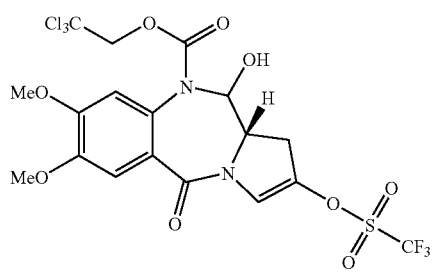

but its synthesis has proved difficult and only proceeds in low yield.

DISCLOSURE OF THE INVENTION

The present inventors have developed a key intermediate for the production of C2 substituted PBDs, which has a leaving group at the C2 position, a carbamate protecting group at the N10 position and a protected hydroxy group at the C11 position.

In a first aspect, the present invention comprises a compound with the formula I:

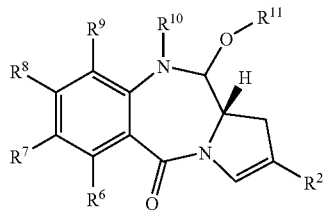

wherein:
$R^6$ and $R^9$ are independently selected from H, R, OH, OR, SH, SR, $NH_2$, NHR, NRR', nitro, $Me_3Sn$ and halo;
where R and R' are independently selected from optionally substituted $C_{1-12}$ alkyl, $C_{3-20}$ heterocyclyl and $C_{5-20}$ aryl groups;
$R^7$ and $R^8$ are independently selected from H, R, OH, OR, SH, SR, $NH_2$, NHR, NHRR', nitro, $Me_3Sn$ and halo, or the compound is a dimer with each monomer being of formula (I), where the $R^7$ groups or $R^8$ groups of each monomers form together a dimer bridge having the formula —X—R"—X— linking the monomers, where R" is a $C_{3-12}$ alkylene group, which chain may be interrupted by one or more heteroatoms, e.g. O, S, NH, and/or aromatic rings, e.g. benzene or pyridine, and each X is independently selected from O, S, or NH;
or any pair of adjacent groups from $R^6$ to $R^9$ together form a group —O—$(CH_2)_p$—O—, where p is 1 or 2;
$R^{10}$ is a carbamate-based nitrogen protecting group;
$R^{11}$ is an oxygen protecting group; and
$R^2$ is a labile leaving group.

In a second aspect, the present invention comprises a method of synthesising a compound of formula I as defined in the first aspect of the invention from a compound of formula IIa:

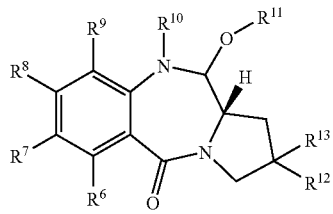

wherein $R^6$, $R^7$, $R^8$, $R^9$, $R^{10}$ and $R^{11}$ are as defined in the first aspect; and
$R^{12}$ and $R^{13}$ together form =O.

It is preferred that the compound of formula IIa is synthesised from a compound of formula IIb:

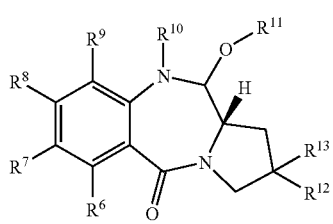

wherein $R^6$, $R^7$, $R^8$, $R^9$, $R^{10}$ and $R^{11}$ are as defined in the first aspect;
$R^{12}$ is O—$R^{14}$, and $R^{13}$ is H, where $R^{14}$ is an oxygen protecting group which is orthogonal to $R^{11}$.

In a third aspect, the present invention comprises a method of synthesising a compound of formula III:

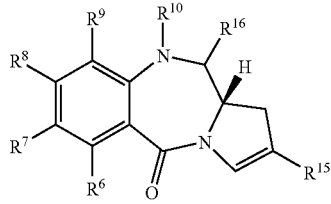

or a solvate thereof, from a compound of formula I as defined in the first aspect, wherein $R^6$, $R^7$, $R^8$, $R^9$ are as defined in the first aspect;
$R^{10}$ is as defined in the first aspect and $R^{16}$ is either O—$R^{11}$, wherein $R^{11}$ is as defined in the first aspect, or OH, or $R^{10}$ and $R^{16}$ together form a double bond between N10 and C11; and
$R^{15}$ is R.

Further aspects of the present invention relate to novel compounds of formula III (including solvates thereof when $R^{10}$ and $R^{16}$ form a double bond between N10 and C11, and pharmaceutical salts thereof), their use in methods of therapy (particularly in treating proliferative diseases), pharmaceutical compositions comprising these, and their use in the manufacture of a medicament for the treatment of a proliferative disease.

DEFINITIONS

Carbamate-Based Nitrogen Protecting Groups

Carbamate-based nitrogen protecting groups are well known in the art, and have the following structure:

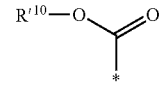

wherein $R'^{10}$ is R as defined above. A large number of suitable groups are described on pages 503 to 549 of Greene, T. W. and Wuts, G. M., Protective Groups in Organic Synthesis, 3$^{rd}$ Edition, John Wiley & Sons, Inc., 1999, which is incorporated herein by reference.

Particularly preferred protecting groups include Troc, Teoc, Fmoc, BOC, Doc, Hoc, TcBOC, 1-Adoc and 2-Adoc.

Those protecting groups which can be removed with palladium catalysis are not preferred, e.g. Alloc.

Also suitable for use in the present invention are nitrogen protecting group which can be removed in vivo (e.g. enzymatically, using light) as described in WO 00/12507, which is incorporated herein by reference. Examples of these protecting groups include:

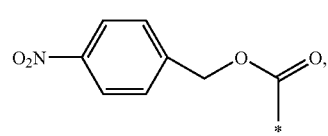

which is nitroreductase labile (e.g. using ADEPT/GDEPT);

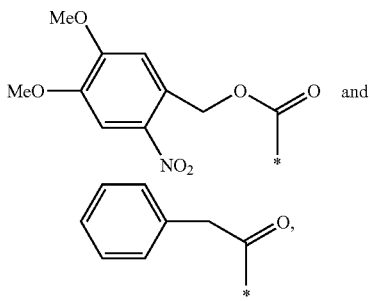

and which are photolabile; and

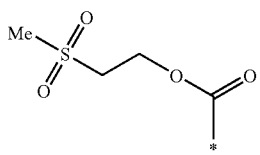

which is glutathione labile (e.g. using NPEPT).

Oxygen Protecting Groups

Oxygen protecting groups are well known in the art. A large number of suitable groups are described on pages 23 to 200 of Greene, T. W. and Wuts, G. M., Protective Groups in Organic Synthesis, 3$^{rd}$ Edition, John Wiley & Sons, Inc., 1999, which is incorporated herein by reference.

Classes of particular interest include silyl ethers, methyl ethers, alkyl ethers, benzyl ethers, esters, benzoates, carbonates, and sulfonates.

Preferred oxygen protecting groups include TBS, THP for the C11 oxygen atom, and methyl ester for the C2 oxygen atom (where present).

As mentioned above the oxygen protecting group $R^{14}$ should be orthogonal to the oxygen protecting group $R^{11}$. Protecting groups which are orthogonal to one another may each be removed using reagents or conditions which do not remove the other protecting group.

It may also be preferred that any protecting groups used during the synthesis and use of compounds of formula I are orthogonal to one another. However, it is often not necessary, but may be desirable, for the carbamate-based nitrogen protecting group and $R^{11}$ to be orthogonal to one another, depending on whether the compound of formula III is to be used with the nitrogen protecting group in place.

Labile Leaving Groups

Labile leaving groups suitable for use in the present invention are in particular those amenable to palladium catalysed coupling, for example using Suzuki or Stille coupling. Suitable groups include mesylate(—OSO$_2$CH$_3$), —OSO$_2$(C$_n$F$_{2n+1}$) where n=0, 1 or 4, —OSO$_2$—R$^S$ where R$^S$ is an optionally substituted phenyl group (e.g. 4-Me-Ph, tosylate), I, Br and Cl. More preferred are —OSO$_2$(C$_n$F$_{2n+1}$) where n=0, 1 or 4, I, Br and Cl, with triflate (—OSO$_2$CF$_3$) and Br being the most preferred.

Substituents

The phrase "optionally substituted" as used herein, pertains to a parent group which may be unsubstituted or which may be substituted.

Unless otherwise specified, the term "substituted" as used herein, pertains to a parent group which bears one or more substitutents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl($C_1$), ethyl($C_2$), propyl($C_3$), butyl($C_4$), pentyl($C_5$), hexyl($C_6$) and heptyl($C_7$).

Examples of saturated linear alkyl groups include, but are not limited to, methyl($C_1$), ethyl($C_2$), n-propyl($C_3$), n-butyl($C_4$), n-pentyl(amyl)($C_5$), n-hexyl($C_6$) and n-heptyl($C_7$).

Examples of saturated branched alkyl groups include iso-propyl($C_3$), iso-butyl($C_4$), sec-butyl($C_4$), tert-butyl($C_4$), iso-pentyl($C_5$), and neo-pentyl($C_5$).

$C_{2-12}$ Alkenyl: The term "$C_{2-12}$ alkenyl" as used herein, pertains to an alkyl group having one or more carbon-carbon double bonds.

Examples of unsaturated alkenyl groups include, but are not limited to, ethenyl(vinyl, —CH═CH$_2$), 1-propenyl(—CH═CH—CH$_3$), 2-propenyl(allyl, —CH—CH═CH$_2$), isopropenyl(1-methylvinyl, —C(CH$_3$)═CH$_2$), butenyl($C_4$), pentenyl($C_5$), and hexenyl($C_6$).

$C_{2-12}$ alkynyl: The term "$C_{2-12}$ alkynyl" as used herein, pertains to an alkyl group having one or more carbon-carbon triple bonds.

Examples of unsaturated alkynyl groups include, but are not limited to, ethynyl(ethinyl, —C≡CH) and 2-propynyl (propargyl, —CH$_2$—C≡CH).

$C_{3-12}$ cycloalkyl: The term "$C_{3-12}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:

saturated monocyclic hydrocarbon compounds: cyclopropane($C_3$), cyclobutane($C_4$), cyclopentane($C_5$), cyclohexane($C_6$), cycloheptane($C_7$), methylcyclopropane($C_4$), dimethylcyclopropane($C_5$), methylcyclobutane($C_5$), dimethylcyclobutane($C_6$), methylcyclopentane($C_6$), dimethylcyclopentane($C_7$) and methylcyclohexane($C_7$);

unsaturated monocyclic hydrocarbon compounds: cyclopropene($C_3$), cyclobutene($C_4$), cyclopentene($C_5$), cyclohexene($C_6$), methylcyclopropene($C_4$), dimethylcyclopropene($C_5$), methylcyclobutene($C_5$), dimethylcyclobutene($C_6$), methylcyclopentene($C_6$), dimethylcyclopentene($C_7$) and methylcyclohexene($C_7$); and saturated polycyclic hydrocarbon compounds: norcarane ($C_7$), norpinane($C_7$), norbornane($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:

$N_1$: aziridine($C_3$), azetidine($C_4$), pyrrolidine(tetrahydropyrrole)($C_5$), pyrroline (e.g., 3-pyrroline, 2,5-dihydropyrrole) ($C_5$), 2H-pyrrole or 3H-pyrrole(isopyrrole, isoazole)($C_5$), piperidine($C_6$), dihydropyridine($C_6$), tetrahydropyridine ($C_6$), azepine($C_7$);

$O_1$: oxirane($C_3$), oxetane($C_4$), oxolane(tetrahydrofuran)($C_5$), oxole(dihydrofuran)($C_5$), oxane(tetrahydropyran)($C_6$), dihydropyran($C_6$), pyran($C_6$), oxepin($C_7$);

$S_1$: thiirane($C_3$), thietane($C_4$), thiolane(tetrahydrothiophene) ($C_5$), thiane(tetrahydrothiopyran)($C_6$), thiepane($C_7$);

$O_2$: dioxolane($C_5$), dioxane($C_6$), and dioxepane($C_7$);

$O_3$: trioxane($C_6$);

$N_2$: imidazolidine($C_5$), pyrazolidine(diazolidine)($C_5$), imidazoline($C_5$), pyrazoline(dihydropyrazole)($C_5$), piperazine ($C_6$);

$N_1O_1$: tetrahydrooxazole($C_5$), dihydrooxazole($C_5$), tetrahydroisoxazole($C_5$), dihydroisoxazole($C_5$), morpholine($C_6$), tetrahydrooxazine($C_6$), dihydrooxazine($C_6$), oxazine($C_6$);

$N_1S_1$: thiazoline($C_5$), thiazolidine($C_5$), thiomorpholine($C_6$);

$N_2O_1$: oxadiazine($C_6$);

$O_1S_1$: oxathiole($C_5$) and oxathiane (thioxane)($C_6$); and, $N_1O_1S_1$: oxathiazine($C_6$).

Examples of substituted monocyclic heterocyclyl groups include those derived from saccharides, in cyclic form, for example, furanoses($C_5$), such as arabinofuranose, lyxofuranose, ribofuranose, and xylofuranse, and pyranoses($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. Preferably, each ring has from 5 to 7 ring atoms.

In this context, the prefixes (e.g. $C_{3-20}$, $C_{5-7}$, $C_{5-6}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups". Examples of carboaryl groups include, but are not limited to, those derived from benzene (i.e. phenyl)($C_6$), naphthalene($C_{10}$), azulene($C_{10}$), anthracene($C_{14}$), phenanthrene($C_{14}$), naphthacene($C_{18}$), and pyrene($C_{16}$).

Examples of aryl groups which comprise fused rings, at least one of which is an aromatic ring, include, but are not limited to, groups derived from indane (e.g. 2,3-dihydro-1H-indene)($C_9$), indene($C_9$), isoindene($C_9$), tetraline(1,2,3,4-tetrahydronaphthalene)($C_{10}$), acenaphthene($C_{12}$), fluorene ($C_{13}$), phenalene($C_{13}$), acephenanthrene($C_{15}$), and aceanthrene($C_{16}$).

Alternatively, the ring atoms may include one or more heteroatoms, as in "heteroaryl groups". Examples of monocyclic heteroaryl groups include, but are not limited to, those derived from:

$N_1$: pyrrole(azole)($C_5$), pyridine(azine)($C_6$);

$O_1$: furan(oxole)($C_5$);

$S_1$: thiophene(thiole)($C_5$);

$N_1O_1$: oxazole($C_5$), isoxazole($C_5$), isoxazine($C_6$);

$N_2O_1$: oxadiazole(furazan)($C_5$);

$N_3O_1$: oxatriazole($C_5$);

$N_1S_1$: thiazole($C_5$), isothiazole($C_5$);

$N_2$: imidazole(1,3-diazole)($C_5$), pyrazole(1,2-diazole)($C_5$), pyridazine(1,2-diazine)($C_6$), pyrimidine(1,3-diazine)($C_6$) (e.g., cytosine, thymine, uracil), pyrazine(1,4-diazine) ($C_6$);

$N_3$: triazole($C_5$), triazine($C_6$); and, $N_4$: tetrazole($C_5$).

Examples of heteroaryl which comprise fused rings, include, but are not limited to:

$C_9$ (with 2 fused rings) derived from benzofuran($O_1$), isobenzofuran($O_1$), indole($N_1$), isoindole($N_1$), indolizine($N_1$), indoline($N_1$), isoindoline($N_1$), purine($N_4$) (e.g., adenine, guanine), benzimidazole($N_2$), indazole($N_2$), benzoxazole($N_1O_1$), benzisoxazole($N_1O_1$), benzodioxole($O_2$), benzofurazan($N_2O_1$), benzotriazole($N_3$), benzothiofuran($S_1$), benzothiazole($N_1S_1$), benzothiadiazole($N_2S$);

$C_{10}$ (with 2 fused rings) derived from chromene($O_1$), isochromene($O_1$), chroman($O_1$), isochroman($O_1$), benzodioxan($O_2$), quinoline($N_1$), isoquinoline($N_1$), quinolizine($N_1$), benzoxazine($N_1O_1$), benzodiazine($N_2$), pyridopyridine($N_2$), quinoxaline($N_2$), quinazoline($N_2$), cinnoline($N_2$), phthalazine($N_2$), naphthyridine($N_2$), pteridine($N_4$);

$C_{11}$ (with 2 fused rings) derived from benzodiazepine($N_2$);

$C_{13}$ (with 3 fused rings) derived from carbazole($N_1$), dibenzofuran($O_1$), dibenzothiophene($S_1$), carboline ($N_2$), perimidine($N_2$), pyridoindole($N_2$); and, $C_{14}$ (with 3 fused rings) derived from acridine($N_1$), xanthene($O_1$), thioxanthene($S_1$), oxanthrene($O_2$), phenoxathiin($O_1S_1$), phenazine($N_2$), phenoxazine($N_1O_1$), phenothiazine($N_1S_1$), thianthrene($S_2$), phenanthridine($N_1$), phenanthroline($N_2$), phenazine($N_2$).

The above groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$alkyl group.

Alkoxy: —OR, wherein R is an alkyl group, for example, a $C_{1-7}$ alkyl group. Examples of $C_{1-7}$ alkoxy groups include, but are not limited to, —OMe(methoxy), —OEt(ethoxy), —O(nPr)(n-propoxy), —O(iPr)(isopropoxy), —O(nBu)n-butoxy), —O(sBu)(sec-butoxy), —O(iBu)(isobutoxy), and —O(tBu)(tert-butoxy).

Acetal: —CH($OR^1$)($OR^2$), wherein $R^1$ and $R^2$ are independently acetal substituents, for example, a $C_{1-7}$ alkyl group, a $C_{3-20}$ heterocyclyl group, or a $C_{5-20}$ aryl group, preferably a $C_{1-7}$ alkyl group, or, in the case of a "cyclic" acetal group, $R^1$ and $R^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)($OR^1$), wherein $R^1$ is a hemiacetal substituent, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a C$_{1-7}$ alkyl group, a C$_{3-20}$ heterocyclyl group, or a C$_{5-20}$ aryl group, preferably a C$_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a C$_{1-7}$ alkyl group, a C$_{3-20}$ heterocyclyl group, or a C$_{5-20}$ aryl group, preferably a C$_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo(keto, -one): =O.

Thione(thioketone): =S.

Imino(imine): =NR, wherein R is an imino substituent, for example, hydrogen, C$_{1-7}$ alkyl group, a C$_{3-20}$ heterocyclyl group, or a C$_{5-20}$ aryl group, preferably hydrogen or a C$_{1-7}$ alkyl group. Examples of ester groups include, but are not limited to, =NH, =NMe, =NEt, and =NPh.

Formyl(carbaldehyde, carboxaldehyde): —C(=O)H.

Acyl(keto): —C(=O)R, wherein R is an acyl substituent, for example, a C$_{1-7}$ alkyl group (also referred to as C$_{1-7}$ alkylacyl or C$_{1-7}$ alkanoyl), a C$_{3-20}$ heterocyclyl group (also referred to as C$_{3-20}$ heterocyclylacyl), or a C$_{5-20}$ aryl group (also referred to as C$_{5-20}$ arylacyl), preferably a C$_{1-7}$ alkyl group. Examples of acyl groups include, but are not limited to, —C(=O)CH$_3$(acetyl), —C(=O)CH$_2$CH$_3$(propionyl), —C(=O)C(CH$_3$)$_3$(t-butyryl), and —C(=O)Ph(benzoyl, phenone).

Carboxy(carboxylic acid): —C(=O)OH.

Thiocarboxy(thiocarboxylic acid): —C(=S)SH.

Thiolocarboxy(thiolocarboxylic acid): —C(=O)SH.

Thionocarboxy(thionocarboxylic acid): —C(=S)OH.

Imidic acid: —C(=NH)OH.

Hydroxamic acid: —C(=NOH)OH.

Ester(carboxylate, carboxylic acid ester, oxycarbonyl): —C(=O)OR, wherein R is an ester substituent, for example, a C$_{1-7}$ alkyl group, a C$_{3-20}$ heterocyclyl group, or a C$_{5-20}$ aryl group, preferably a C$_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy(reverse ester): —OC(=O)R, wherein R is an acyloxy substituent, for example, a C$_{1-7}$ alkyl group, a C$_{3-20}$ heterocyclyl group, or a C$_{5-20}$ aryl group, preferably a C$_{1-7}$ alkyl group. Examples of acyloxy groups include, but are not limited to, —OC(=O)CH$_3$(acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a C$_{1-7}$ alkyl group, a C$_{3-20}$ heterocyclyl group, or a C$_{5-20}$ aryl group, preferably a C$_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amino: —NR$^1$R$^2$, wherein R$^1$ and R$^2$ are independently amino substituents, for example, hydrogen, a C$_{1-7}$ alkyl group (also referred to as C$_{1-7}$ alkylamino or di-C$_{1-7}$ alkylamino), a C$_{3-20}$ heterocyclyl group, or a C$_{5-20}$ aryl group, preferably H or a C$_{1-7}$ alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido(carbamoyl, carbamyl, aminocarbonyl, carboxamide) —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido(thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Acylamido(acylamino): —NR$^1$C(=O)R$^2$, wherein R$^1$ is an amide substituent, for example, hydrogen, a C$_{1-7}$ alkyl group, a C$_{3-20}$ heterocyclyl group, or a C$_{5-20}$ aryl group, preferably hydrogen or a C$_{1-7}$ alkyl group, and R$^2$ is an acyl substituent, for example, a C$_{1-7}$ alkyl group, a C$_{3-20}$ heterocyclyl group, or a C$_{5-20}$aryl group, preferably hydrogen or a C$_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

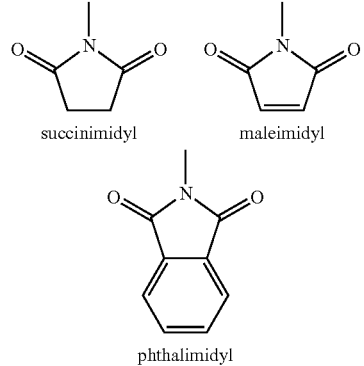

succinimidyl    maleimidyl phthalimidyl

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a C$_{1-7}$ alkyl group, a C$_{3-20}$ heterocyclyl group, or a C$_{5-20}$ aryl group, preferably hydrogen or a C$_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

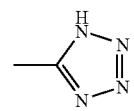

Imino: =NR, wherein R is an imino substituent, for example, for example, hydrogen, a C$_{1-7}$ alkyl group, a C$_{3-20}$ heterocyclyl group, or a $C_{5-20}$ aryl group, preferably H or a $C_{1-7}$alkyl group. Examples of imino groups include, but are not limited to, =NH, =NMe, and =NEt.

Amidine(amidino): —C(=NR)NR$_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.
Nitroso: —NO.
Azido: —N$_3$.
Cyano(nitrile, carbonitrile): —CN.
Isocyano: —NC.
Cyanato: —OCN.
Isocyanato: —NCO.
Thiocyano(thiocyanato): —SCN.
Isothiocyano(isothiocyanato): —NCS.
Sulfhydryl(thiol, mercapto): —SH.

Thioether(sulfide): —SR, wherein R is a thioether substituent, for example, a $C_{1-7}$ alkyl group (also referred to as a $C_{1-7}$alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —SSCH$_3$ and —SSCH$_2$CH$_3$.

Sulfine(sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)CH$_3$ and —S(=O)CH$_2$CH$_3$.

Sulfone(sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group, including, for example, a fluorinated or perfluorinated $C_{1-7}$ alkyl group. Examples of sulfone groups include, but are not limited to, —S(=O)$_2$CH$_3$(methanesulfonyl, mesyl), —S(=O)$_2$CF$_3$(triflyl), —S(=O)$_2$CH$_2$CH$_3$(esyl), —S(=O)$_2$C$_4$F$_9$(nonaflyl), —S(=O)$_2$CH$_2$CF$_3$(tresyl), —S(=O)$_2$CH$_2$CH$_2$NH$_2$(tauryl), —S(=O)$_2$Ph(phenylsulfonyl, besyl), 4-methylphenylsulfonyl(tosyl), 4-chlorophenylsulfonyl(closyl), 4-bromophenylsulfonyl(brosyl), 4-nitrophenyl(nosyl), 2-naphthalenesulfonate(napsyl), and 5-dimethylamino-naphthalen-1-ylsulfonate(dansyl)

Sulfinic acid(sulfino): —S(=O)OH, —SO$_2$H.
Sulfonic acid(sulfo): —S(=O)$_2$OH, —SO$_3$H.

Sulfinate(sulfinic acid ester): —S(=O)OR; wherein R is a sulfinate substituent, for example, a $C_{1-7}$ alkyl group, a $C_{3-20}$ heterocyclyl group, or a $C_{5-20}$ aryl group, preferably a $C_{1-7}$ alkyl group. Examples of sulfinate groups include, but are not limited to, —S(=O)OCH$_3$(methoxysulfinyl; methyl sulfinate) and —S(=O)OCH$_2$CH$_3$(ethoxysulfinyl; ethyl sulfinate).

Sulfonate (sulfonic acid ester): —S(=O)$_2$OR, wherein R is a sulfonate substituent, for example, a $C_{1-7}$ alkyl group, a $C_{3-20}$ heterocyclyl group, or a $C_{5-20}$ aryl group, preferably a $C_{1-7}$ alkyl group. Examples of sulfonate groups include, but are not limited to, —S(=O)$_2$OCH$_3$(methoxysulfonyl; methyl sulfonate) and —S(=O)$_2$OCH$_2$CH$_3$(ethoxysulfonyl; ethyl sulfonate).

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a $C_{1-7}$ alkyl group, a $C_{3-20}$ heterocyclyl group, or a $C_{5-20}$ aryl group, preferably a $C_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, —NHS(=O)CH$_3$ and —N(CH$_3$)S(=O)C$_6$H$_5$.

Phosphino (phosphine): —PR$_2$, wherein R is a phosphino substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a $C_{1-7}$ alkyl group, a $C_{3-20}$ heterocyclyl group, or a $C_{5-20}$ aryl group, preferably a $C_{1-7}$ alkyl group or a $C_{5-20}$ aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphate groups include, but are not limited to, —OP(=O)(OCH$_3$)$_2$, —OP((=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^2$$_2$, where R$^1$ and R$^2$ are phosphoramidite substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^2$$_2$, where R$^1$ and R$^2$ are phosphoramidate substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Alkylene $C_{3-12}$ alkylene: The term "$C_{3-12}$ alkylene", as used herein, pertains to a bidentate moiety obtained by removing two hydrogen atoms, either both from the same carbon atom, or one from each of two different carbon atoms, of a hydrocarbon compound having from 3 to 12 carbon atoms (unless otherwise specified), which may be aliphatic or alicyclic, and which may be saturated, partially unsaturated, or fully unsaturated. Thus, the term "alkylene" includes the sub-classes alkenylene, alkynylene, cycloalkylene, etc., discussed below.

Examples of linear saturated $C_{3-12}$ alkylene groups include, but are not limited to, —(CH$_2$)$_n$— where n is an integer from 3 to 12, for example, —CH$_2$CH$_2$CH$_2$— (propylene), —CH$_2$CH$_2$CH$_2$CH$_2$— (butylene), —CH$_2$CH$_2$CH$_2$CH$_2$CH$_2$— (pentylene) and —CH$_2$CH$_2$CH$_2$CH$_2$CH$_2$CH$_2$CH$_2$— (heptylene).

Examples of branched saturated $C_{3-12}$ alkylene groups include, but are not limited to, —CH(CH$_3$)CH$_2$—, —CH(CH$_3$)CH$_2$CH$_2$—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$—.

Examples of linear partially unsaturated $C_{3-12}$ alkylene groups ($C_{3-12}$ alkenylene, and alkynylene groups) include, but are not limited to, —CH=CH—CH$_2$—, —CH$_2$—CH=CH$_2$—, —CH=CH—CH$_2$—CH$_2$—, —CH=CH—CH$_2$—CH$_2$—CH$_2$—, —CH=CH—CH=CH—, —CH=CH—CH=CH—CH$_2$—, —CH=CH—CH=CH—CH$_2$—CH$_2$—, —CH=CH—CH$_2$—CH=CH—, —CH=CH—CH$_2$—CH$_2$—CH=CH—, and —CH$_2$—C≡C—CH$_2$—.

Examples of branched partially unsaturated $C_{3-12}$ alkylene groups ($C_{3-12}$ alkenylene and alkynylene groups) include, but are not limited to, —C(CH$_3$)=CH—, —C(CH$_3$)=CH—CH$_2$—, —CH=CH—CH(CH$_3$)— and —C≡C—CH(CH$_3$)—.

Examples of alicyclic saturated $C_{3-12}$ alkylene groups ($C_{3-12}$ cycloalkylenes) include, but are not limited to, cyclopentylene (e.g. cyclopent-1,3-ylene), and cyclohexylene (e.g. cyclohex-1,4-ylene).

Examples of alicyclic partially unsaturated $C_{3-12}$ alkylene groups ($C_{3-12}$ cycloalkylenes) include, but are not limited to, cyclopentenylene (e.g. 4-cyclopenten-1,3-ylene), cyclohexenylene (e.g. 2-cyclohexen-1,4-ylene; 3-cyclohexen-1,2-ylene; 2,5-cyclohexadien-1,4-ylene).

Proliferative Diseases

One of ordinary skill in the art is readily able to determine whether or not a candidate compound treats a proliferative condition for any particular cell type. For example, assays which may conveniently be used to assess the activity offered by a particular compound are described in the examples below.

The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), leukemias, psoriasis, bone diseases, fibroproliferative disorders (e.g. of connective tissues), and atherosclerosis.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

Methods of Treatment

As described above, the present invention provide the use of a compound of formula III in a method of therapy. Also provided is a method of treatment, comprising administering to a subject in need of treatment a therapeutically-effective amount of a compound of formula III, preferably in the form of a pharmaceutical composition, which is the third aspect of the present invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound may be administered alone or in combination with other treatments, either simultaneously or sequentially dependent upon the condition to be treated. Examples of treatments and therapies include, but are not limited to, chemotherapy (the administration of active agents, including, e.g. drugs; surgery; and radiation therapy. If the compound of formula III bears a carbamate-based nitrogen protecting group which may be removed in vivo, then the methods of treatment described in WO 00/12507 (ADEPT, GDEPT and PDT) may be used.

Pharmaceutical compositions according to the present invention, and for use in accordance with the present invention, may comprise, in addition to the active ingredient, i.e. a compound of formula III, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Includes other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Isomers, Salts and Solvates

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Preferably compounds of the present invention have the following stereochemistry at the C11 position:

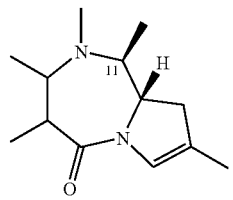

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain too tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

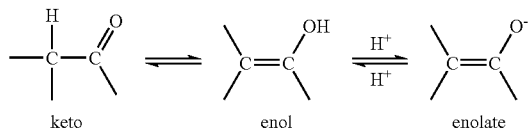

keto    enol    enolate

Note that specifically included in the term "isomer" are compounds with one or more isotopic substitutions. For example, H may be in any isotopic form, including $^1$H, $^2$H(D), and $^3$H(T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Example s of pharmaceutically acceptable salts are discussed in Berge, et al., J. Pharm. Sci., 66, 1-19 (1977).

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

A particular salt form of interest can be formed from compounds of formula III, where $R^{10}$ and $R^{16}$ form an imine bond, by reacting said compound with a bisulphite salt to form a bisulphite derivative of the PBD. These compounds can be represented as:

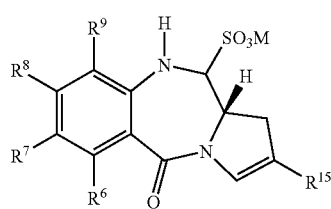

IV where M is a monovalent pharmaceutically acceptable cation, or if the compound is a dimer, the two M groups may together represent a divalent pharmaceutically acceptable cation, and the other groups are as previously defined.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Solvates of particular relevance to the present invention are those where the solvent adds across the imine bond of the PBD moiety, which is illustrated below where the solvent is water or an alcohol ($R^4$OH, where $R^4$ is an ether substituent as described above):

These forms can be called the carbinolamine and carbinolamine ether forms of the PBD. The balance of these equilibria depend on the conditions in which the compounds are found, as well as the nature of the moiety itself.

In general any nucleophilic solvent is capable of forming such solvates as illustrated above for hydroxylic solvents. Other nucleophilic solvents include thiols and amines.

These solvates may be isolated in solid form, for example, by lyophilisation.

General Synthetic Routes

The synthesis of PBD compounds is extensively discussed in WO 00/12508, which discussion is incorporated herein by reference.

As discussed in that patent application, a key step in a preferred route to PBDs is a cyclisation to produce the B-ring, involving generation of an aldehyde (or functional equivalent thereof) at what will be the 11-position, and attack thereon by the Pro-N10-nitrogen:

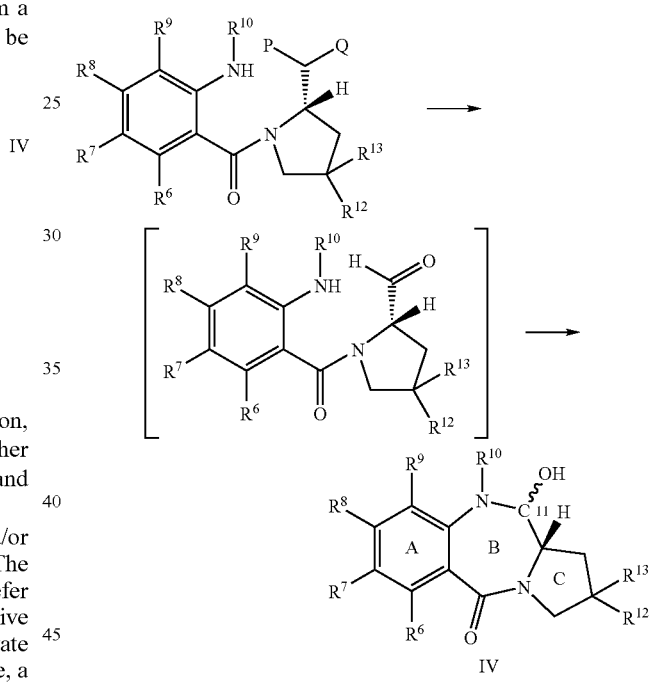

IV wherein the substituents are as defined in the second aspect of the invention. The "masked aldehyde" —CPQ may be an acetal or thioacetal, in which case the cyclisation involves unmasking. Alternatively, it may be an alcohol —CHOH, in

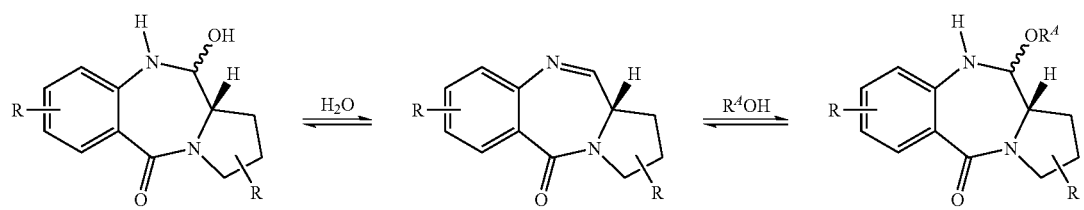

which case the reaction involves oxidation, e.g. by means of TPAP, TEMPO or DMSO (Swern oxidation).

In this reaction, $R^{12}$ is preferably $O-R^{14}$, i.e. a protected hydroxy group, and $R^{13}$ is H.

The masked aldehyde compound can be produced by condensing a corresponding 2,4-substituted pyrrolidine with a 2-nitrobenzoic acid:

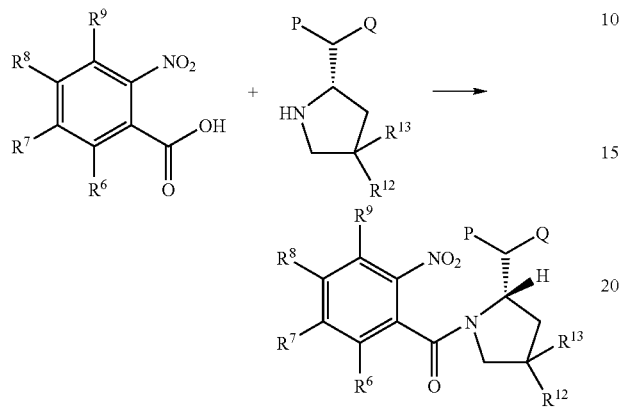

The nitro group can then be reduced to $-NH_2$ and protected by reaction with a suitable agent, e.g. a chloroformate, which provides the removable nitrogen protecting group in the compound of formula IV.

A process involving the oxidation-cyclization procedure is illustrated in scheme 1 (an alternative type of cyclisation will be described later with reference to scheme 2).

Scheme 1

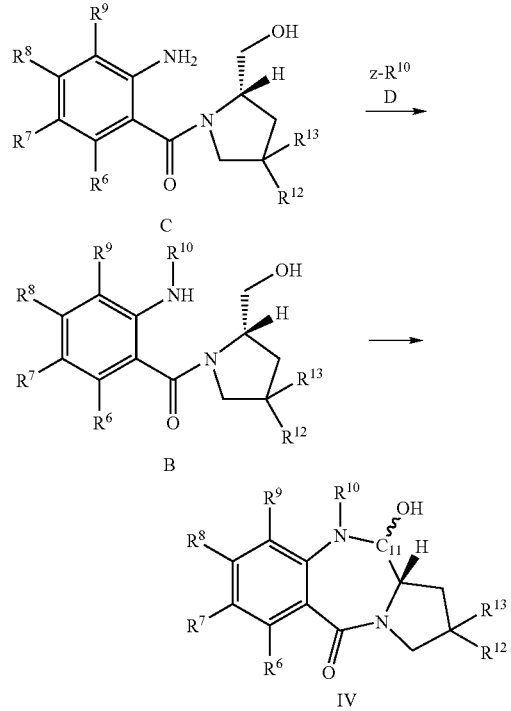

Exposure of the alcohol (B) (in which the Pro-N10-nitrogen is generally protected as carbamate) to tetrapropylammonium perruthenate (TPAP)/N-methylmorpholine N-oxide (NMO) over A4 sieves results in oxidation accompanied by spontaneous B-ring closure to afford the desired product IV. The TPAP/NMO oxidation procedure is found to be particularly convenient for small scale reactions while the use of DMSO-based oxidation methods, particularly Swern oxidation, proves superior for larger scale work (e.g. >1 g). A particularly preferred oxidising agent is (diacetoxyiodo)benzene (1.1 eq) and TEMPO (0.1 eq) dissolved in $CH_2Cl_2$.

The uncyclized alcohol (B) may be prepared by the reaction of a nitrogen protection reagent of formula D, which is preferably a chloroformate or acid chloride, to a solution of the amino alcohol C, generally in solution, generally in the presence of a base such as pyridine (preferably 2 equivalents) at a moderate temperature (e.g. at 0° C.). Under these conditions little or no O-acylation is usually observed.

The key amino alcohol C may be prepared by reduction of the corresponding nitro compound E, by choosing a method which will leave the rest of the molecule intact. Treatment of E with tin (II) chloride in a suitable solvent, e.g. refluxing methanol, generally affords, after the removal of the tin salts, the desired product in high yield.

Exposure of E to hydrazine/Raney nickel avoids the production of tin salts and may result in a higher yield of C, although this method is less compatible with the range of possible C and A-ring substituents. For instance, if there is C-ring unsaturation (either in the ring itself, or in $R_2$ or $R_3$), this technique may be unsuitable. Another suitable means of reduction would be catalytic hydrogenation using palladium on carbon as a catalyst.

The nitro compound of formula E may be prepared by coupling the appropriate o-nitrobenzoyl chloride to a compound of formula F, e.g. in the presence of $K_2CO_3$ at −25° C. under a $N_2$ atmosphere. Compounds of formula F can be readily prepared, for example by olefination of the ketone derived from L-trans-hydroxy proline. The ketone intermediate can also be exploited by conversion to the enol triflate for use in palladium mediated coupling reactions.

The o-nitrobenzoyl chloride is synthesised from the o-nitrobenzoic acid (or alkyl ester after hydrolysis) of formula G, which itself is prepared from the vanillic acid (or alkyl ester) derivative H. Many of these are commercially available and some are disclosed in Althuis, T. H. and Hess, H. J., *J. Medicinal Chem.*, 20(1), 146-266 (1977).

Alternative Cyclisation (Scheme 2)

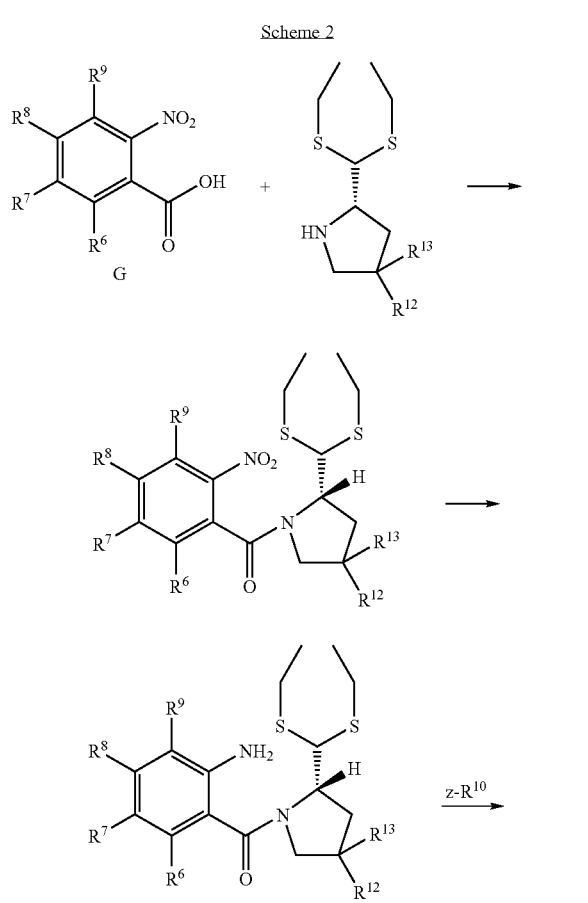

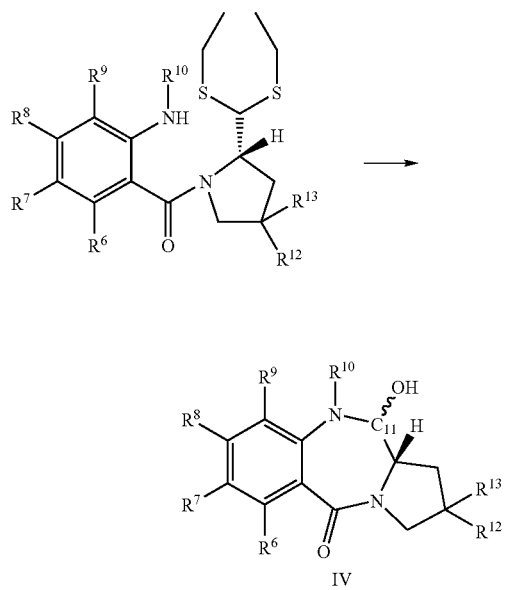

In scheme 1, the final or penultimate step was an oxidative cyclisation. An alternative, using thioacetal coupling, is shown in scheme 2. Mercury-mediated unmasking causes cyclisation to the protected PBD compound IV.

The thioacetal compound may be prepared as shown in scheme 2: the thioacetal protected C-ring [prepared via a literature method: Langley, D. R. & Thurston, D. E., *J. Organic Chemistry*, 52, 91-97 (1987)] is coupled to the o-nitrobenzoic acid (or alkyl ester after hydrolysis) (G) using a literature procedure. The resulting nitro compound cannot be reduced by hydrogenation, because of the thioacetal group, so the tin(II) chloride method is used to afford the amine. This is then N-protected, e.g., by reaction with a chloroformate or acid chloride, such as 2,2,2-trichloroethylchloroformate.

Acetal-containing C-rings can be used as an alternative in this type of route with deprotection involving other methods, including the use of acidic conditions.

Dimer Synthesis (Scheme 3)

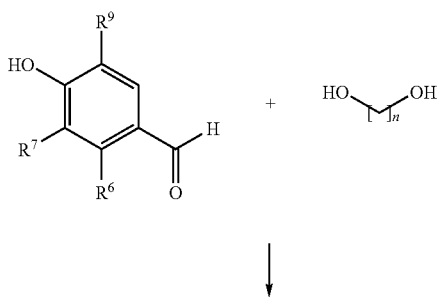

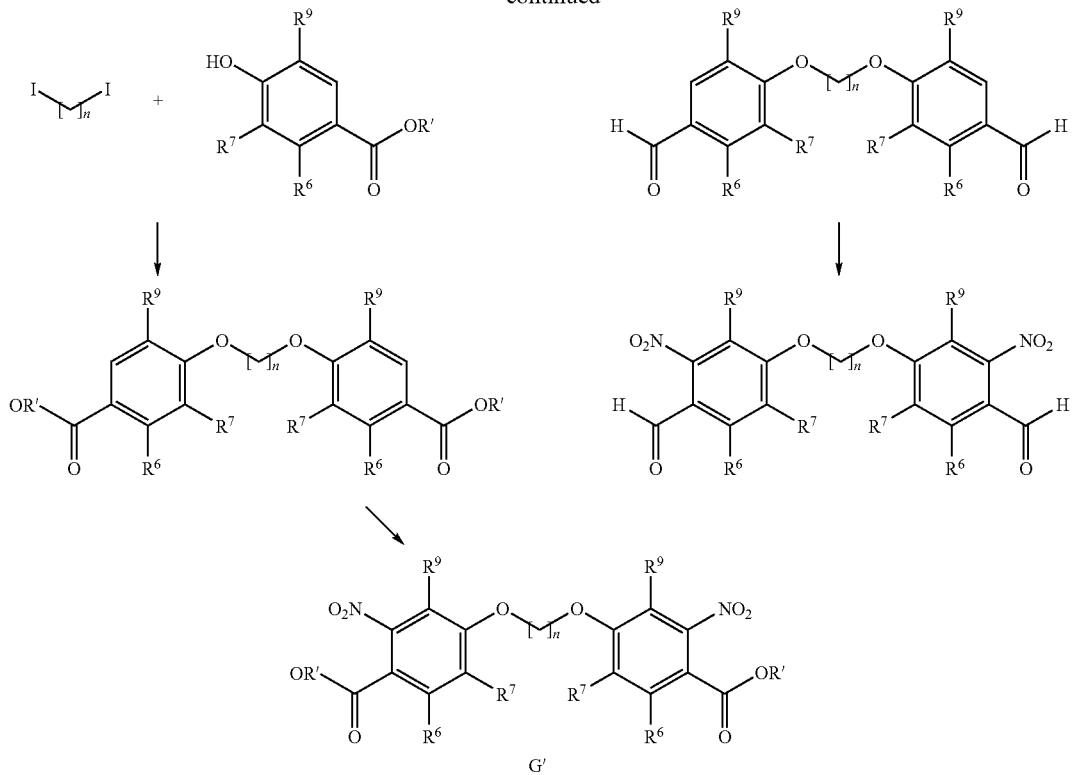

PBD dimers may be synthesized using the strategy developed for the synthesis of the protected PBD monomers. The synthesis routes illustrated in scheme 3 show compounds when the dimer linkage is of the formula —O—$(CH_2)_n$—O—. The step of dimer formation is normally carried out to form a bis(nitro acid) G'. This compound can then be treated as compound G in either scheme 1 or scheme 2 above.

The bis(nitro acid) G' may be obtained by nitrating (e.g. using 70% nitric acid) the bis(carboxylic acid). This can be synthesised by alkylation of two equivalents of the relevant benzoic acid with the appropriate diiodoalkane under basic conditions. Many benzoic acids are commercially available and others can be synthesised by conventional methods. Alternatively, the relevant benzoic acid esters can be joined together by a Mitsunobu etherification with an appropriate alkanediol, followed by nitration, and then hydrolysis (not illustrated).

An alternative synthesis of the bis(nitro acid) involves oxidation of the bis(nitro aldehyde), e.g. with potassium permanganate. This can be obtained in turn by direct nitration of the bis(aldehyde), e.g. with 70% $HNO_3$. Finally, the bis(aldehyde) can be obtained via the Mitsunobu etherification of two equivalents of the benzoic aldehyde with the appropriate alkanediol.

Alternative Routes to PBDs

Alternative methods of synthesising N10 protected PBDs are disclosed in co-pending application PCT/GB2004/003873 (filed 10 Sep. 2004) which claims priority from GB0321295.8 (filed 11 Sep. 2003), which describes the use of isocyanate intermediates.

Formation of Compound of formula I

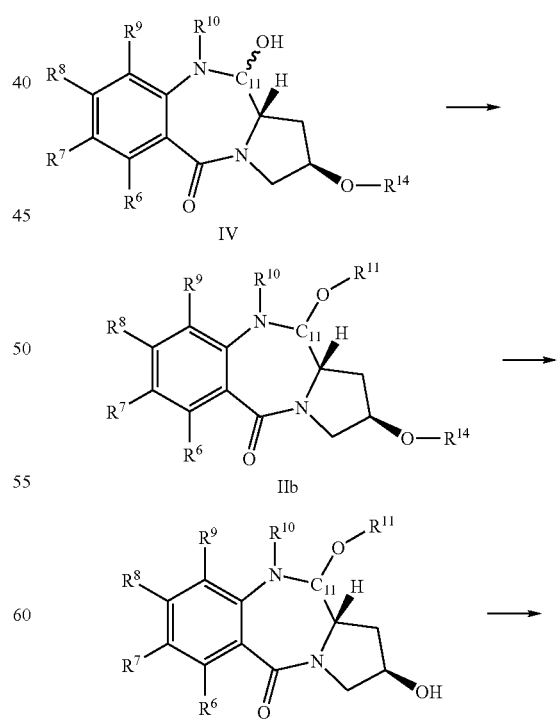

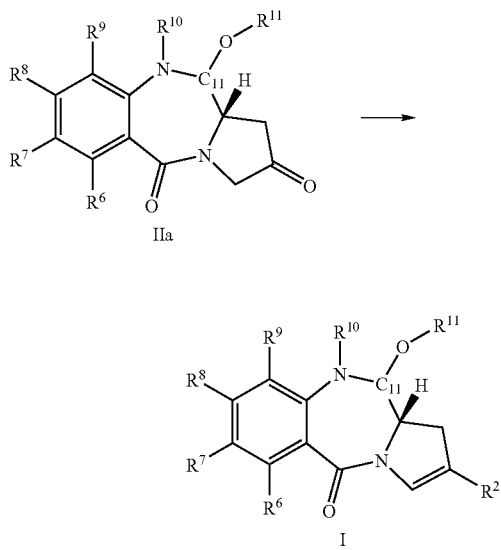

Following cyclisation to form the B-ring, the C11-alcohol IV is then preferably re-protected, by conventional means to provide IIb. For example, if $R^{11}$ is TBS, the protection can take place by reacting IV with TBSOTf and 2,6-lutidine. Cleavage of the C2-protecting group from IIb then provides the C2 alcohol. For example, where the C2 protecting group ($R^{14}$) is acyl, this deprotection may be performed by addition of an aqueous solution of $K_2CO_3$.

This reprotection at the C11 position and deprotection of the C2 alcohol allows subsequent reaction of selectively the C2 alcohol position leaving the C11 position unaffected.

The C2-alcohol may then be oxidized to the ketone IIb. Preferably this oxidation is performed under Swern conditions, in good yield. However, other oxidation methods involving TPAP or the Dess Martin reagent also provide the ketone in good yield.

If $R^2$ in the compound of formula I is —$OSO_2CH_3$, —$OSO_2(C_nF_{2n+1})$ where n=0, 1 or 4, or —$OSO_2R^s$, then the conversion from IIb may be achieved by treatment with the appropriate anhydride. For example, if $R^2$ is triflate that reaction with trifluoromethanesulfonic anhydride n DAM in the presence of pyridine.

If $R^2$ in the compound of formula I is —I or —Br, then the conversion from IIb may be achieved by reaction with hydrazine and iodine or bromine respectively.

If $R^2$ in the compound of formula I is —Cl, then the conversion from IIb may be achieved by reaction with a phosphorous oxychloride (e.g. $POCl_3$).

Synthesis of Compounds of Formula III

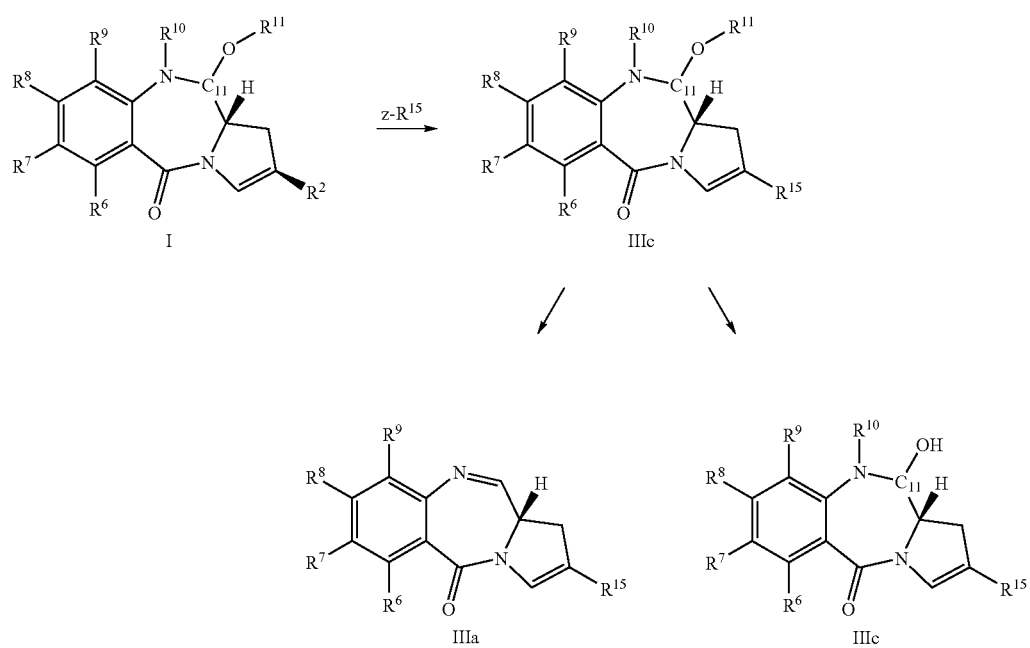

This compound of formula I may be reacted under a variety of conditions to yield PBD precursor molecules with pendant groups coupled at the C2 position IIIc.

In particular, the use of palladium catalysed coupling is preferred, such as Suzuki, Stille and Heck coupling. The palladium catalyst may be any suitable catalyst, for example $Pd(PPh_3)_4$, $Pd(OCOCH_3)_2$, $PdCl_2$, $Pd(dba)_3$. The compounds which are coupled may be any suitable reactant, e.g. for Heck, alkenes with an $sp^2$ H; for Stille, organostannanes; and for Suzuki, organoboron derivatives.

In a preferred aspect of the invention, the coupling may be performed under microwave conditions. Typically, the palladium catalyst, such as $Pd(PPh_3)_4$, is solid supported, for example on polystyrene, to facilitate work-up and allow potential recycling of catalyst. Unreacted boronic acid can be sequestered following complete consumption of triflate using PS-DEAM, with a phase separator cartridge being used to isolate the coupling product. Such a method allows for the parallel synthesis of more than one (e.g. up to 10, 20 or 30) compound at the same time.

The imine bond in the compound of formula IIIc can be unprotected by standard methods to yield the unprotected compound IIIa (which may be in its carbinolamine or carboinolamine ether form, depending on the solvents used). For example if $R^{10}$ is Alloc, then the deprotection is carried using palladium to remove the N10 protecting group, followed by the elimination of water. If $R^{10}$ is Troc, then the deprotection is carried out using a Cd/Pb couple to yield the compound of formula IIIa.

If the nitrogen protecting group ($R^{10}$) is such that the desired end product still contains it, e.g. if it is removable in vivo, then the compound of formula IIIb may be synthesised by removal of the oxygen protecting groups under suitable conditions.

Further Preferences

The following preferences may apply to all aspects of the invention as described above, or may relate to a single aspect. The preferences may be combined together in any combination.

$R^6$ to $R^9$

If the compound is a dimer, it is preferred that the dimer bridge is of formula —O—$(CH_2)_n$—O—, where n is from 3 to 12, and more preferably 3 to 7. It is preferred that the substituents $R^8$ join to form the dimer bridge.

$R^9$ is preferably H.

$R^6$ is preferably selected from H, OH, OR, SH, $NH_2$, nitro and halo, and is more preferably H or halo, and most preferably is H.

$R^7$ and $R^8$ (when the compound is not a dimer) are preferably independently selected from H, OH, OR, SH, SR, $NH_2$, NHR, NRR', and halo, and more preferably independently selected from H, OH and OR, where R is preferably selected from optionally substituted $C_{1-7}$ alkyl, $C_{3-10}$ heterocyclyl and $C_{5-10}$ aryl groups. Particularly preferred substituents at the 7- and 8-positions are OMe and $OCH_2Ph$.

In the first aspect of the invention, $R^{10}$ is preferably Troc. $R^{11}$ is preferably a silyl oxygen protecting group (more preferably TBS) or THP. $R^2$ is preferably triflate. Accordingly, in a particularly preferred embodiment of the first aspect of the invention, $R^{10}$ is Troc, $R^{11}$ is TBS or THP and $R^2$ is triflate.

In the second aspect of the invention, $R^{14}$ is preferably a methyl ester. $R^{11}$ is preferably a silyl oxygen protecting group (more preferably TBS) or THP. Accordingly, in a particularly preferred embodiment of the second aspect of the invention $R^{14}$ is a methyl ester and $R^{11}$ is TBS or THP. Furthermore, $R^{10}$ is preferably Troc.

In some embodiments of the third aspect of the invention, $R^{10}$ is preferably Troc and $R^{16}$ is O—$R^{11}$, wherein $R^{11}$ is preferably a silyl oxygen protecting group (more preferably TBS) or THP.

In other embodiments of the third aspect of the invention, $R^{10}$ and $R^{16}$ together form a double bond between N10 and C11.

In the third aspect of the invention $R^{15}$ is preferably selected from optionally substituted $C_{5-20}$ aryl groups and optionally substituted $C_{1-7}$ alkyl groups, which group has a carbon-carbon double or triple bond conjugated to the double bond in the C-ring.

Novel compounds of the present invention preferably have $R^{10}$ and $R^{16}$ forming a double bond between N10 and C11. Preferably, the novel compounds of the invention are dimers through C8, i.e. the $R^8$ groups of each monomer form together a dimer bridge having the formula —X—R"—X— linking the monomers. More preferably, the dimer bridge is of formula —O—$(CH_2)_n$—O—, where n is 3 to 12, more preferably 3, 5, or 7. The preferences for $R^6$, $R^7$ and $R^9$ are as expressed above. $R^{15}$ is preferably selected from:

(i) optionally substituted $C_{5-20}$ aryl groups;
(ii) substituted $C_2$ alkyl groups; and
(iii) optionally substituted $C_{3-7}$ alkyl groups.

In particular groups (ii) and (iii) above, preferably have a carbon-carbon double or triple bond conjugated to that between C2 and C3.

Group (i) above are more preferably optionally substituted $C_{5-7}$ aryl groups, and most preferably optionally substituted phenyl groups.

Group (ii) is preferably either a vinyl group substituted with an amido group, and more preferably with an amido group which is —C(=O)N$(CH_3)_2$; or a ethynyl group substituted with an optionally substituted $C_{5-7}$ aryl group, more preferably phenyl.

Group (iii) is preferably an optionally substituted propylene group, for example —CH=CH—$CH_3$.

If R is optionally substituted $C_{1-12}$ alkyl, it is preferred that it is optionally substituted $C_{1-7}$ alkyl.

EXAMPLES

Example 1

Formation of key Dimer Intermediate (2-[[(trifluoromethyl)sulfonyl]oxy]-1,10,11,11a-tetrahydro-5H-pyrrolo[2,1-c][1,4]benzodiazepin-5-one]] (13))

(2S,4R)-N-(Benzyloxycarbonyl)-2-t-butyldimethyl-silyloxymethyl-4-hydroxypyrrolidine (1)

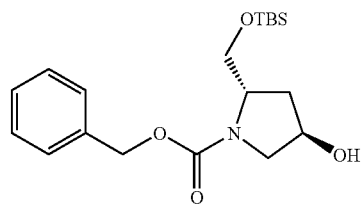

Compound 1 is formed in high yield in a four step process known in the art starting from trans-4-hydroxy-L-proline (S. J. Gregson et al., *J. Med. Chem.*, 2004, 1161-1174).

(2S,4R)-N-(Benzyloxycarbonyl-2-t-butyldimethylsilyloxymethyl-4-oxyacetylpyrrolidine (2)

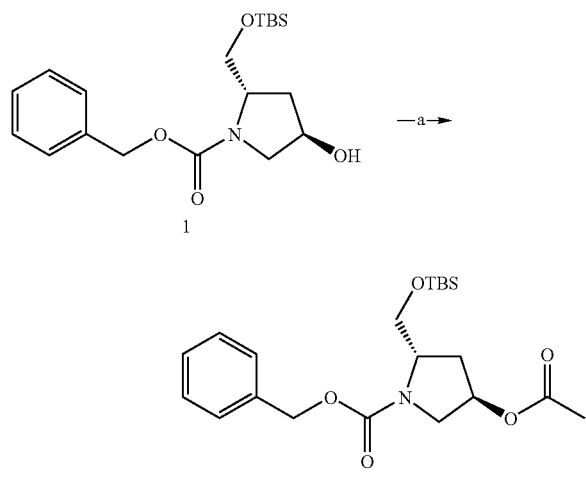

(a) pyridine, Ac$_2$O, DMAP, THF, 16 h, 96%;

Pyridine (18.3 g, 18.7 mL, 232 mmol, 1.1 eq), acetic anhydride (23.6 g, 21.8 mL, 232 mmol, 1.1 eq) and DMAP (5.14 g, 42.1 mmol, 0.2 eq) were added to a stirred solution of 1 (76.9 g, 211 mmol) in dry THF (1 L). The reaction mixture was stirred for 16 hours after which time TLC (95:5 v/v CHCl$_3$/MeOH) showed the complete consumption of starting material. Excess solvent was removed by rotary evaporation and the residue was dissolved in EtOAc (1 L), washed with 1N HCl (2×1 L), H$_2$O (1 L), brine (1 L) and dried (MgSO$_4$). Filtration and evaporation of the solvent afforded acetate 2 as a colourless oil (80.7 g, 94%): $^1$H NMR (400 MHz, CDCl$_3$) (rotamers) δ 7.36-7.12 (m, 5H), 5.30-5.10 (m, 3H), 4.09-3.97 (m, 2H), 3.74-3.55 (m, 3H), 2.36-2.29 (m, 1H), 2.11-2.06 (m, 1H), 2.02 (s, 3H), 0.87 (s, 6H), 0.86 (s, 3H), 0.03 and 0.00 (s×2, 6H); MS (ES), m/z (relative intensity) 430 ([M+Na]$^+$, 95), 408 ([M+H]$^+$, 100).

(2S,4R)-2-t-Butyldimethylsilyloxymethyl-4-oxyacetylpyrrolidine (3)

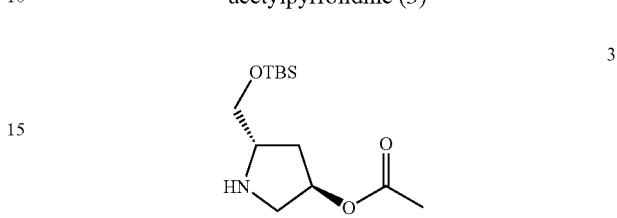

A slurry of silyl ether 2 (1.95 g, 4.80 mmol) and 10% Pd/C (0.17 g) in absolute ethanol (10 mL) was subjected to Parr hydrogenation at 45 Psi for 16 h after which time TLC (95:5 v/v CHCl$_3$/MeOH) showed the complete consumption of starting material. The reaction mixture was filtered through celite to remove the Pd/C, and the filter pad was washed repeatedly with ethanol. Excess solvent was removed by rotary evaporation under reduced pressure to afford the amine 3 as a pale orange waxy oil (1.28 g, 98%): IR (CHCl$_3$) 3315, 2930, 2858, 1739, 1652, 1472, 1435, 1375, 1251, 1088, 838, 779, 667 cm$^{-1}$.

1,1'-[[(Propane-1,3-diyl)dioxy]bis[(2S,4R)-(5-methoxy-2-nitro-1,4-phenylene)carbonyl]]bis[2-(tert-butyldimethylsilyloxymethyl)-4-oxyacetylpyrrolidine] (5)

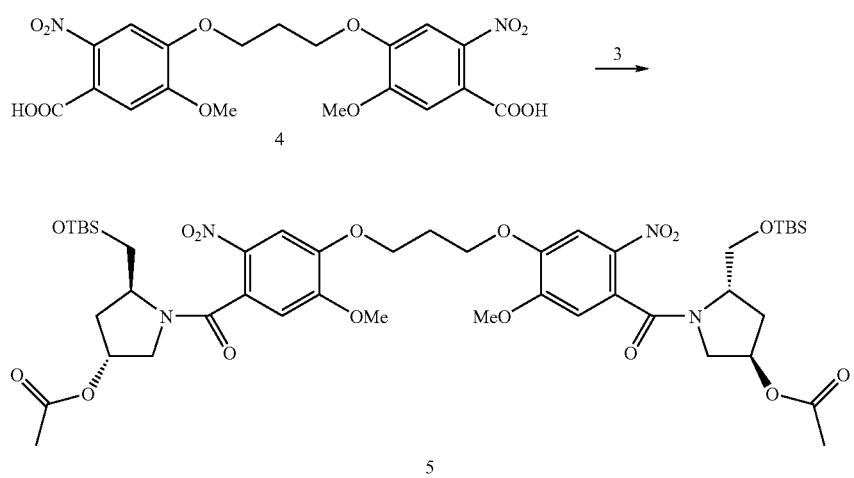

A catalytic amount of DMF (2 drops) was added to a stirred solution of the nitro-acid 4 (8.12 g, 17.4 mmol)$^1$ and oxalyl chloride (3.80 mL, 5.52 g, 43.5 mmol, 2.5 eq) in dry THF (250 mL). The initial precipitate dissolved gradually and the reaction mixture was allowed to stir for 16 h at room temperature. The resulting acid chloride solution was added dropwise to a stirred mixture of the amine 3 (11.9 g, 43.5 mmol, 2.5 eq), TEA (9.71 mL, 7.05 g, 69.7 mmol, 4.0 eq) and $H_2O$ (2.26 mL) in THF (100 mL) at 0° C. (ice/acetone) under a nitrogen atmosphere. The reaction mixture was allowed to warm to room temperature and stirred for a further 2.5 h. Excess THF was removed by rotary evaporation and the resulting residue was partitioned between $H_2O$ (400 mL) and EtOAc (400 mL). The layers were allowed to separate and the aqueous layer was extracted with EtOAc (3×200 mL). The combined organic layers were then washed with saturated $NH_4Cl$ (200 mL), saturated $NaHCO_3$ (200 mL), brine (200 mL) and dried ($MgSO_4$). Filtration and evaporation of the solvent gave the crude product as a dark oil. Purification by flash chromatography (99.7:0.3 v/v $CHCl_3$/MeOH) isolated the pure amide 5 as a light yellow glass (13.3 g, 78%): $^1H$ NMR (400 MHz, $CDCl_3$) δ 7.60 (s, 2H), 6.60 (s, 2H), 5.06 (br s, 2H), 4.44 (br s, 2H), 4.25-4.20 (m, 4H), 4.10-4.08 (m, 2H), 3.80 (s, 6H), 3.64-3.62 (m, 2H), 3.36-3.32 (m, 2H), 3.11-3.08 (m, 2H), 2.36-2.26 (m, 4H), 2.13-2.08 (m, 2H), 1.92 (s, 6H), 0.80 (s, 18H), 0.00 (s×2, 12H); $^{13}C$ NMR (100.6 MHz, $CDCl_3$) δ 171.0, 166.3, 154.5, 148.2, 137.4, 128.0, 127.2, 109.2, 108.5, 72.9, 65.6, 62.6, 57.4, 56.5, 54.8, 33.0, 28.6, 25.8, 21.0, 18.1; MS (ES), m/z (relative intensity) 1000 ([M+Na]$^{+\cdot}$, 39), 978 ([M+H]$^{+\cdot}$, 63), 977 (M$^{+\cdot}$, 100), 812 (13).

1,1'-[[(Propane-1,3-diyl)dioxy]bis[(2S,4R)-(5-methoxy-2-amino-1,4-phenylene)carbonyl]]bis[2-(tert-butyldimethylsilyloxymethyl)-4-oxyacetylpyrrolidine] (6)

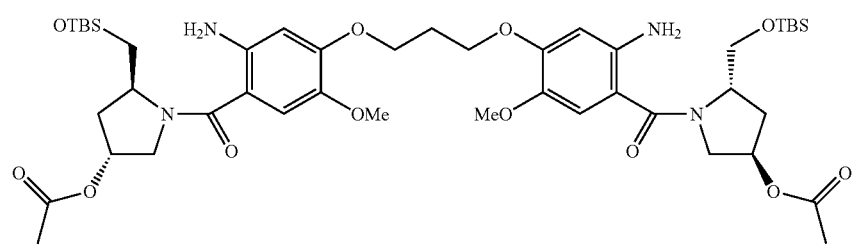

Sodium dithionite (16.59 g, 95.27 mmol, 5 eq) was added to a stirred solution of amide 5 (18.6 g, 19.1 mmol) in $H_2O$ (200 mL) and THF (400 mL). The reaction mixture was allowed to stir for 36 h after which time excess THF was removed by rotary evaporation and the resulting residue was extracted with EtOAc (3×250 mL). The combined organic layers were then washed with $H_2O$ (300 mL), brine (300 mL) and dried ($MgSO_4$). Filtration and evaporation of the solvent yielded the crude product which was purified by flash chromatography (80:20 v/v hexane/EtOAc then gradient to neat EtOAc) to afford the product 6 as a yellow foam (9.53 g, 55%): $^1H$ NMR (400 MHz, $CDCl_3$) (rotamers) δ 6.70 and 6.67 (s×2, 2H), 6.25 and 6.23 (s×2, 2H), 5.20 (br s, 2H), 4.49 (br s, 4H), 4.16-4.05 (m, 6H), 3.70 (s, 6H), 3.68-3.57 (m, 4H), 2.36-2.27 (m, 4H), 2.12-2.04 (m, 2H), 1.96 (s, 6H), 0.85 (s, 18H), 0.01 and 0.00 (s×2, 12H); $^{13}C$ NMR (100.6 MHz, $CDCl_3$) δ 170.6, 170.0, 141.1, 116.3, 113.1, 102.3, 102.1, 102.0, 66.2, 65.3, 65.2, 57.0, 28.9, 18.2; MS (ES), m/z (relative intensity) 946 (M$^{+\cdot}$+29, 43), 933 ([M+16]$^{+\cdot}$, 61), 932 ([M+15]$^{+\cdot}$, 100), 918 ([M+H]$^{+\cdot}$, 72).

1,1'-[[(Propane-1,3-diyl)dioxy]bis[(2S,4R)-[5-methoxy-1,4-phenylene-2-(2,2,2-trichloroethoycarbonylamino)]carbonyl]]bis[2-(tert-butyldimethylsilyloxymethyl)-4-oxyacetylpyrrolidine] (7)

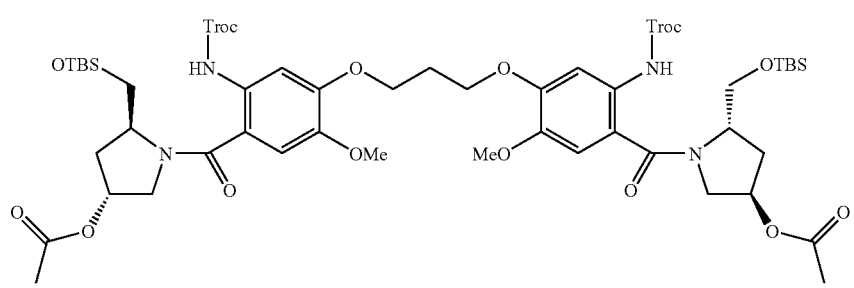

A solution of 2,2,2-trichloroethyl chloroformate (3.58 mL, 5.50 g, 26.0 mmol, 2.2 eq) in dry DCM (60 mL) was added dropwise to a solution of anhydrous pyridine (3.82 mL, 3.80 g, 47.2 mmol, 4.0 eq) and bis-aniline 6 (10.8 g, 11.8 mmol) in dry DAM (150 mL) at −10° C. (liq. $N_2$/ethanediol). After 16 h at room temperature, the reaction mixture was washed with saturated $NH_4Cl$ (2×150 mL), saturated $CuSO_4$ (150 mL), $H_2O$ (150 mL), brine (150 mL) and dried ($MgSO_4$). Filtration and evaporation of the solvent yielded a yellow viscous oil which was purified by flash chromatography (70:30 v/v hexane/EtOAc) to afford the product 7 as a white glass (13.8 g, 92%): $^1H$ NMR (400 MHz, $CDCl_3$) δ 9.42 (br s, 1H), 7.83 (s, 2H), 6.76 and 6.74 (s×2, 2H), 5.21 (br s, 2H), 4.79 and 4.73 (d×2, 4H, J=12.0 Hz), 4.56 (br s, 2H), 4.26-4.23 (m, 4H), 4.09-4.04 (m, 2H), 3.74 (s, 6H), 3.72-3.68 (m, 2H), 3.60 (br s, 4H), 2.40-2.32 (m, 4H), 2.23-2.08 (m, 2H), 1.95 (s, 6H), 0.85 (s, 18H), 0.01 and 0.00 (s×2, 12H); $^{13}C$ NMR (100.6 MHz, $CDCl_3$) δ 170.4, 169.2, 151.9, 151.5, 150.8, 143.4, 132.6, 114.4, 111.7, 95.3, 74.4, 65.5, 65.4, 57.3, 56.4, 32.5, 28.8, 25.8, 21.1, 18.1, 14.9; MS (ES), m/z (relative intensity) 1306 ([M+38]$^{+\cdot}$, 92), 1304 ([M+36]$^{+\cdot}$, 100), 1282 ([M+14]$^{+\cdot}$, 97), 1280 ([M+12]$^{+\cdot}$, 55).

1,1'-[[(Propane-1,3-diyl)dioxy]bis[(2S,4R)-[5-methoxy-1,4-phenylene-2-(2,2,2-trichloroethoxycarbonylamino)]carbonyl]]bis(2-hydroxymethyl-4-oxyacetylpyrrolidine) (8)

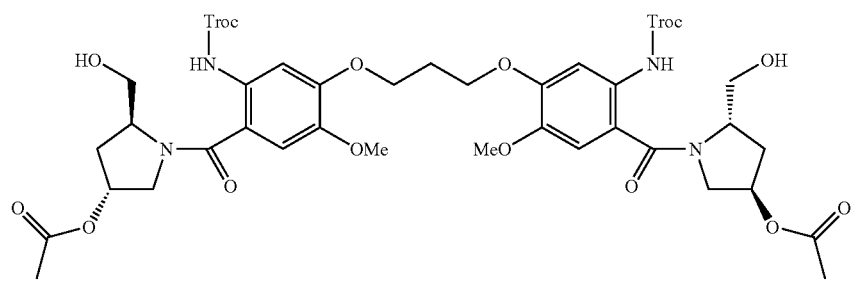

A mixture of glacial acetic acid (310 mL) and H$_2$O (100 mL) was added to a solution of 7 (13.8 g, 10.9 mmol) in THF (250 mL) and was stirred for 16 h at room temperature. The reaction mixture was diluted with DCM (750 mL) and neutralised with saturated NaHCO$_3$ (5 L). The aqueous layer was extracted with DAM (3×500 mL) and the organic layers were combined, washed with brine (1 L) and dried (MgSO$_4$). TLC (60:40 v/v hexane/EtOAc) revealed the complete disappearance of the starting material. Filtration and evaporation of the solvent afforded the crude product which was purified by flash column chromatography (99.7:0.3 v/v CHCl$_3$/MeOH then gradient to 96:4 v/v CHCl$_3$/MeOH) to provide the product 8 as a white glass (11.6 g, >100%): $^1$H NMR (500 MHz, CDCl$_3$) δ 8.92 (br s, 2H), 7.55 (s, 1H), 6.71 (s, 1H), 5.18 (br s, 2H), 4.78 (d, 2H, J=12.0 Hz), 4.72 (d, 2H, J=12.0 Hz), 4.50 (br s, 2H), 4.22-4.19 (m, 4H), 4.00 (br s, 2H), 3.78 (s, 6H), 3.76-3.52 (m, 6H), 2.32-2.30 (m, 2H), 2.21-2.17 (m, 2H), 2.09-2.04 (m, 2H) 1.94 (s, 6H); $^{13}$C NMR (125.8 MHz, CDCl$_3$) δ 170.4, 152.2, 149.8, 145.0, 111.3, 106.5, 95.6, 74.4, 72.5, 65.4, 64.1, 58.7, 56.5, 56.3, 33.6, 29.1, 21.1.

1,1'-[[(Propane-1,3-diyl)dioxy]bis[(11S,11aS,2R)-10-(2,2,2-trichloroethoxycarbonyl)-11-hydroxy-7-methoxy-2-oxyacetyl-1,2,3,10,11,11a-hexahydro-5H-pyrrolo[2,1-c][1,4]benzodiazepin-5-one]] (9)

TEMPO (0.69 g, 4.42 mmol, 0.4 eq) and BAIB (15.7 g, 48.7 mmol, 4.4 eq) were added to a stirred solution of diol 8 (11.5 g, 11.1 mmol) in DCM (150 mL). The reaction mixture was allowed to stir for 2 h and diluted with DCM (400 mL), washed with saturated NaHSO$_3$ (500 mL), saturated NaHCO$_3$ (500 mL), brine (200 mL) and dried (MgSO$_4$). Filtration and evaporation of the solvent afforded the crude product which was purified by flash column chromatography (99.9:0.1 v/v CHCl$_3$/MeOH then gradient to 99.7:0.3 v/v CHCl$_3$/MeOH) to provide the product 9 as a light yellow glass (4.43 g, 39%): $^1$H NMR (400 MHz, CDCl$_3$) δ 7.28 (s, 2H, H6), 6.84 (s, 2H, H9), 5.68 (d, 2H, J=9.1 Hz, H11), 5.37-5.35 (m, 2H, H2), 5.18 (d, 2H, J=12.0 Hz, Troc CH$_2$), 4.32-4.21 (m, 6H, OCH$_2$CH$_2$CH$_2$O, Troc CH$_2$), 4.03 (dd, 2H, J=13.2, 2.6 Hz, H3), 3.92 (s, 6H, OCH$_3$×2), 3.39-3.69 (m, 4H, H3 and H11), 2.39-2.35 (m, 6H, OCH$_2$CH$_2$CH$_2$O and H1), 2.03 (s, 6H, CH$_3$CO$_2$×2); $^{13}$C NMR (100.6 MHz, CDCl$_3$) δ 170.4 (CH$_3$CO$_2$), 167.4 (C$_{quat}$), 154.3 (C$_{quat}$), 150.5 (C$_{quat}$), 149.1 (C$_{quat}$), 127.4 (C$_{quat}$), 124.9 (C$_{quat}$), 114.1 (C9), 110.9 (C6), 95.0 (Troc CCl$_3$), 87.5 (C11), 75.0 (Troc CH$_2$), 71.4 (C2), 65.5 (OCH$_2$CH$_2$CH$_2$O), 58.4 (C11a), 56.1 (OCH$_3$), 51.1 (C3), 35.8 (C1), 29.1 (OCH$_2$CH$_2$CH$_2$O), 21.0 (CH$_3$CO$_2$); MS (ES), m/z (relative intensity) 1058 ([M+Na]$^{+}$, 100).

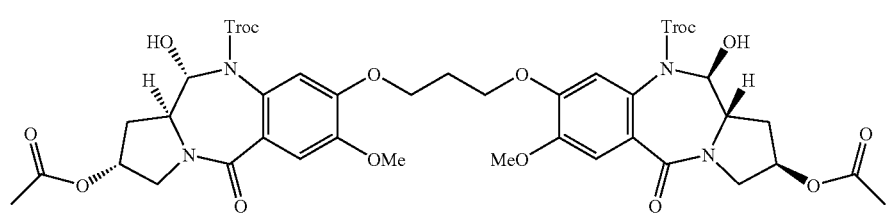

1,1'-[[(Propane-1,3-diyl)dioxy]bis[(11S,11aS,2R)-10-(2,2,2-trichloroethoxycarbonyl)-11-(tert-butyldimethylsilyloxy)-7-methoxy-2-oxyacetyl-1,2,3,10,11,11a-hexahydro-5H-pyrrolo[2,1-c][1,4]benzodiazepin-5-one]] (10)

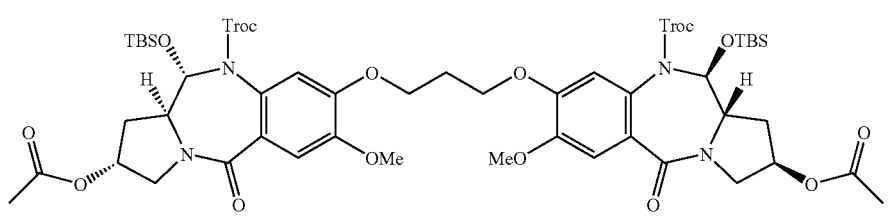

TBSOTf (2.70 mL, 3.10 g, 11.7 mmol, 3.0 eq) was added to a stirred solution of bis-alcohol 9 (4.05 g, 3.91 mmol) and 2,6-lutidine (1.82 mL, 1.68 g, 15.6 mmol, 4.0 eq) in DCM (50 mL). The reaction mixture was allowed to stir for 2.5 h and diluted with DCM (150 mL), washed with saturated $CuSO_4$ (2×100 mL), saturated $NaHCO_3$ (100 mL), brine (200 mL) and dried ($MgSO_4$). Filtration and evaporation of the solvent afforded the crude product which was purified by flash column chromatography (99.9:0.1 v/v $CHCl_3$/MeOH) to provide the product 10 as a white glass (5.05 g, >100%): $^1$H NMR (400 MHz, $CDCl_3$) δ 7.05 (s, 2H, H6), 6.52 (s, 2H, H9), 5.53 (d, 2H, J=9.0 Hz, H11), 5.14 (br s, 2H, H2), 4.99 (d, 2H, J=12.0 Hz, Troc $CH_2$), 4.06-3.87 (m, 8H, $OCH_2CH_2CH_2O$, Troc $CH_2$ and H11a), 3.71 (s, 6H, $OCH_3$×2), 3.48-3.43 (m, 4H, H3), 2.21-2.11 (m, 4H, $OCH_2CH_2CH_2O$ and H1), 2.03-1.96 (m, 2H, H1), 1.81 (s, 6H, $CH_3CO_2$×2), 0.63 (s, 18H, TBS $CH_3$×6), 0.00 (s×2, 12H, TBS $CH_3$×4); $^{13}$C NMR (100.6 MHz, $CDCl_3$) δ 170.3 ($CH_3CO_2$), 167.9 ($C_{quat}$), 153.6 ($C_{quat}$), 150.4 ($C_{quat}$), 149.2 ($C_{quat}$), 127.9 ($C_{quat}$), 125.5 ($C_{quat}$), 113.9 (C9), 110.7 (C6), 95.2 (Troc $CCl_3$), 88.2 (C11), 74.7 (Troc $CH_2$), 71.7 (C2), 65.0 ($OCH_2CH_2CH_2O$), 60.5 (C11a), 56.1 ($OCH_3$), 51.2 (C3), 36.2 (C1), 28.8 ($OCH_2CH_2CH_2O$), 25.6 (TBS $CH_3$), 21.0 ($CH_3CO_2$), 17.8 (TBS $C_{quat}$), 14.2 and 14.1 (TBS $CH_3$); MS (ES), m/z (relative intensity) 1285 ([M+21]$^{+\cdot}$, 100), 1265 ([M+H]$^{+\cdot}$, 75).

1,1'-[[(Propane-1,3-diyl)dioxy]bis[(11S,11aS,2R)-10-(2,2,2-trichloroethoxycarbonyl)-11-(tert-butyldimethylsilyloxy)-7-methoxy-2-hydroxy-1,2,3,10,11,11a-hexahydro-5H-pyrrolo[2,1-c][1,4]benzodiazepin-5-one]] (11)

A solution of $K_2CO_3$ (93 mg, 0.67 mmol, 5.0 eq) in $H_2O$ (2 mL) was added dropwise to a stirred solution of acetate 10 (170 mg, 0.13 mmol) in MeOH (3 mL). The initial colorless solution eventually turned yellow and the formation of a white precipitate was observed. The reaction mixture was allowed to stir for 16 h when TLC (95:5 v/v $CHCl_3$/MeOH) showed the complete consumption of the starting material. Excess solvent was removed by rotary evaporation and the mixture was carefully neutralized with 1N HCl to pH 7. The resulting mixture was extracted with EtOAc (3×25 mL) and the combined organic layers were then washed with brine (40 mL) and dried ($MgSO_4$). Filtration and removal of the solvent afforded the product 11 as a white glass (151 mg, 95%): $^1$H NMR (400 MHz, $CDCl_3$) δ 6.94 (s, 2H, H6), 6.52 (s, 2H, H9), 5.53 (d, 2H, J=9.0 Hz, H11), 5.00 (d, 2H, J=12.0 Hz, Troc $CH_2$), 4.36-4.35 (m, 2H, H2), 4.06-3.82 (m, 8H, $OCH_2CH_2CH_2O$, Troc $CH_2$ and H3), 3.61 (s, 6H, $OCH_3$×2), 3.54-3.48 (m, 2H, H11a), 3.39-3.34 (m, 2H, H3), 2.96 and 2.95 (br s×2, 2H, OH×2), 2.21-2.20 (m, 2H, $OCH_2CH_2CH_2O$), 2.19-2.08 (m, 2H, H1), 1.90-1.74 (m, 2H, H1), 0.64 (s, 18H, TBS $CH_3$×6), 0.00 (s, 12H, TBS $CH_3$×4); $^{13}$C NMR (100.6 MHz, $CDCl_3$) δ 168.5 ($C_{quat}$), 153.6 ($C_{quat}$), 150.3 ($C_{quat}$), 149.1 ($C_{quat}$), 127.9 ($C_{quat}$), 125.4 ($C_{quat}$), 113.9 (C9), 110.7 (C6), 95.2 (Troc $CCl_3$), 88.3 (C11), 74.7 (Troc $CH_2$), 69.4 (C2), 65.0 ($OCH_2CH_2CH_2O$), 60.9 (C11a), 55.9 ($OCH_3$), 54.1 ($C_3$), 38.8 (C1), 28.9 ($OCH_2CH_2CH_2O$), 25.6 (TBS $CH_3$), 17.8 (TBS $C_{quat}$); MS (ES), m/z (relative intensity) 1196 ([M+16]$^{+\cdot}$, 100), 1181 ([M+H]$^{+\cdot}$, 82).

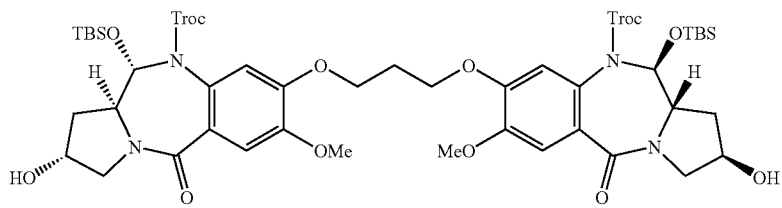

1,1'-[[(Propane-1,3-diyl)dioxy]bis[(11S,11aS)-10-(2,2,2-trichloroethoxycarbonyl)-11-(tert-butyldimethylsilyloxy)-7-methoxy-2-oxo-1,2,3,10,11,11a-hexahydro-5H-pyrrolo[2,1-c][1,4]benzodiazepin-5-one]] (12)

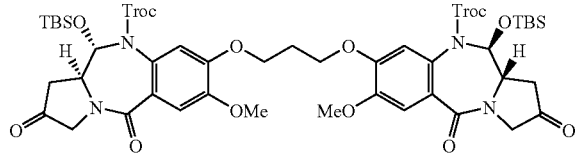

A solution of anhydrous DMSO (0.82 mL, 0.90 g, 11.5 mmol, 6.0 eq) in dry DCM (20 mL) was added dropwise to a stirred solution of oxalyl chloride (2.88 mL of a 2 M solution in DAM, 5.76 mmol, 3.0 eq) under a nitrogen atmosphere at −60° C. (liq $N_2$/CHCl$_3$). After stirring at −55° C. for 1.5 h, a solution of the substrate 11 (2.26 g, 1.92 mmol) in dry DCM (30 mL) was added dropwise to the reaction mixture, which was then stirred for a further 2 h at −45° C. A solution of TEA (10.8 mL, 7.82 g; 71.7 mmol, 4.2 eq) in dry DCM (90 mL) was added dropwise to the mixture and stirred for a further 30 min. The reaction mixture was left to warm to 0° C., washed with cold 1 N HCl (2×50 mL), H$_2$O (50 mL), brine (50 mL) and dried (MgSO$_4$). Filtration and evaporation of the solvent in vacuo afforded the crude product which was purified by flash column chromatography (70:30 v/v hexane/EtOAc then gradient to 40:60 v/v hexane/EtOAc) to afford carbinolamine 12 as a white glass (1.62 g, 72%): $^1$H NMR (400 MHz, CDCl$_3$) δ 7.02 (s, 2H, H6), 6.54 (s, 2H, H9), 5.59 (d, 2H, J=9.2 Hz, H11), 4.98 (d, 2H, J=12.0 Hz, Troc CH$_2$), 4.09-3.86 (m, 8H, OCH$_2$CH$_2$CH$_2$O, Troc CH$_2$ and H3), 3.75-3.66 (m, 10H, OCH$_3$×2, H11a, and H3), 2.72 (dd, 2H, J=10.2, 19.6 Hz, H1), 2.82 (dd, 2H, J=2.6, 19.6 Hz, H1), 2.22-2.19 (m, 2H, OCH$_2$CH$_2$CH$_2$O), 0.63 (s, 18H, TBS CH$_3$×6), 0.00 (s×2, 12H, TBS CH$_3$×4); $^{13}$C NMR (100.6 MHz, CDCl$_3$) δ 207.7 (C2), 168.0 (C$_{quat}$), 153.7 (C$_{quat}$), 150.7 (C$_{quat}$), 149.4 (C$_{quat}$), 127.8 (C$_{quat}$), 124.6 (C$_{quat}$), 114.0 (C9), 110.6 (C6), 95.1 (Troc CCl$_3$), 87.4 (C11), 74.8 (Troc CH$_2$), 65.0 (OCH$_2$CH$_2$CH$_2$O), 58.9 (C11a), 56.1 (OCH$_3$), 53.0 (C3), 40.3 (C1), 28.8 (OCH$_2$CH$_2$CH$_2$O), 25.6 (TBS CH$_3$), 17.8 (TBS C$_{quat}$); MS (ES), m/z (relative intensity) 1224 ([M+48]$^+$, 100), 1210 ([M+34]$^+$, 60), 1199 ([M+Na]$^+$, 35), 1192 ([M+16]$^+$, 40), 1176 (M$^+$, 18).

1,1'-[[(Propane-1,3-diyl)dioxy]bis[(11S,11aS)-10-(2,2,2-trichloroethoxycarbonyl)-11-(tert-butyldimethylsilyloxy)-7-methoxy-2-[[(trifluoromethyl)sulfonyl]oxy]-1,10,11,11a-tetrahydro-5H-pyrrolo[2,1-c][1,4]benzodiazepin-5-one]] (13)

Anhydrous triflic anhydride (3.09 mL, 5.19 g, 18.4 mmol, 22 eq) taken from a freshly opened ampule was added rapidly in one portion to a vigorously stirred solution of ketone 12 (0.98 g, 0.84 mmol) and anhydrous pyridine (1.49 mL, 1.46 g, 18.4 mmol, 22 eq) in dry DAM (50 mL) at room temperature under a nitrogen atmosphere. The initial precipitate dissolved gradually and the solution eventually turned a dark red colour. The reaction mixture was allowed to stir for 4.5 h when TLC (80:20 v/v EtOAc/hexane) revealed the complete consumption of the starting material. The mixture was poured into cold saturated NaHCO$_3$ (60 mL) and extracted with DCM (3×80 mL). The combined organic layers were then washed with saturated CuSO$_4$ (2×125 mL), brine (125 mL) and dried (MgSO$_4$). Filtration and evaporation of the solvent afforded the crude product which was purified by flash column chromatography (80:20 v/v hexane/EtOAc) to afford triflate 13 as a light yellow glass (0.74 mg, 61%): [α]$^{25}_D$=+46.0° (c=0.33, CHCl$_3$); $^1$H NMR (400 MHz, CDCl$_3$) δ 7.23 (s, 2H, H6), 7.19 (s, 2H, H3), 6.77 (s, 2H, H9), 5.94 (d, 2H, J=8.9 Hz, H11), 5.23 (d, 2H, J=12.0 Hz, Troc CH$_2$), 4.31-4.28 (m, 2H, OCH$_2$CH$_2$CH$_2$O), 4.18 (d, 2H, J=12.2 Hz, Troc CH$_2$), 4.15-4.13 (m, 2H, OCH$_2$CH$_2$CH$_2$O), 3.95-3.91 (m, 8H, OCH$_3$×2, H11a), 3.35 (dd, 2H, J=11.0, 16.6 Hz, H1), 2.84 (d, 2H, J=16.6 Hz, H1), 2.46-2.44 (m, 2H, OCH$_2$CH$_2$CH$_2$O), 0.89 (s, 18H, TBS CH$_3$×6), 0.29 and 0.26 (s×2, 12H, TBS CH$_3$×4); $^{13}$C NMR (100.6 MHz, CDCl$_3$) δ 164.9 (C$_{quat}$), 153.6 (C$_{quat}$), 151.0 (C$_{quat}$), 149.5 (C$_{quat}$), 136.0 (C$_{quat}$), 127.7 (C$_{quat}$), 123.9 (C$_{quat}$), 121.0 (C3), 114.0 (C9), 110.9 (C6), 95.1 (Troc CCl$_3$), 86.3 (C11), 74.8 (Troc CH$_2$), 65.0 (OCH$_2$CH$_2$CH$_2$O), 60.6 (C11a), 56.2 (OCH$_3$), 34.4 (C1), 28.8 (OCH$_2$CH$_2$CH$_2$O), 25.6 (TBS CH$_3$), 17.8 (TBS C$_{quat}$); IR (CHCl$_3$) 3020, 2957, 2860, 1725, 1674, 1651, 1604, 1516, 1466, 1454, 1431, 1409, 1329, 1312, 1274, 1216, 1138, 1113, 1083, 1042, 1006, 900, 840, 757, 668, 646, 610 cm$^{-1}$; MS (ES), m/z (relative intensity) 1461 ([M+21]$^+$, 100), 1440 (M$^+$, 55).

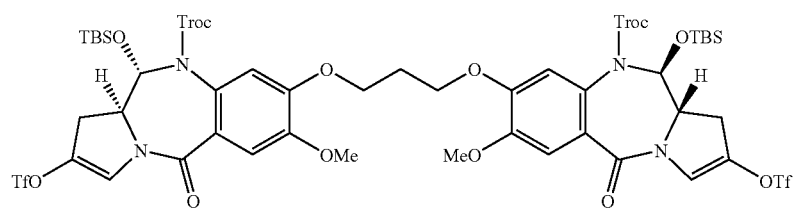

Example 2

1,1'-[[(Propane-1,3-diyl)dioxy]bis[(11aS)-7-methoxy-2-[(N,N-dimethylaminocarbonyl)vinyl]-1,11a-dihydro-5H-pyrrolo[2,1-c][1,4]benzodiazepine-5-one]] (ZC-204)

1,1'-[[(Propane-1,3-diyl)dioxy]bis[(11S,11aS)-10-(2,2,2-trichloroethoxycarbonyl)-11-(tert-butyldimethylsilyloxy)-7-methoxy-2-[(N,N-dimethylaminocarbonyl)vinyl]-1,10,11,11a-tetrahydro-5H-pyrrolo[2,1-c][1,4]benzodiazepin-5-one]] (14)

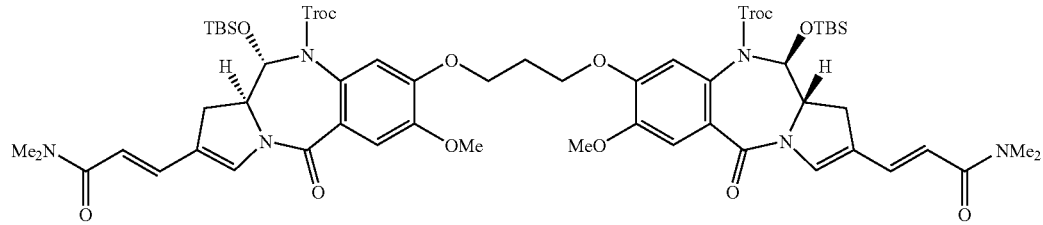

14

A mixture of triflate 13 (732 mg, 1.22 mmol), N,N-dimethylacrylamide (0.14 mL, 134 mg, 1.35 mmol, 5.0 eq), DABCO (152 mg, 1.35 mmol, 5.0 eq), $(CH_3CN)_2PdCl_2$ (14 mg, 0.05 mmol, 0.2 eq) and MeOH (15 mL) was stirred at 55-65° C. for 16 h. The reaction was worked-up by pouring the mixture into $CHCl_3$ (20 mL) and aqueous $NaHCO_3$ (20 mL). The aqueous layer was extracted with $CHCl_3$ (3×20 mL) and the $CHCl_3$ extracts were combined, washed with $H_2O$ (50 mL), brine (50 mL) and dried ($MgSO_4$). Filtration and evaporation of solvent gave the crude product as a dark brown glass. The residue was purified by flash column chromatography (99.9:0.1 v/v $CHCl_3$/MeOH then gradient to 99.2:0.8 v/v $CHCl_3$/MeOH) to give the coupled product 14 as a light yellow glass (80 mg, 22%): $[\alpha]^{26}_D = +87.2°$ (c=0.11, $CHCl_3$); $^1H$ NMR (250 MHz, $CDCl_3$) δ 7.51 (d, 2H, J=15.0 Hz, H12), 7.32 (s, 2H, H3), 7.28 (s, 2H, H6), 6.79 (s, 2H, H9), 6.10 (d, 2H, J=15.0 Hz, H13), 5.88 (d, 2H, J=8.8 Hz, H11), 5.23 (d, 2H, J=12.0 Hz, Troc $CH_2$), 4.33-4.28 (m, 2H, $OCH_2CH_2CH_2O$), 4.18 (d, 1H, J=12.2 Hz, Troc $CH_2$), 4.18-4.14 (m, 2H, $OCH_2CH_2CH_2O$), 3.98-3.95 (m, 8H, H11a and $OCH_3$×2), 3.17-3.06 (m, 8H, H1 and $NCH_3$×2), 2.65 (d, 1H, J=16.2 Hz, H1), 2.47-2.44 (m, 2H, $OCH_2CH_2CH_2O$), 0.92 (s, 18H, TBS $CH_3$×6), 0.29 and 0.27 (s×2, 12H, TBS $CH_3$×4); $^{13}C$ NMR (62.9 MHz, $CDCl_3$) δ 166.5 ($CONMe_2$), 132.5 (C12), 132.6 (C3), 116.8 (C13), 114.0 (C9), 110.8 (C6), 95.2 (Troc $CCl_3$), 86.9 (C11), 74.8 (Troc $CH_2$), 65.0 ($OCH_2CH_2CH_2O$), 61.9 (C11a), 56.2 ($OCH_3$), 33.5 (C1), 28.8 ($OCH_2CH_2CH_2O$), 25.6 (TBS $CH_3$), 17.9 (TBS $C_{quat}$); MS (ES), m/z (relative intensity) 1337 ([M−H]⁺·, 100), 1327 (27), 1316 (34).

1,1'-[[(Propane-1,3-diyl)dioxy]bis[(11aS)-7-methoxy-2-[(N,N-dimethylaminocarbonyl)vinyl]-1,11a-dihydro-5H-pyrrolo[2,1-c][1,4]benzodiazepine-5-one]] (ZC-204)

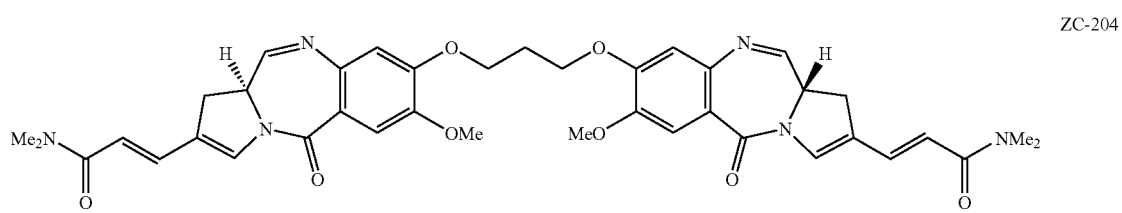

ZC-204

10% Cd/Pd couple (120 mg, 0.99 mmol, 16.5 eq) was added to a rapidly stirring mixture of 14 (79 mg, 0.06 mmol), THF (1.5 mL) and 1 N $NH_4OAc$ (1.5 mL). The reaction mixture was allowed to stir for 3.5 h. The solids were filtered and rinsed with $H_2O$ and $CHCl_3$. The aqueous layer was extracted with $CHCl_3$ (3×20 mL), and the organic extracts were combined, washed with brine (50 mL) and dried ($MgSO_4$). Filtration and evaporation of solvent left a yellow solid which was purified by flash column chromatography (99.9:0.1 v/v $CHCl_3$/MeOH then gradient to 95:5 v/v $CHCl_3$/MeOH) to afford ZC-204 as a yellow glass (13.4 mg, 31%): $[\alpha]^{25}_D = +235.7°$ (c=0.07, $CHCl_3$); $^1H$ NMR (400 MHz, $CDCl_3$) δ 7.88 (d, 2H, J=3.9 Hz, H11), 7.54 (d, 2H, J=15.1 Hz, H12), 7.51 (s, 2H, H3), 7.34 (s, 2H, H6), 6.88 (s, 2H, H9), 6.18 (d, 2H, J=15.0 Hz, H13), 4.43-4.27 (m, 6H, $OCH_2CH_2CH_2O$ and H11a), 3.95 (s, 6H, $OCH_3$×2), 3.41-3.34 (m, 2H, H1), 3.23-3.04 (m, 14H, H1 and $NCH_3$×4), 2.47-2.44 (m, 2H, $OCH_2CH_2CH_2O$); $^{13}C$ NMR (62.9 MHz, $CDCl_3$) δ 166.4 ($CONMe_2$), 162.1 (C11), 161.7 ($C_{quat}$), 151.5 ($C_{quat}$), 148.2 ($C_{quat}$), 140.4 ($C_{quat}$), 135.2 (C12), 132.2 (C3), 121.8 ($C_{quat}$), 118.6 ($C_{quat}$), 117.0 (C13), 112.0 (C9), 111.3 (C6), 65.4 ($OCH_2CH_2CH_2O$), 56.2 ($OCH_3$), 54.2 (C11a), 37.4 and 35.9 ($NCH_3$), 33.8 ($C1_{28.8}$ ($OCH_2CH_2CH_2O$); MS (ES), m/z (relative intensity) 741 ([M+$H_2O$]⁺·, 25), 723 (M⁺·, 62).

Example 3

1,1'-[[(Propane-1,3-diyl)dioxy]bis[(11aS)-7-methoxy-2-(p-methoxybenzene)-1,11a-dihydro-5H-pyrrolo[2,1-c][1,4]benzodiazepine-5-one]] (ZC-207)

1,1'-[[(Propane-1,3-diyl)dioxy]bis[(11S,11aS)-10-(2,2,2-trichloroethoxycarbonyl)-11-(tert-butyldimethylsilyloxy)-7-methoxy-2-(p-methoxybenzene)-1,10,11,11a-tetrahydro-5H-pyrrolo[2,1-c][1,4]benzodiazepin-5-one]] (15)

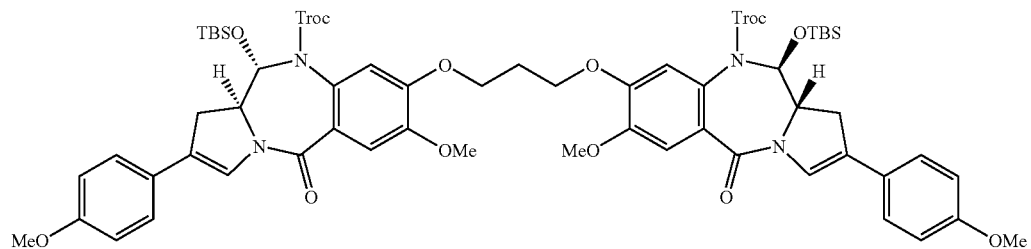

A solution of TEA (0.20 mL, 148 mg, 1.46 mmol, 6.0 eq) in $H_2O$ (1.5 mL) and EtOH (10 mL) was added to a solution of triflate 13 (350 mg, 0.24 mmol) in toluene (10 mL) at room temperature. To this mixture 4-methoxybenzeneboronic acid (96 mg, 0.63 mmol, 2.6 eq) and $Pd(PPh_3)_4$ (11 mg, 9 µmol, 0.04 eq) were added. The reaction mixture was allowed to stir for 15 min when TLC (80:20 v/v EtOAc/hexane) revealed the complete consumption of the starting material. Excess solvent was removed and the residue was dissolved in EtOAc (25 mL), washed with $H_2O$ (15 mL), brine (15 mL) and dried ($MgSO_4$). Filtration and evaporation of solvent afforded the crude product which was purified by flash column chromatography (80:20 v/v hexane/EtOAc then gradient to 50:50 v/v hexane/EtOAc) to afford 15 as a yellow glass (286 mg, 87%): $^1H$ NMR (400 MHz, $CDCl_3$) δ 7.38 (s, 2H, H3), 7.32-7.28 (m, 6H, H6 and H13), 6.92 (d, 4H, J=8.7 Hz, H14), 6.81 (s, 2H, H9), 5.93 (d, 2H, J=8.8 Hz, H11), 5.24 (d, 2H, J=12.0 Hz, Troc $CH_2$), 4.34-4.29 (m, 2H, $OCH_2CH_2CH_2O$), 4.20-4.11 (m, 4H, Troc $CH_2$ and $OCH_2CH_2CH_2O$), 4.00-3.96 (m, 8H, H11a and $OCH_3×2$), 3.84 (s, 6H, $OCH_3×2$), 3.36 (dd, 2H, J=10.8, 16.6 Hz, H1), 2.85 (d, 2H, J=16.5 Hz, H1), 2.48-2.45 (m, 2H, $OCH_2CH_2CH_2O$), 0.93 (s, 18H, TBS $CH_3×6$), 0.30 and 0.27 (s×2, 12H, TBS $CH_3×4$); $^{13}C$ NMR (100.6 MHz, $CDCl_3$) δ 162.5 ($C_{quat}$), 161.3 ($C_{quat}$), 159.2 ($C_{quat}$), 151.1 ($C_{quat}$), 148.1 ($C_{quat}$), 140.3 ($C_{quat}$), 126.2 (C13), 126.0 ($C_{quat}$), 123.2 ($C_{quat}$), 121.9 (C3), 119.3 ($C_{quat}$), 114.3 (C6), 111.9 (C14), 111.2 (C9), 95.2 (Troc $CCl_3$), 87.3 (C11), 74.8 (Troc $CH_2$), 65.0 ($OCH_2CH_2CH_2O$), 61.5 (C11a), 56.1 and 55.3 ($OCH_3$), 35.3 (C1), 28.8 ($OCH_2CH_2CH_2O$), 25.7 (TBS $CH_3$), 17.9 (TBS $C_{quat}$); MS (ES), m/z (relative intensity) 1357 ($M^{+\cdot}$, 63), 1114 (48), 955 (59), 919 (78).

1,1'-[[(Propane-1,3-diyl)dioxy]bis[(11aS)-7-methoxy-2-(p-methoxybenzene)-1,11a-dihydro-5H-pyrrolo[2,1-c][1,4]benzodiazepine-5-one]] (ZC-207)

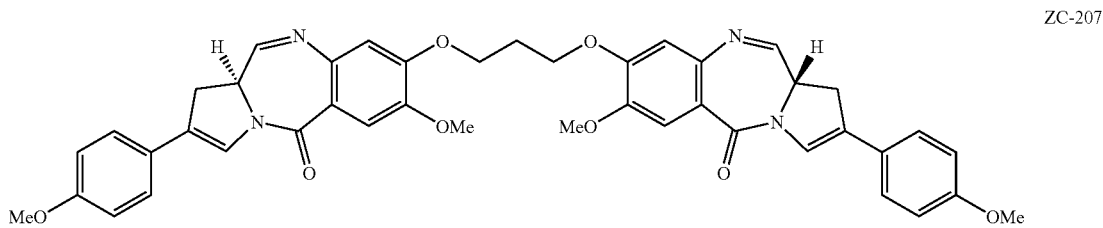

10% Cd/Pd couple (461 mg, 3.73 mmol, 20 eq) was added to a rapidly stirring mixture of 15 (253 mg, 0.19 mmol), THF (5 mL) and 1 N $NH_4OAc$ (5 mL). The reaction mixture was allowed to stir for 1.5 h when TLC showed the complete consumption of the starting material. The solids were filtered and rinsed with $H_2O$ and DAM. The aqueous layer was extracted with DCM (3×30 mL) and the organic extracts were combined, washed with brine (50 mL) and dried ($MgSO_4$). Filtration and evaporation of solvent afforded the crude product which was purified by flash column chromatography (99.9:0.1 v/v $CHCl_3$/MeOH then gradient to 95:5 v/v $CHCl_3$/MeOH) to afford ZC-207 as a yellow glass (132 mg, 96%): $[\alpha]^{20}_D$=+880.0° (c=0.22, $CHCl_3$); $^1H$ NMR (400 MHz, $CDCl_3$) δ 7.79 (d, 2H, J=3.9 Hz, H11), 7.44 (s, 2H, H6), 7.30 (s, 2H, H3), 7.24 (d, 4H, J=8.7 Hz, H13), 6.81 (d, 4H, J=8.7 Hz, H14), 6.79 (s, 2H, H9), 4.30-4.18 (m, 6H, $OCH_2CH_2CH_2O$ and H11a), 3.86 (s, 6H, $OCH_3×2$), 3.74 (s, 6H, $OCH_3×2$), 3.48 (dd, 2H, J=11.8, 16.2 Hz, H1), 2.85 (d, 2H, J=16.2 Hz, H1), 2.38-2.32 (m, 2H, $OCH_2CH_2CH_2O$); $^{13}C$ NMR (62.9 MHz, $CDCl_3$) δ 162.5 (C11), 161.3 ($C_{quat}$), 159.2 ($C_{quat}$), 151.1 ($C_{quat}$), 148.1 ($C_{quat}$), 140.3 ($C_{quat}$), 126.2 (C13), 126.0 ($C_{quat}$), 123.2 ($C_{quat}$), 121.9 (C3), 114.3 (C14), 111.9 (C9), 111.2 (C6), 65.4 ($OCH_2CH_2CH_2O$), 56.2 and 55.3 ($OCH_3$), 53.8 (C11a), 35.6 (C1), 28.9 ($OCH_2CH_2CH_2O$); MS (ES), m/z (relative intensity) 741 ($M^{+\cdot}$, 43), 660 (71).

Example 4

1,1'-[[(Propane-1,3-diyl)dioxy]bis[(11aS)-7-methoxy-2-(1-propenyl)-1,11a-dihydro-5H-pyrrolo[2,1-c][1,4]benzodiazepine-5-one]] (ZC-211)

1,1'-[[(Propane-1,3-diyl)dioxy]bis[(11S,11aS)-10-(2,2,2-trichloroethoxycarbonyl)-11-(tert-butyldimethylsilyloxy)-7-methoxy-2-(1-propenyl)-1,10,11,11a-tetrahydro-5H-pyrrolo[2,1-c][1,4]benzodiazepin-5-one]] (16)

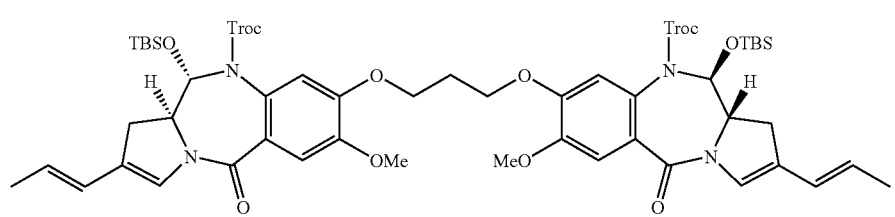

16

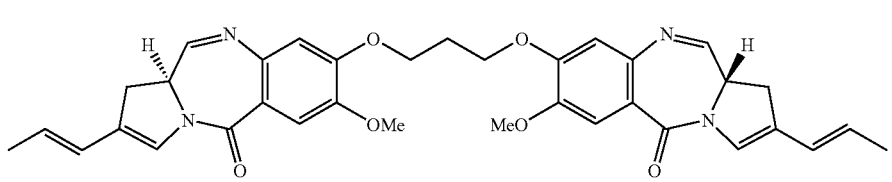

ZC-211

A solution of TEA (0.11 mL, 81 mg, 0.80 mmol, 6.0 eq) in $H_2O$ (3 mL) and EtOH (10 mL) was added to a solution of triflate 13 (192 mg, 0.13 mmol) in toluene (5 mL) at room temperature. To this mixture trans-propenylboronic acid (30 mg, 0.35 mmol, 2.6 eq) and $Pd(PPh_3)_4$ (6 mg, 5 μmol, 0.04 eq) were added. The reaction mixture was heated at 76° C. for 2 h when TLC (50:50 v/v EtOAc/hexane) revealed the complete consumption of the starting material. Excess solvent was removed and the residue was dissolved in EtOAc (15 mL), washed with $H_2O$ (10 mL), brine (10 mL) and dried ($MgSO_4$). Filtration and evaporation of solvent afforded the crude product which was purified by flash column chromatography (80:20 v/v hexane/EtOAc) to afford 16 as a light yellow glass (40 mg, 25%): $[\alpha]^{20}_D = +75.0°$ (c=0.20, $CHCl_3$); $^1$H NMR (400 MHz, $CDCl_3$) δ 7.28 (s, 2H, H6), 6.90 (s, 2H, H3), 6.78 (s, 2H, H9), 6.26 (d, 2H, J=14.8 Hz, H12), 5.85 (d, 2H, J=8.8 Hz, H11), 5.54 (d, J=6.8, 15.4 Hz, 2H, H13), 5.23 (d, 2H, J=12.0 Hz, Troc $CH_2$), 4.32-4.26 (m, 2H, $OCH_2CH_2CH_2O$), 4.18-4.11 (m, 4H, Troc $CH_2$ and $OCH_2CH_2CH_2O$), 3.94 (s, 6H, $OCH_3×2$), 3.89-3.83 (m, 2H, H11a), 3.07 (dd, 2H, J=10.6, 15.9 Hz, H1), 2.60 (d, 2H, J=16.3 Hz, H1), 2.46-2.43 (m, 2H, $OCH_2CH_2CH_2O$), 1.85 (d, 6H, J=6.6 Hz, H14), 0.90 (s, 18H, TBS $CH_3×6$), 0.28 and 0.25 (s×2, 12H, TBS $CH_3×4$); $^{13}$C NMR (100.6 MHz, $CDCl_3$) δ 163.6 ($C_{quat}$), 153.6 ($C_{quat}$), 150.4 ($C_{quat}$), 149.2 ($C_{quat}$), 127.7 ($C_{quat}$), 126.4 (C13), 125.6 ($C_{quat}$), 124.7 (C12 and C3), 123.5 ($C_{quat}$), 114.0 (C9), 110.7 (C6), 95.2 (Troc $CCl_3$), 87.2 (C11), 74.7 (Troc $CH_2$), 65.0 ($OCH_2CH_2CH_2O$), 61.4 (C11a), 56.1 ($OCH_3$), 33.9 (C1), 28.8 ($OCH_2CH_2CH_2O$), 25.6 (TBS $CH_3$), 18.4 (C14), 17.9 (TBS $C_{quat}$); MS (ES), m/z (relative intensity) 1246 ($[M+22]^{+·}$, 100), 1226 ($[M+2]^{+·}$, 88).

1,1'-[[(Propane-1,3-diyl)dioxy]bis[(11aS)-7-methoxy-2-(1-propenyl)-1,11a-dihydro-5H-pyrrolo[2,1-c][1,4]benzodiazepine-5-one]] (ZC-211)

10% Cd/Pd couple (81 mg, 0.65 mmol, 20 eq) was added to a rapidly stirring mixture of 16 (40 mg, 0.03 mmol), THF (1 mL) and 1 N $NH_4OAc$ (1 mL). The reaction mixture was allowed to stir for 1 h when TLC showed the complete consumption of the starting material. The solids were filtered and rinsed with $H_2O$ and $CHCl_3$. The aqueous layer was extracted with $CHCl_3$ (3×5 mL) and the organic extracts were combined, washed with $H_2O$ (10 mL), brine (10 mL) and dried ($MgSO_4$). Filtration and evaporation of solvent afforded the crude product which was purified by flash column chromatography (99.8:0.2 v/v $CHCl_3$/MeOH then gradient to 97:3 v/v $CHCl_3$/MeOH) to afford ZC-211 as a yellow glass (14.7 mg, 74%): $[\alpha]^{20}_D = +1102.0°$ (c=0.15, $CHCl_3$); $^1$H NMR (400 MHz, $CDCl_3$) δ 7.74 (d, 2H, J=3.8 Hz, H11), 7.42 (s, 2H, H6), 6.84 (s, 2H, H3), 6.77 (s, 2H, H9), 6.19 (d, 2H, J=15.5 Hz, H12), 5.52 (dd, J=6.8, 15.4 Hz, 2H, H13), 4.27-4.16 (m, 6H, $OCH_2CH_2CH_2O$ and H11a), 3.84 (s, 6H, $OCH_3×2$), 3.22 (dd, 2H, J=11.5, 16.1 Hz, H1), 3.03 (dd, 2H, J=4.8, 16.2 Hz, H1), 2.38-2.32 (m, 2H, $OCH_2CH_2CH_2O$), 1.77 (d, 6H, J=6.6 Hz, H14); $^{13}$C NMR (100.6 MHz, $CDCl_3$) δ 162.6 (C11), 161.2 ($C_{quat}$), 151.1 ($C_{quat}$), 148.1 ($C_{quat}$), 140.3 ($C_{quat}$), 127.7 ($C_{quat}$), 126.9 (C13), 124.4 (C12 and C3), 123.9 ($C_{quat}$), 119.3 ($C_{quat}$), 111.9 (C6), 111.2 (C9), 65.4 ($OCH_2CH_2CH_2O$), 56.2 ($OCH_3$), 53.8 (C11a), 34.2 (C1), 28.8 ($OCH_2CH_2CH_2O$), 18.5 (C14); MS (ES), m/z (relative intensity) 609 ($M^{+·}$, 100).

Example 5

1,1'-[[(Propane-1,3-diyl)dioxy]bis[(11aS)-7-methoxy-2-ethynylphenyl-1,11a-dihydro-5H-pyrrolo[2,1-c][1,4]benzodiazepine-5-one]] (ZC-209)

1,1'-[[(Propane-1,3-diyl)dioxy]bis[(11S,11aS)-10-(2,2,2-trichloroethoxycarbonyl)-11-(tert-butyldimethylsilyloxy)-7-methoxy-2-ethynylphenyl-1,10,11,11a-tetrahydro-5H-pyrrolo[2,1-c][1,4]benzodiazepin-5-one]] (17)

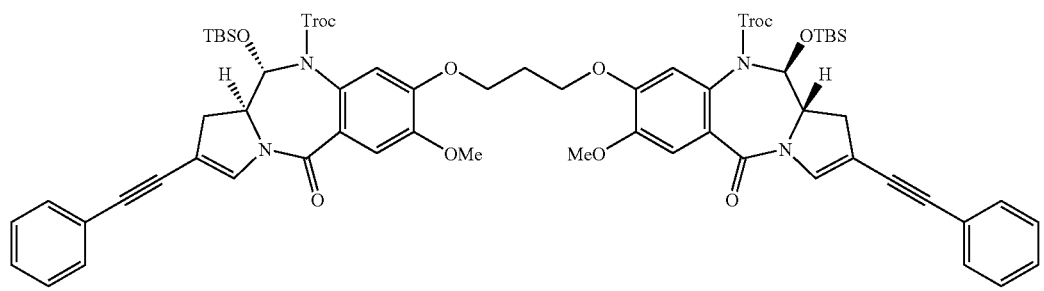

17

A catalytic amount of Pd(PPh$_3$)$_4$ was added to a stirred mixture of triflate 13 (193 mg, 0.13 mmol), LiCl (34 mg, 0.80 mmol, 6.0 eq) and tributyl(phenylethynyl)tin (0.14 mL, 157 mg, 0.40 mmol, 3.0 eq) in dry THF (5 mL). The reaction mixture was heated at reflux for 2.5 h when TLC showed the complete consumption of the starting material. After cooling to room temperature, excess solvent was removed and the residue was dissolved in DCM (20 mL), followed by washing with 10% NH$_4$OH (20 mL). The aqueous layer was extracted with DCM (3×20 mL), and the organic extracts were combined, washed with brine (50 mL) and dried (MgSO$_4$). Filtration and evaporation of solvent afforded the crude product which was purified by flash column chromatography (80:20 v/v hexane/EtOAc) to afford 17 as a yellow glass (162 mg, 90%): $^1$H NMR (400 MHz, CDCl$_3$) δ 7.40-7.37 (m, 4H, H15), 7.26-7.19 (m, 10H, H3, H6, H16 and H17), 6.70 (s, 2H, H9), 5.85 (d, 2H, J=8.8 Hz, H11), 5.15 (d, 2H, J=12.0 Hz, Troc CH$_2$), 4.24-4.19 (m, 2H, OCH$_2$CH$_2$CH$_2$O), 4.12-4.02 (m, 4H, Troc CH$_2$ and OCH$_2$CH$_2$CH$_2$O), 3.86-3.79 (m, 8H, OCH$_3$×2 and H11a), 3.15 (dd, 2H, J=10.8, 16.5 Hz, H1), 2.63 (d, 2H, J=16.5 Hz, H1), 2.37-2.35 (m, 2H, OCH$_2$CH$_2$CH$_2$O), 0.82 (s, 18H, TBS CH$_3$×6), 0.22 and 0.18 (s×2, 12H, TBS CH$_3$×4); $^{13}$C NMR (100.6 MHz, CDCl$_3$) δ 163.8 ($C_{quat}$), 153.6 ($C_{quat}$), 150.8 ($C_{quat}$), 149.3 ($C_{quat}$), 133.3 (C3), 131.4 (C15), 128.4 (C16 and C17), 127.8 ($C_{quat}$), 125.1 ($C_{quat}$), 123.0 ($C_{quat}$), 114.0 (C6), 110.0 (C9), 104.8 ($C_{quat}$), 95.2 (Troc CCl$_3$), 93.7 ($C_{alkyne}$), 86.9 (C11), 83.6 ($C_{alkyne}$), 74.8 (Troc CH$_2$), 66.0 (OCH$_2$CH$_2$CH$_2$O), 61.4 (C11a), 56.2 (OCH$_3$), 37.8 (C1), 28.8 (OCH$_2$CH$_2$CH$_2$O), 25.6 (TBS CH$_3$), 17.8 (TBS $C_{quat}$); MS (ES), m/z (relative intensity) 1344 (M$^{+·}$, 8), 625 (100).

1,1'-[[(Propane-1,3-diyl)dioxy]bis[(11aS)-7-methoxy-2-ethynylphenyl-1,11a-dihydro-5H-pyrrolo[2,1-c][1,4]benzodiazepine-5-one]] (ZC-209)

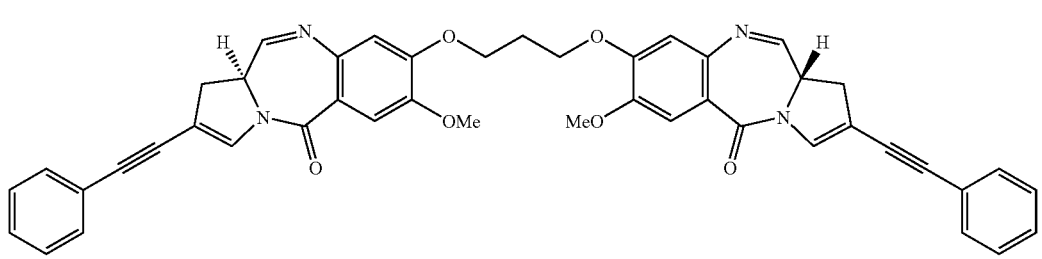

ZC-209

10% Cd/Pd couple (314 mg, 2.55 mmol, 20 eq) was added to a rapidly stirring mixture of 17 (162 mg, 0.13 mmol), THF (4 mL) and 1 N NH$_4$OAc (4 mL). The reaction mixture was allowed to stir for 45 min when TLC showed the complete consumption of the starting material. The solids were filtered and rinsed with H$_2$O and CHCl$_3$. The aqueous layer was extracted with CHCl$_3$ (3×25 mL) and the organic extracts were combined, washed with H$_2$O (50 mL), brine (50 mL)

and dried (MgSO$_4$). Filtration and evaporation of solvent afforded the crude product which was purified by flash column chromatography (99.8:0.2 v/v CHCl$_3$/MeOH then gradient to 97.5:2.5 v/v CHCl$_3$/MeOH) to afford ZC-209 as a yellow glass (33 mg, 38%): $^1$H NMR (400 MHz, CDCl$_3$) δ 7.79 (d, 2H, J=3.9 Hz, H11), 7.42 (s, 2H, H6), 7.39-7.37 (m, 4H, H15), 7.26-7.19 (m, 8H, H3, H16 and H17), 6.78 (s, 2H, H9), 4.30-4.19 (m, 6H, OCH$_2$CH$_2$CH$_2$O and H11a), 3.86 (s, 6H, OCH$_3$×2), 3.36 (dd, 2H, J=11.7, 16.4 Hz, H1), 3.18 (dd, 2H, J=5.4, 16.4 Hz, H1), 2.37-2.34 (m, 2H, OCH$_2$CH$_2$CH$_2$O); $^{13}$C NMR (100.6 MHz, CDCl$_3$) δ 162.0 (C11), 161.3 (C$_{quat}$), 151.4 (C$_{quat}$), 148.2 (C$_{quat}$), 140.3 (C$_{quat}$), 132.8 (C3), 131.4 (C15), 128.4 (C16 and C17), 122.9 (C$_{quat}$), 118.7 (C$_{quat}$), 112.0 (C6), 111.2 (C9), 105.1 (C$_{quat}$), 94.3 (C$_{alkyne}$), 83.3 (C$_{alkyne}$), 65.5 (OCH$_2$CH$_2$CH$_2$O), 56.2 (OCH$_3$), 53.8 (C11a), 37.9 (C1), 28.8 (OCH$_2$CH$_2$CH$_2$O); MS (ES), m/z (relative intensity) 729 (M$^+$·, 100).

Example 6

Formation of Key Monomer Intermediate ((11S, 11aS)-7,8-Dimethoxy-11-(tert-butyldimethylsilyloxymethyl)-10-(2,2,2-trichloroethoxycarbonyl)-2-[[(trifluoromethyl)sulfonyl]oxy]-1,2,3,10,11,11a-tetrahydro-5H-pyrrolo[2,1-c][1,4]benzodiazepin-5-one (27))

(2S)(4R)-N-(4,5-Dimethoxy-2-nitrobenzoyl)-2-(tert-butyldimethylsilyloxymethyl)-4-oxyacetylpyrrolidine (19)

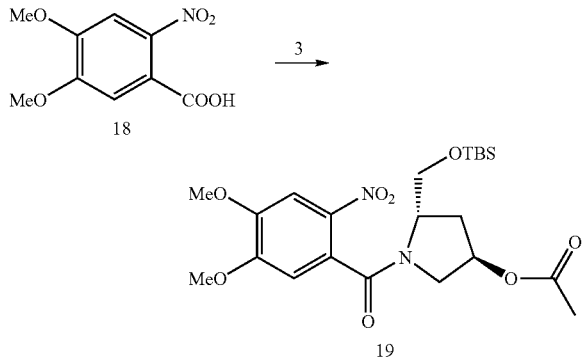

A stirred solution of 6-nitroveratric acid (18) (1.49 g, 6.58 mmol; 1.2 Equiv.) in dry DMF (2 mL) and DCM (80 mL) was treated with N-(3-Dimethylaminopropyl)-N-ethyl carbodiimide hydrochloride (1.26 g, 6.58 mmol, 1.2 Equiv.) and cooled to 0° C. 1-Hydroxybenzotriazole hydrate (1.03 g, 6.58 mmol, 1.2 Equiv.) was added in portions and the reaction mixture was allowed to warm to room temperature. After stirring for 1 h, a solution of 3 (1.5 g, 5.48 mmol, 1.0 Equiv.) in DCM (80 mL) was added dropwise and the mixture stirred for a further 15 h. This was followed by heating at 55° C. for a further 3 h. The reaction mixture was washed with NH$_4$Cl (60 mL), NaHCO$_3$ (60 mL), brine (60 mL), dried (MgSO$_4$) and concentrated in vacuo. Purification by flash chromatography (EtOAc/petroleum ether 4:6) afforded the product 19 as pale crystals (2.11 g, 79.9%): m.p. 134° C.; [α]$_D^{19}$=−91.9° (c=0.408, CHCl$_3$); $^1$H NMR (CDCl$_3$, 400 MHz) δ 0.12 (s, 6H, Si(CH$_3$)$_2$), 0.93 (s, 9H, C(CH$_3$)$_3$), 2.04 (s, 3 H, C═OCH$_3$), 2.20-2.28 (m, 1H, H1a), 2.39-2.45 (m, 1H, H1b), 3.22 (d, 1H, J=11.74 Hz, H3a), 3.47 (dd, 1H, J=11.89, 4.70 Hz, H3b), 3.75 (d, 1H, J=8.39 Hz, H11), 3.94 (s, 3H, CH$_3$O7), 3.98 (s, 3H, CH$_3$O8), 4.21 (d, 1H, J=9.76 Hz, H11), 4.56 (m, 1 H, H11a), 5.19 (m, 1H, H2b), 6.73 (s, 1H, H6), 7.68 (s, 1H, H9); $^{13}$C NMR (CDCl$_3$, 100 MHz) δ 171.0 (C═O), 166.3 (C5), 154.0 (C7), 149.1 (C8), 137.6 (C5-6), 127.8 (C9-10), 109.1 (C6), 107.3 (C9), 72.9 (C2), 62.6 (C11), 57.4 (C11a), 56.5, 56.6 (CH$_3$O7 and CH$_3$O8), 52.0 (C3), 33.0 (C1), 25.7 (C(CH$_3$)$_3$), 21.2 (C═OCH$_3$), 18.1 (Cquat), −5.5 (SiCH$_3$)$_2$); IR (film) 2953, 2856, 1740 (C═O), 1648 (C═O), 1579, 1525, 1463, 1427, 1338, 1278, 1243, 1225, 1115, 1070, 1028, 1004, 837, 780 cm$^{-1}$; MS (EI) m/z (relative intensity) 483 ([M+H]$^+$·, 100); Elem. Anal. calculated for C$_{22}$H$_{34}$N$_2$O$_8$Si: C, 54.75; H, 7.10; N, 5.80. Found: C, 54.50; H, 7.08; N, 5.79.

(2S,4R)-N-(2-Amino-4,5-dimethoxybenzoyl)-2-(tert-butyldimethylsilyloxymethyl)-4-oxyacetylpyrrolidine (20)

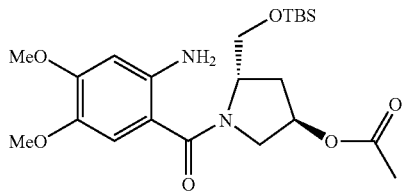

A suspension of 19 (61.75 g, 127.9 mmol; 1 Equiv.) and 10% w/w Pd/C (6.17 g) in ethanol (400 mL) was agitated under a H$_2$ atmosphere (45 psi) using Parr apparatus over a period of 3 h. The suspension was filtered through celite and the filtrate was evaporated in vacuo to afford 20 as a pale yellow oil (57.5 g, 99%): [α]$_D^{19}$=−105.1° (c=0.490, CHCl$_3$); $^1$H NMR (CDCl$_3$, 400 MHz) δ 0.03 (s, 6H, Si(CH$_3$)$_2$), 0.88 (s, 9H, C(CH$_3$)$_3$), 1.98 (s, 3H, C═OCH$_3$), 2.09-2.15 (m, 1H, H1a), 2.32-2.39 (m, 1H, H11b), 3.57-3.64 (m, 2H, H3a and H11), 3.73-3.77 (m, 4H, H3b and CH$_3$O8), 3.82 (s, 3H, CH$_3$O7), 4.00-4.11 (m (br), 1H, H11), 4.40-4.60 (m, 1H, H11a), 5.21-5.27 (m, 1H, H2b), 6.21 (s, 1H, H9), 6.69 (s, 1H, H6); $^{13}$C NMR (CDCl$_3$, 100 MHz) δ 170.6 (C═O), 170.0 (C5), 151.9 (C7), 141.7 (C9-10), 140.9 (C8), 112.2 (C6), 110.9 (C5-6), 100.6 (C9), 73.5 (C2), 62.6 (C11), 57.0 (C11a), 55.8, (CH$_3$O7), 56.6 (CH$_3$O8), 56.3 (C3), 32.9 (C1), 25.8 (C(CH$_3$)$_3$), 21.1 (C═OCH$_3$), 18.1 (Cquat), −5.5 (SiCH$_3$)$_2$); IR (film) 3455, 3355 (NH$_2$), 2931, 2857, 1740 (C═O), 1628 (C═O), 1594, 1516, 1401, 1238, 1165, 1120, 1006, 837, 778, 668 cm$^{-1}$; MS (EI) m/z (relative intensity) 453 ([M+H]$^+$·, 100).

(2S,4R)-N-(4,5-Dimethoxy-2-(2,2,2-trichloroethoxycarbonylamino)-benzoyl)-2-(tert-butyldimethylsilyloxymethyl)-4-oxyacetylpyrrolidine (21)

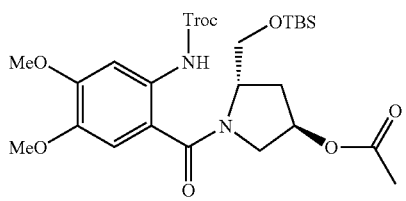

2,2,2-Trichloroethyl chloroformate (1.61 mL, 11.68 mmol, 2.2 Equiv.) was added to a stirred solution of 20 (2.40 g, 5.31 mmol; 1.0 Equiv.) and pyridine (1.72 mL, 21.24 mmol, 4.0 Equiv.) in dry DAM (70 mL) at −20° C. The mixture was allowed to warm to room temperature and stirred for a further 2.5 h. The reaction mixture was washed with NH$_4$Cl (2×60 mL), CuSO$_4$ (60 mL), water (60 mL), brine (60 mL), dried (MgSO$_4$), filtered and concentrated in vacuo to afford 21 as a colourless oil (3.32 g, 99%): [α]$_D^{20}$=−43.4° (c=0.980, CHCl$_3$); $^1$H NMR (CDCl$_3$, 400 MHz) δ 0.28 (s, 6H, Si(CH$_3$)$_2$), 0.87 (s, 9H, C(CH$_3$)$_3$), 1.96 (s, 3H, C═OCH$_3$), 2.10-2.16 (m, 1H, H1a), 2.35-2.41 (m, 1H, H1b), 3.55-3.65 (br m, 1H, H3a), 3.68-3.74 (m, 2H, H11 and H3b), 3.78 (s, 3H, CH$_3$O7), 3.91 (s, 3H, CH$_3$O8), 4.06-4.10 (m, 2H, Cl$_3$CCH$_2$ rotamers and H11), 4.55-4.65 (m, 1H, H11a), 4.74-4.82 (m, 1H, Cl$_3$CCH$_2$, rotamers), 5.20-5.25 (m, 1H, H2b), 6.75 (s, 1H, H6), 7.82 (br s, 1H, H9), 9.38 (br s, 1H, NH); $^{13}$C NMR (CDCl$_3$, 100 MHz) δ 170.5 (C=O), 169.2 (C5), 153.1, 151.4 (OC=ONH, rotamers), 151.9 (C8), 144.1 (C7), 132.2 (C5-6), 114.8 (C9-10), 111.1 (C6), 104.3 (C9), 95.3, 93.9 (Cl$_3$C, rotamers), 77.3, 76.3 (Cl$_3$CCH$_2$, rotamers), 73.4 (C2), 62.3 (C11), 57.3 (C11a), 57.2 (C3), 56.1, 56.2 (CH$_3$O7 and CH$_3$O8), 32.5 (C1), 25.8 (C(CH$_3$)$_3$), 21.1 (C=OCH$_3$), 18.1 (Cquat), −5.5 (SiCH$_3$)$_2$); IR (film) 3318, 2954, 2858, 1774, 1743 (C=O and OC=ON), 1601 (NC=O), 1525, 1464, 1422, 1398, 1230, 1200, 1125, 1004, 836, 777, 720 cm$^{-1}$; MS (EI) m/z (relative intensity) 629 ([M+H]$^+$·, 100).

(2S,4R)-N-(4,5-Dimethoxy-2-(2,2,2-trichloroethoxycarbonylamino)-benzoyl)-2-hydroxymethyl-4-oxyacetylpyrrolidine (22)

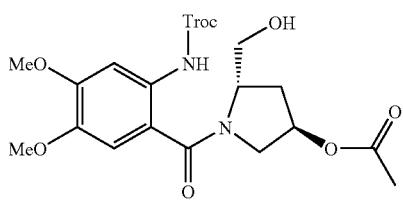

22

A mixture of acetic acid (81 mL) and water (18 mL) was added to a stirred solution of 21 (5.10 g, 8.12 mmol; 1.0 Equiv.) in THF (45 mL). The resulting solution was stirred at room temperature for a period of 48 h. The THF was removed in vacuo and the resulting mixture was neutralised to pH 7 with solid NaHCO$_3$ (Caution! vigorous effervescence). The resulting aqueous layer was extracted with DCM (5×150 mL), dried (MgSO$_4$) and concentrated in vacuo. The oily residue was subjected to flash chromatography (EtOAc/Petroleum ether 6:4) to give 22 as a foam (4.16 g, 99%): [α]$_D$$^{18}$=−65.0° (c=0.500, CHCl$_3$); $^1$H NMR (CDCl$_3$, 400 MHz) δ 2.01 (s, 3H, C=OCH$_3$), 2.05-2.13 (m, 1H, H1b), 2.27 (dd, 1H, J=14.20, 7.62 Hz, H1a), 3.62 (d, 1H, J=12.36 Hz, H3a), 3.65-3.74 (m, 1H, H11), 3.76 (dd, 1H, J=12.57, 3.80 Hz, H3b), 3.85 (s, 3 H, CH$_3$O7), 3.93 (s, 3H, CH$_3$O8), 3.98-4.08 (m, 1H, H11), 4.55-4.65 (m, 1H, H11a), 4.79 (d, 1H, J=12.09 Hz, Cl$_3$CCH$_2$), 4.84 (d, 1H, J=12.04 Hz, Cl$_3$CCH$_2$), 5.18-5.25 (m, 1H, H2b), 6.80 (s, 1H, H6), 7.73 (br s, 1H, H9), 9.03 (br s, 1H, NH); $^{13}$C NMR (CDCl$_3$, 100 MHz) δ 170.6 (C=O), 170.4 (C5), 152.1 (OC=ONH), 151.5 (C8), 144.6 (C7), 131.2 (C5-6), 115.5 (C9-10), 110.8 (C6), 104.8 (C9), 95.3 (Cl$_3$C), 74.4 (Cl$_3$CCH$_2$), 72.5 (C2), 64.5 (C11), 58.8 (C11a), 56.6 (C3), 56.5 (CH$_3$O7), 56.1 (CH$_3$O8), 33.7 (C1), 21.1 (C=OCH$_3$); IR (film) 3358 (br NH and OH), 3015, 2941, 1740 (C=O and OC=ON), 1602 (NC=O), 1525, 1463, 1433, 1398, 1231, 1174, 1125, 1037, 969, 817, 756 cm$^{-1}$; MS (EI) m/z (relative intensity) 363 ([M−Cl$_3$CCH$_2$O]$^+$·, 100), 513 ([M+H]$^+$·, 95).

(11S,11aS,2R)-7,8-Dimethoxy-11-hydroxy-2-oxyacetyl-10-(2,2,2-trichloroethoxycarbonyl)-1,2,3,10,11,11a-hexahydro-5H-pyrrolo[2,1-c][1,4]benzodiazepin-5-one (23)

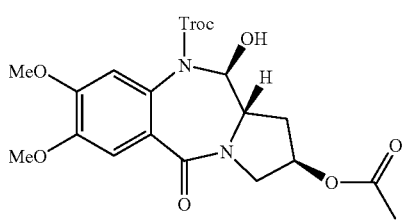

23

Diodobenzene diacetate (83.7 g, 259.8 mmol, 1.78 Equiv.) and 2,2,6,6-tetramethylpiperidine nitroxyl (TEMPO) (4.50 g, 28.8 mmol, 0.2 Equiv.) were added to a stirred solution of 22 (74.7 g, 145.4 mmol; 1.0 Equiv.) in dry DCM (1.5 L). The reaction mixture was stirred at room temperature for 15 h and diluted with DCM (500 mL). The organic phase was washed with a said sodium bisulphite (700 mL) and the aqueous layer was back-extracted with DCM (3×200 mL). The organic layers were combined, dried (MgSO$_4$), filtered and concentrated in vacuo. Purification by flash chromatography (EtOAc/Petroleum ether 7:3) afforded 23 as a white glass (57.65 g, 77%): [α]$_D$$^{18}$=+99.4° (c=0.483, CHCl$_3$); $^1$H NMR (CDCl$_3$, 400 MHz) δ 2.04 (s, 3H, C=OCH$_3$), 2.34-2.46 (m, 2H, H1b and H1a), 3.69-3.77 (m, 2H, H3b and 11a), 3.92 (s, 3H, CH$_3$O8), 3.95 (s, 3H, CH$_3$O7), 4.05 (dd, 1H, J=13.13, 2.35 Hz, H3a), 4.23 (d, 1H, J=12.02 Hz, Cl$_3$CCH$_2$), 5.25 (d, 1H, J=12.02 Hz, Cl$_3$CCH$_2$), 5.38 (p, 1 H, J=4.10 Hz, H2b), 5.70 (dd, 1H, J=9.66, 3.79 Hz, H11), 6.81 (s, 1H, H9), 7.27 (s, 1H, H6); $^{13}$C NMR (CDCl$_3$, 100 MHz) δ 170.3 (C=O), 167.4 (C5), 154.4 (OC=ONH), 151.1 (C8), 148.8 (C7), 127.5 (C9-10), 124.7 (C5-6), 112.7 (C9), 110.7 (C6), 95.0 (Cl$_3$C), 87.6 (C11), 75.0 (Cl$_3$CCH$_2$), 71.4 (C2), 58.3 (C11a), 56.19, 56.13 (CH$_3$O8 and CH$_3$O7), 51.1 (C3), 35.9 (C1), 21.0 (C=OCH$_3$); IR (film) 3421 (br OH), 3008, 2946, 1719 (C=O), 1623 (OC=ON), 1603 (NC=O), 1515, 1429, 1374, 1304, 1238, 1212, 1057, 870, 819, 758, 711, 644 cm$^{-1}$; MS (EI) m/z (relative intensity) 511 ([M−H]$^+$·, 100), 512.5 ([M+H]$^+$·, 99).

(17S,11aS,2R)-7,8-Dimethoxy-2-oxyacetyl-11-(tert-butyldimethylsilyloxymethyl)-10-(2,2,2-trichloroethoxycarbonyl)-1,2,3,10,11,11a-hexahydro-5H-pyrrolo[2,1-c][1,4]benzodiazepin-5-one (24)

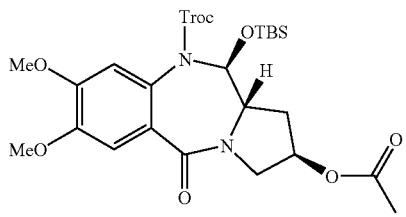

24

TBDMSOTf (0.56 mL, 2.44 mmol; 1.5 Equiv.) was added to a stirred solution of 23 (834 mg, 1.63 mmol, 1.0 Equiv.) and 2,6-lutidine (0.38 mL, 3.26 mmol, 2.0 Equiv.) in dry DCM (5 mL). The mixture was stirred at room temperature for 30 min and diluted with DCM (20 mL). The mixture was washed with sat$^d$ CuSO$_4$ (2×20 mL), sat$^d$ NaHCO$_3$ (30 mL), brine (30 mL), dried (MgSO$_4$) and concentrated in vacuo to afford 6 as white glass (1.01 g, 99%): [α]$_D$$^{18}$=+52.7° (c=0.237, CHCl$_3$); $^1$H NMR (CDCl$_3$, 400 MHz) δ 0.23 (s, 6H, Si(CH$_3$)$_2$), 0.87 (s, 9H, C(CH$_3$)$_3$), 2.03 (s, 3H, C=OCH$_3$), 2.18-2.25 (m, 1H. H1b), 2.30-2.40 (m, 1H, H1a), 3.66-3.72 (m, 2H, H3b and 11a), 3.89 (s, 3H, CH$_3$O8), 3.95 (s, 3H, CH$_3$O7), 4.13 (d, 1H, J=13.40 Hz, H3a), 4.18 (d, 1H, J=12.04 Hz, Cl$_3$CCH$_2$), 5.23 (d, 1H, J=12.03 Hz, Cl$_3$CCH$_2$), 5.37 (p, 1H, J=2.62 Hz, H2b), 5.77 (d, 1H, J=8.95 Hz, H11), 6.74 (s, 1H, H9), 7.28 (s, 1H, H6); $^{13}$C NMR (CDCl$_3$, 100 MHz) δ 170.3 (C=O), 167.9 (C5), 153.5 (OC=ONH), 151.0 (C8), 148.9 (C7), 128.0 (C9-10), 125.4 (C5-6), 112.9 (C9), 110.6 (C6), 95.2 (Cl$_3$C), 88.2 (C11), 74.7 (Cl$_3$CCH$_2$), 71.7 (C2), 60.5 (C11a), 56.1 (CH$_3$O7), 56.9 (CH$_3$O8), 51.2 (C3), 36.2 (C1), 25.5 (C(CH$_3$)$_3$) 21.0 (C=OCH$_3$), 17.8 (Cquat), −4.3 and −5.3 (Si(CH$_3$)$_2$); IR (film) 3023, 2956, 1738 (C=O), 1718 (OC=ON), 1644 (NC=O), 1605, 1518, 1466, 1428, 1411, 1376, 1301, 1245, 1214, 1116, 1075, 1041, 1023, 842, 784, 756, 730, 712 cm$^{-1}$; MS (EI) m/z (relative intensity) 627 ([M+H]$^+$·, 100).

(11S,11aS,2R)-7,8-Dimethoxy-2-hydroxy-11-(tert-butyldimethylsilyloxymethyl)-10-(2,2,2-trichloroethoxycarbonyl)-1,2,3,10,11,11a-hexahydro-5H-pyrrolo[2,1-c][1,4]benzodiazepin-5-one (25)

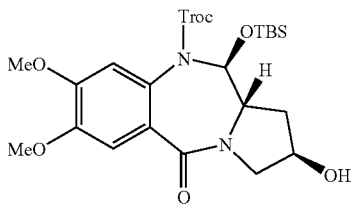

A solution of $K_2CO_3$ (732 mg, 5.30 mmol; 1.0 Equiv.) in water (15 mL) was added to a stirred solution of 24 (3.32 g, 5.30 mmol, 1.0 Equiv.) in MeOH (15 mL) and THF (5 mL). The mixture was stirred at room temperature for 5 h and then excess solvent was removed by rotary evaporation at reduced pressure. The remaining aqueous residue was neutralised to pH 7 with 1N HCl and extracted with EtOAc (4×30 mL). The organic layers were combined, washed with brine (50 mL), dried ($MgSO_4$), filtered and concentrated in vacuo. The resulting oil was subjected to flash chromatography (EtOAc) to afford 25 as a white glass (2.84 g, 92%): $[\alpha]_D^{22}$=+58.3° (c=0.587, $CHCl_3$); $^1H$ NMR ($CDCl_3$, 500 MHz) δ 0.22 (s, 6H, $Si(CH_3)_2$), 0.87 (s, 9H, $C(CH_3)_3$), 2.06-2.11 (m, 1H, H1b), 2.28-2.33 (m, 1 H, H1a), 3.60 (dd, 1H, J=4.31, 12.67 Hz, H3b), 3.71 (q, 1H, J=7.42, 15.67 Hz, H11a), 3.88 (s, 6H, $CH_3O8$ and $CH_3O7$), 4.01 (d, 1H, J=12.93 Hz, H3a), 4.17 (d, 1H, J=12.03 Hz, $Cl_3CCH_2$), 4.58 (br s, 1H, H2b), 5.23 (d, 1H, J=12.03 Hz, $Cl_3CCH_2$), 5.54 (d, 1H, J=9.00 Hz, H11), 6.73 (s, 1H, H9), 7.21 (s, 1H, H6); $^{13}C$ NMR ($CDCl_3$, 125 MHz) δ 168.4 (C5), 153.6 (OC=ONH), 151.9 (C8), 148.8 (C7), 128.0 (C9-10), 125.5 (C5-6), 112.8 (C9), 110.5 (C6), 95.2 ($Cl_3C$), 88.2 (C11), 74.7 ($Cl_3CCH_2$), 69.5 (C2), 60.8 (C11a), 56.0, 55.9 ($CH_3O8$ and $CH_3O7$), 54.0 (C3), 38.8 (C1), 25.6 ($C(CH_3)_3$), 17.8 (Cquat), −4.2 and −5.2 ($Si(CH_3)_2$); IR (film) 3400 (br OH), 2932, 1731 (OC=ON), 1629 (NC=O), 1604, 1515, 1456, 1430, 1407, 1302, 1273, 1214, 1117, 1075, 987, 837, 754, 712, 638 $cm^{-1}$; MS (EI) m/z (relative intensity) 585 ([M+H]$^+$, 100).

(11S,11aS)-7,8-Dimethoxy-2-oxo-11-(tert-butyldimethylsilyloxymethyl)-10-(2,2,2-trichloroethoxycarbonyl)-1,2,3,10,11,11a-hexahydro-5H-pyrrolo[2,1-c][1,4]benzodiazepin-5-one (26)

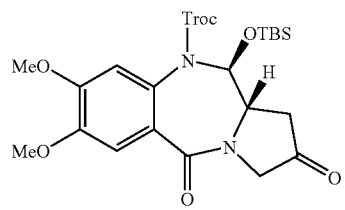

Diodobenzene diacetate (2.44 g, 7.58 mmol, 1.78 Equiv.) and 2,2,6,6-tetramethylpiperidine nitroxyl (TEMPO) (133 mg, 0.85 mmol, 0.2 Equiv.) were added to a stirred solution of 25 (2.49 g, 4.26 mmol; 1.0 Equiv.) in dry DCM (40 mL). The mixture was stirred at room temperature for 18 h and the reaction mixture was diluted with DAM (50 mL). The organic phase was washed with said sodium bisulphite (2×25 mL), brine (40 mL), dried ($MgSO_4$) and concentrated in vacuo. Purification by flash chromatography (EtOAc/Petroleum ether 6:4) afforded 26 as a white glass. (2.26 g, 91%): $[\alpha]_D^{22}$=+95.0° (c=0.795, $CHCl_3$); $^1H$ NMR ($CDCl_3$, 500 MHz) δ 0.22, 0.23 (two s, 6H, $Si(CH_3)_2$), 0.86 (s, 9H, $C(CH_3)_3$), 2.56 (dd, 1H, J=3.12, 19.60, H1b), 2.96 (dd, 1H, J=10.29, 18.9, H1a), 3.90 (s, 3H, $CH_3O8$), 3.95-3.99 (m, 5H, H3b, H11a and $CH_3O7$), 4.21 (d, 1H, J=12.02 Hz, $Cl_3CCH_2$), 4.32 (d, 1H, J=20.93 Hz, H3a), 5.24 (d, 1H, J=12.03 Hz, $Cl_3CCH_2$), 5.83 (d, 1H, J=9.26 Hz, H11), 6.77 (s, 1H, H9), 7.25 (s, 1H, H6); $^{13}C$ NMR ($CDCl_3$, 125 MHz) δ 207.8 (C2), 168.0 (C5), 153.7 (OC=ONH), 151.4 (C8), 149.2 (C7), 128.0 (C9-10), 124.5 (C5-6), 113.0 (C9), 110.4 (C6), 95.1 ($Cl_3C$), 87.4 (C11), 74.8 ($Cl_3CCH_2$), 58.9 (C11a), 56.2 ($CH_3O7$), 56.0 ($CH_3O8$), 52.8 (C3), 40.3 (C1), 25.5 ($C(CH_3)_3$), 17.8 (Cquat), −4.2 and −5.3 ($Si(CH_3)_2$); IR (film) 2934, 1763 (C=O), 1720 (OC=ON), 1649 (NC=O), 1604, 1515, 1402, 1274, 1217, 1120, 1075, 1002, 866, 834, 756, 712 $cm^{-1}$; MS (EI) m/z (relative intensity) 615 ([M+MeOH]$^+$, 100).

(11S,11aS)-7,8-Dimethoxy-11-(tert-butyldimethylsilyloxymethyl)-10-(2,2,2-trichloroethoxycarbonyl)-2-[[(trifluoromethyl)sulfonyl]oxy]-1,2,3,10,11,11a-tetrahydro-5H-pyrrolo[2,1-c][1,4]benzodiazepin-5-one (27)

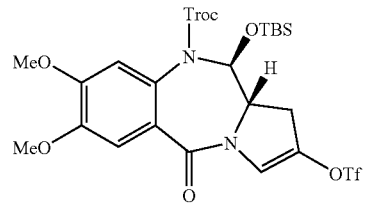

Pyridine (1.71 mL; 21.17 mmol; 7 Equiv.) and trifluoromethanesulfonic anhydride (3.56 mL; 21.17 mmol; 7 Equiv.) were added to a stirred solution of 27 (1.76 g, 3.02 mmol; 1 Equiv.) in dry $CHCl_3$ (50 mL) at 0-5° C. (ice bath). The ice bath was removed and the reaction mixture was stirred at room temperature for 3 h. At this point TLC analysis revealed the persistence of starting material. As a result, one extra equivalent of pyridine and $Tf_2O$ was added (0.24 and 0.51 mL, respectively). The reaction was stirred for an additional 1 h until complete consumption of the starting material was observed by TLC. The reaction mixture was washed with water, sat$^d$ $CuSO_4$, sat$^d$ $NaHCO_3$, dried ($MgSO_4$), filtered and the solvent was evaporated in vacuo. The resulting residue was purified by flash chromatography (EtOAc/Petroleum ether 2:8) to give 27 as a pale yellow glass (1.12 g, 52%): $[\alpha]_D^{22}$=+56.2° (c=0.587, $CHCl_3$); $^1H$ NMR ($CDCl_3$, 500 MHz) δ 0.25, 0.27 (two s, 6H, $Si(CH_3)_2$), 0.88 (s, 9H, $C(CH_3)_3$), 2.82 (dd, 1H, J=2.79, 16.66 Hz, H1b), 3.33 (ddd, 1H, J=1.96, 10.73, 16.59 Hz, H1a), 3.90 (s, 3H, $CH_3O8$), 3.94 (s, 3H, $CH_3O7$), 3.88-3.96 (m, 1H, H11a), 4.20 (d, 1H, J=12.00 Hz, $Cl_3CCH_2$), 5.23 (d, 1H, J=12.00 Hz, $Cl_3CCH_2$), 5.93 (d, 1H, J=9.26 Hz, H11), 6.74 (s, 1H, H9), 7.17 (s, 1H, H3), 7.23 (s, 1H, H6); $^{13}C$ NMR ($CDCl_3$, 125 MHz) δ 164.9 (C5), 153.6 (OC=ONH), 151.8 (C8), 149.3 (C7), 136.0 (C2), 127.9 (C9-10), 123.8 (C5-6), 121.0 (C3), 119.8 ($CF_3$), 113.2 (C9), 110.7 (C6), 95.1 ($Cl_3C$), 86.4 (C11), 74.9 ($Cl_3CCH_2$), 60.6 (C11a), 56.2 ($CH_3O7$), 56.0 ($CH_3O8$), 34.4 (C1), 25.5 ($C(CH_3)_3$), 17.8 (Cquat), −4.2 and −5.4 ($Si(CH_3)_2$); IR (film) 3008, 2930, 2858, 1725 (OC=ON), 1651 (NC=O), 1516, 1423, 1214, 1136, 1078, 897, 835, 783, 760, 713, 642 $cm^{-1}$; MS (EI) m/z (relative intensity) 715 ([M+H]$^+$, 100).

Example 7

(11aS)-7,8-Dimethoxy-2-(1-propenyl)-1,11a-dihydro-5H-pyrrolo[2,1-c][1,4]benzodiazepin-5-one (29)

(11S,11aS)-7,8-Dimethoxy-11-(tert-butyldimethylsilyloxymethyl)-10-(2,2,2-trichloroethoxycarbonyl)-2-(1-propenyl)-1,2,3,10,11,11a-tetrahydro-5H-pyrrolo[2,1-c][1,4]benzodiazepin-5-one (28)

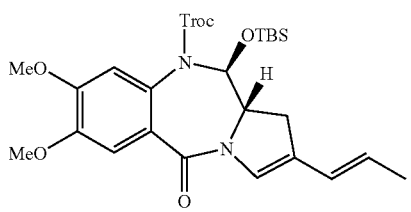

28

A mixture of Et$_3$N (0.34 mL, 2.48 mmol, 3 Equiv.), water (0.5 mL) and EtOH (1.70 mL) was added to a solution of 27 (590 mg, 0.826 mmol, 1 Equiv.) in toluene (1.70 mL) with vigorous stirring. The reaction mixture was treated with trans-propenylboronic acid (92.2 mg, 1.07 mmol, 1.3 Equiv.) and Pd(PPh$_3$)$_4$ (19 mg, 0.016 mmol, 0.02 Equiv.). After 2 h stirring at room temp TLC revealed no reaction. The mixture was then heated to reflux (111° C.) for 30 min after which time TLC showed the complete consumption of starting material. The reaction mixture was allowed to cool to room temperature and diluted with EtOAc (30 mL). The organic phase was extracted with water (20 mL), brine (20 mL), dried (MgSO$_4$), filtered and the solvent was evaporated in vacuo. The resulting residue was purified by flash chromatography (EtOAc/Petroleum ether 2:8) to afford the product 10 (297 mg, 59%): [α]$_D^{22}$=+78.2° (c=0.582, CHCl$_3$); $^1$H NMR (CDCl$_3$, 500 MHz) δ 0.24, 0.26 (two s, 6H, Si(CH$_3$)$_2$), 0.89 (s, 9H, C(CH$_3$)$_3$), 1.83 (dd, 3H, J=0.79, 6.69 Hz, H14), 2.58 (dd, 1H, J=3.11, 16.45 Hz, H1b), 3.06 (dd, 1H, J=10.59, 16.40 Hz, H1a), 3.82-3.88 (m, 1H, H11a), 3.89 (s, 3H. CH$_3$O8), 3.94 (s, 3H, CH$_3$O7), 4.17 (d, 1H, J=12.04 Hz, Cl$_3$CCH$_2$), 5.23 (d, 1H, J=12.04 Hz, Cl$_3$CCH$_2$), 5.50-5.56 (m, 1H, H13), 5.84 (d, 1H, J=8.86 Hz, H11), 6.25 (d, 1H, J=14.80 Hz, H12), 6.75 (s, 1H, H9), 6.88 (s, 1H, H3), 7.24 (s, 1H, H6); $^{13}$C NMR (CDCl$_3$, 125 MHz) δ 163.6 (C5), 153.6 (OC=ONH), 151.1 (C8), 149.0 (C7), 127.9 (C9-10), 126.5 (C13), 125.5 (C5-6), 124.7 (C12), 124.6 (C3), 123.6 (C2), 113.0 (C9), 110.5 (C6), 95.2 (Cl$_3$C), 87.2 (C11), 74.7 (Cl$_3$CCH$_2$), 61.4 (C11a), 56.2 (CH$_3$O7), 56.0 (CH$_3$O8), 33.9 (C1), 25.6 (C(CH$_3$)$_3$), 18.4 (C14), 17.9 (Cquat), −4.2 and −5.1 (Si (CH$_3$)$_2$); IR (film) 2961, 2935, 2858, 1723 (OC=ON), 1648 (NC=O), 1514, 1404, 1272, 1216, 1076, 837, 756, 644 cm$^{-1}$; MS (EI) m/z (relative intensity) 607 ([M+H]$^+$, 100).

(11aS)-7,8-Dimethoxy-2-(1-propenyl)-1,11a-dihydro-5H-pyrrolo[2,1-c][1,4]benzodiazepin-5-one (29)

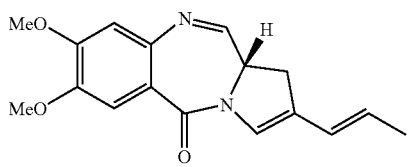

29

10% Cd/Pd couple (418 mg, 3.38 mmol, 8.2 Equiv.) was added to a rapidly stirring mixture of 28 (250 mg, 0.412 mmol, 1 Equiv.), THF (3 mL) and 1 N ammonium acetate (3 mL). The reaction mixture was allowed to stir for 3.5 h when TLC showed the complete consumption of the starting material. The solids were filtered and rinsed with H$_2$O and DAM. The aqueous layer was extracted with DCM (3×30 mL) and the organic extracts were combined, washed with brine (50 mL), dried (MgSO$_4$), filtered and evaporated in vacuo to provide the crude product. Purification by flash column chromatography (0.5%→2% MeOH in CHCl$_3$) afforded 29 as a yellow glass (96 mg, 78%): [α]$_D^{24}$=+989° (c=0.890, CHCl$_3$); $^1$H NMR (CDCl$_3$, 400 MHz) δ 1.85 (d, 3H, J=6.26 Hz, H14), 3.12 (dd, 1H, J=4.95, 16.27 Hz, H1b), 3.30 (dd, 1H, J=11.80, 15.27 Hz, H1a), 3.93 (s, 3H, CH$_3$O8), 3.95 (s, 3H, CH$_3$O7), 4.30 (dt, J=4.95, 15.70 Hz, H11a), 5.55-5.65 (m, 1H, H13), 6.27 (d, J=16.04 Hz, H12), 6.81 (s, 1H, H9), 6.92 (s, 1H, H3), 7.50 (s, 1H, H6), 7.82 (d, 1H, J=4.00 Hz, H11); $^{13}$C NMR (CDCl$_3$, 100 MHz) δ 162.7 (C11), 161.2 (C5), 151.8 (C8), 147.7 (C7), 140.4 (C9-10), 126.9 (C13), 124.46, 124.43 (C12 and C3), 123.9 (C2), 119.2 (C5-6), 111.6 (C6), 109.8 (C9), 56.18, 56.11 (CH$_3$O7 and CH$_3$O8), 53.8 (C11a), 34.2 (C1), 18.4 (C14); IR (film) 3018, 2997, 2930, 2847, 1610, 1598 (C=O), 1507, 1431, 1344, 1254, 1214, 1101, 1065, 959, 862, 779 cm$^{-1}$; MS (EI) m/z (relative intensity) 331 ([M+MeOH]$^+$, 100), 299 ([M+H]$^+$, 45).

Example 8

Parallel Synthesis of C2-Substituted PBDs (30a-al)

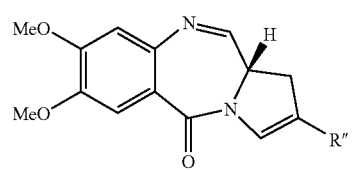

30a-al (i) A solution of triethylamine (0.12 mL, 6 equiv.) in water (0.2 mL) and ethanol (1.0 mL) was poured into a stirred solution of 27 (100 mg, 0.14 mmol, 1 Equiv.) in toluene (1.0 mL) in an Emrys™ Process vial. To the solution was added the appropriate boronic acid (1.07 equiv.) and polystyrene triphenylphosphine palladium (0) PS-PPh$_3$Pd (15 mg, 0.0014 mmol, 0.01 Equiv). The vial was sealed with a Reseal™ septum, and the suspension then irradiated at 100° C. for 20 minutes under microwave radiation using an EmryS™ Optimizer Microwave Station when TLC showed absence of starting material. N,N-diethanolaminomethyl polystyrene PS-DEAM (87.5 mg, 0.14 mmol, 1.0 equiv. [13 equiv. on boronic acid excess]) was added to the reaction, and the suspension was irradiated at 100° C. for 10 minutes under microwave radiation (as above). Water (3 mL) was added to the reaction, and the suspension shaken for 10 minutes. The mixture was then transferred to a phase separator (PS) cartridge fitted with a selectively permeable frit pre-conditioned with CH$_2$Cl$_2$ (3 mL) and coupled to a Na$_2$SO$_4$ cartridge. Extraction with CH$_2$Cl$_2$ (3×5 mL), followed by concentration in vacuo yielded an oil which was redissolved in THF (1.5 mL) and 1N ammonium acetate (1.5 mL).

(ii) To the mixture resulting from the previous step was added 10% Cd/Pb (140 mg, 1.12 mmol, 8.0 Equiv.) while vigorously stirring and the reaction was kept for 1 hour at room temperature when TLC showed absence of starting material. The mixture was poured into an identical PS cartridge pre-conditioned with CH$_2$Cl$_2$ (3 mL) and coupled to a Na$_2$SO$_4$ cartridge. Extraction with CH$_2$Cl$_2$ (3×5 mL) followed by concentration in vacuo gave an oil which was subjected to flash chromatography (EtOAc:Hexane 1:1) afforded the desired compounds, which are listed below.

| Compound | R" | Yield (%)† | [α]_D* |
|---|---|---|---|
| 30a | Phenyl | 62 | +1012° |
| 30b | 4-methylphenyl | 39 | +916° |
| 30c | 2-methylphenyl | 38 | +802° |
| 30d | 4-ethylphenyl | 45 | +985° |
| 30e | 2,6-dimethylphenyl | 35 | +549° |
| 30f | 4-methoxyphenyl | 99‡ | +976° |
| 30g | 3-methoxyphenyl | — | +825° |
| 30h | 4-tert-butylphenyl | 35 | +781° |
| 30i | 4-fluorophenyl | 41 | +978° |
| 30j | 4-chlorophenyl | 67 | +796° |
| 30k | 4-biphenyl | 44 | +792° |
| 30l | 4-phenoxyphenyl | 47 | +823° |
| 30m | 2-naphthyl | 47 | +720° |
| 30n | 3,4-methylenedioxyphenyl | 46 | +837° |
| 30o | trans-2-(4-methylphenyl)vinyl | 58 | +990° |
| 30p | 2-thiophenyl | 59 | +974° |
| 30q | trans-propenyl | 78‡ | +989° |
| 30r | 4-dimethylaminophenyl | 44 | +858° |
| 30s | 4-methylthiophenyl | 18 | +979° |
| 30t | 4-vinylphenyl | 36 | +796° |
| 30u | 3,4-dichlorophenyl | 41 | +641° |
| 30v | 4-trifluoromethylphenyl | 28 | +785° |
| 30w | 4-isopropylphenyl | 44 | +985° |
| 30x | 4-cyanophenyl | 42 | +1000° |
| 30y | 3-pyridinyl | 14 | +1200° |
| 30z | 4-pyridinyl | 27 | +859° |
| 30aa | 4-formylphenyl | 42 | +928° |
| 30ab | 4-carboxylphenyl | 43 | — |
| 30ac | 2,6-dimethoxyphenyl | 18.5 | — |
| 30ad | 4-acetanilide | 26.3 | — |
| 30ae | 4-aminophenyl | 21.3 | — |
| 30af | 1-naphthyl | 32 | — |
| 30ag | 5-indole | 34 | — |
| 30ah | 3-aminophenyl | 41 | — |
| 30ai | 2,6-difluorophenyl | 14 | — |
| 30aj | 1-pyrenyl | 39 | — |
| 30ak | 4-hydroxyphenyl | 14 | — |
| 30al | trans-hexenyl | — | — |

†Overall yield, including Suzuki coupling followed by imine formation.
‡yield calculated from Troc-deprotection final step only.
*Concentration range: 0.047-0.89 g/100 mL; Temp.: 20-29° C. All samples were dissolved in HPLC grade chloroform stabilised with amylene, purchased from Fisher Chemicals, Leicestershire, UK..

Example 9

Determination of In Vitro Cytotoxicity

K562 human chronic myeloid leukaemia cells were maintained in RPM1 1640 medium supplemented with 10% fetal calf serum and 2 mM glutamine at 37° C. in a humidified atmosphere containing 5% $CO_2$ and were incubated with a specified dose of drug for 1 hour or 96 hours at 37° C. in the dark. The incubation was terminated by centrifugation (5 min, 300 g) and the cells were washed once with drug-free medium. Following the appropriate drug treatment, the cells were transferred to 96-well microtiter plates ($10^4$ cells per well, 8 wells per sample). Plates were then kept in the dark at 37° C. in a humidified atmosphere containing 5% $CO_2$. The assay is based on the ability of viable cells to reduce a yellow soluble tetrazolium salt, 3-(4,5-dimethylthiazol-2-yl)-2,5-diphenyl-2H-tetrazolium bromide (MTT, Aldrich-Sigma), to an insoluble purple formazan precipitate. Following incubation of the plates for 4 days (to allow control cells to increase in number by approximately 10 fold), 20 μL of MTT solution (5 mg/mL in phosphate-buffered saline) was added to each well and the plates further incubated for 5 h. The plates were then centrifuged for 5 min at 300 g and the bulk of the medium pipetted from the cell pellet leaving 10-20 μL per well. DMSO (200 μL) was added to each well and the samples agitated to ensure complete mixing. The optical density was then read at a wavelength of 550 nm on a Titertek Multiscan ELISA plate reader, and a dose-response curve was constructed. For each curve, an $IC_{50}$ value was read as the dose required to reduce the final optical density to 50% of the control value.

Results

The following compounds showed an $IC_{50}$ of less than 1 μM after a 96 hour incubation period: 30a, 30b, 30c, 30d, 30f, 30g, 30h, 30i, 30j, 30k, 30l, 30m, 30n, 30o, 30p, 30q, 30r, 30s, 30t, 30u, 30v, 30w, 30x, 30y, 30z, 30aa, 30ac, 30ad, 30ae, 30af, 30ag, 30ah, 30ai, 30aj, 30al.

The following compounds showed an $IC_{50}$ of less than 10 nM after a 96 hour incubation period: 30a, 30b, 30c, 30g, 30i, 30n, 30p, 30q, 30ai.

| Compound | $IC_{50}{}^b$ (μM) |
|---|---|
| ZC-204 | 3.80 ± 0.44 |
| ZC-207 | 0.0053 ± 0.0049 |
| ZC-209 | <0.01 |
| ZC-211 | <0.01 |

$^b$1 hour incubation

The invention claimed is:

1. A compound of formula III:

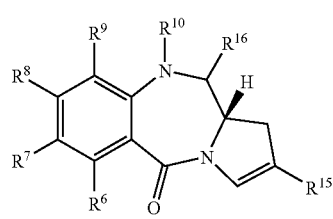

or a pharmaceutically acceptable salt thereof, wherein:
  $R^6$ and $R^9$ are independently selected from H, R, OH, OR, SH, SR, $NH_2$, NHR, NRR', nitro, $Me_3Sn$ and halo;
  R and R' are independently selected from optionally substituted $C_{1-12}$ alkyl, $C_{3-20}$ heterocyclyl and $C_{5-20}$ aryl groups;
  the compound being a dimer with each monomer being of formula (III), where the $R^8$ of each monomer form together a dimer bridge having the formula —X—R"—X— linking the monomers, where R" is a $C_{3-12}$ alkylene group, which chain may be interrupted by one or more heteroatoms and/or aromatic rings, and each X is independently selected from O, S, or NH, and $R^7$ is selected from H, R, OH, OR, SH, SR, $NH_2$, NHR, NRR', nitro, $Me_3Sn$ and halo, or any pair of adjacent groups from $R^6$ to $R^9$ together form a group —O—$(CH_2)_p$—O—, where p is 1 or 2;
  either $R^{10}$ and $R^{16}$ together form a double bond between N10 and C11, or $R^{10}$ is H and $R^{16}$ is OH;
  $R^{15}$ is an optionally substituted $C_{5-20}$ aryl group,
  wherein the optional substituents are independently selected from the group consisting of $C_{1-12}$ alkyl, $C_{3-12}$ cycloalkyl, $C_{3-20}$ heterocyclyl, $C_{5-20}$ aryl, halo, hydroxyl, —$OR^1$ wherein $R^1$ is a $C_{1-7}$ alkyl group or $C_{3-20}$ heterocyclyl group or $C_{5-10}$ aryl group, alkoxy, —$CH(OR^1)(OR^2)$ wherein $R^1$ is as defined above and $R^2$ is independently a $C_{1-7}$ alkyl group or $C_{3-20}$ heterocyclyl group or $C_{5-10}$ aryl group or $R^1$ and $R^2$ together with the two oxygen atoms to which they are attached form a heterocyclic ring having from 4 to 8 ring atoms, —$CH(OH)(OR^1)$ wherein $R^1$ is as defined above, ketal, hemiketal, oxo, thione, imino, formyl, acyl, carboxy, thiocarboxy, thiolocarboxy, —C(=NH)OH, —C(=NOH)OH, —C(=O)$OR^1$ wherein $R^1$ is as defined above, acyloxy, oxycarboyloxy, amino, amido, thioamido, acylamido, aminocarbonyloxy, ureido, guanidine, tetrazolyl, amindino, nitro, nitroso, azido, cyano, isocyano, cyanato, isocyanato, thiocyano, isothiocyano, sulfhydryl, thioether, disulfide, sulfine, sulfone, —S(=O)OH, —SO₂H, —S(=O)₂OH, —SO₃H, sulfinate, sulfonate, sulfinyloxy, sulfonyloxy, sulfate, sulfamyl, sulfonamide, sulfamino, sulfonamino, sulfinamino, phosphino, phosphor, phosphinyl, phosphono, —P(=O)(OR$^{17}$)₂ wherein R$^{17}$ is —H or C$_{1-7}$ alkyl group or C$_{3-20}$ heterocyclyl group or C$_{5-20}$ aryl group, phosphonooxy, —PO(=O)(OR$^{17}$)₂ wherein R$^{17}$ is as defined above, —OP(OH)₂, phosphate, phosphoramidite, and phosphoramidate; and wherein heteroatoms of the heterocyclyl groups and the optional heteroatoms of the alkylene groups are independently selected from the group consisting of N, S, and O.

2. A compound according to claim 1, wherein the dimer bridge has the formula —O—(CH₂)$_n$—O— linking the monomers, where n is from 3 to 12.

3. A compound according to claim 2, wherein n is from 3 to 7.

4. A compound according to claim 1, wherein R$^{10}$ and R$^{16}$ together form a double bond between N10 and C11.

5. A compound according to claim 1, wherein R$^9$ is H.

6. A compound according to claim 1, wherein R$^7$ and R$^8$ are independently selected from H, OH, OR, SH, NH₂, NHR, NRR' and halo.

7. A pharmaceutical composition containing a compound of claim 1, and a pharmaceutically acceptable carrier or diluent.

8. A method of treatment of chronic myeloid leukemia, comprising administering to a subject in need of treatment a therapeutically-effective amount of a compound of claim 1.

9. A method of synthesizing a compound of formula III:

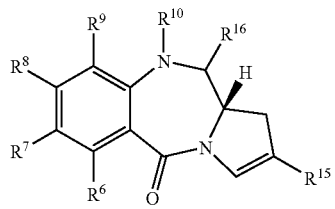

III comprising reacting a compound of formula I:

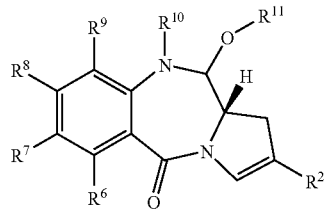

I with a compound of formula z-R$^{15}$ in a coupling reaction, wherein
R$^6$ and R$^9$ are independently selected from H, R, OH, OR, SH, SR, NH₂, NHR, NRR', nitro, Me₃Sn and halo;
R and R' are independently selected from optionally substituted C$_{1-12}$ alkyl, C$_{3-20}$ heterocyclyl and C$_{5-20}$ aryl groups;
R$^7$ and R$^8$ are independently selected from H, R, OH, OR, SH, SR, NH₂, NHR, NRR', nitro, Me₃Sn and halo, or the compound is a dimer with each monomer being of formula (I), where the R$^7$ groups or R$^8$ groups of each monomers form together a dimer bridge having the formula —X—R"—X— linking the monomers, where R" is a C$_{3-12}$ alkylene group, which chain may be interrupted by one or more heteroatoms and/or aromatic rings, and each X is independently selected from O, S, or NH;
or any pair of adjacent groups from R$^6$ to R$^9$ together form a group —O—(CH₂)$_p$—O—, where p is 1 or 2;
R$^{10}$ is a carbamate-based nitrogen protecting group;
R$^2$ is a labile leaving group;
R$^{16}$ is either O—R$^{11}$, where R$^{11}$ is an oxygen protecting group, or OH, or R$^{10}$ and R$^{16}$ together form a double bond between N10 and C11;
z-R$^{15}$ is any reactant suitable for a coupling reaction;
R$^{15}$ is an optionally substituted C$_{5-20}$ aryl group,
wherein the optional substituents are independently selected from the group consisting of C$_{1-12}$ alkyl, C$_{3-12}$ cycloalkyl, C$_{3-20}$ heterocyclyl, C$_{5-20}$ aryl, halo, hydroxyl, —OR wherein R is a C$_{1-7}$ alkyl group or C$_{3-20}$ heterocyclyl group or C$_{5-10}$ aryl group, alkoxy, —CH(OR$^1$)(OR$^2$) wherein R$^1$ is as defined above and R$^2$ is independently a C$_{1-7}$ alkyl group or C$_{3-20}$ heterocyclyl group or C$_{5-10}$ aryl group or R$^1$ and R$^2$ together with the two oxygen atoms to which they are attached form a heterocyclic ring having from 4 to 8 ring atoms, —CH(OH)(OR$^1$) wherein R$^1$ is as defined above, ketal, hemiketal, oxo, thione, imino, formyl, acyl, carboxy, thiocarboxy, thiolocarboxy, —C(=NH)OH, —C(=NOH)OH, —C(=O)OR$^1$ wherein R$^1$ is as defined above, acyloxy, oxycarboyloxy, amino, amido, thioamido, acylamido, aminocarbonyloxy, ureido, guanidine, tetrazolyl, amindino, nitro, nitroso, azido, cyano, isocyano, cyanato, isocyanato, thiocyano, isothiocyano, sulfhydryl, thioether, disulfide, sulfine, sulfone, —S(=O)OH, SO₂H, —S(=O)₂OH, —SO₃H, sulfinate, sulfonate, sulfinyloxy, sulfonyloxy, sulfate, sulfamyl, sulfonamide, sulfamino, sulfonamino, sulfinamino, phosphino, phosphor, phosphinyl, phosphono, —P(=O)(OR$^{17}$)₂ wherein R$^{17}$ is —H or C$_{1-7}$ alkyl group or C$_{3-20}$ heterocyclyl group or C$_{5-20}$ aryl group, phosphonooxy, —PO(=O)(OR$^{17}$)₂ wherein R$^{17}$ is as defined above, —OP(OH)₂, phosphate, phosphoramidite, and phosphoramidate; and wherein heteroatoms of the heterocyclyl groups and the optional heteroatoms of the alkylene groups are independently selected from the group consisting of N, S, and O.

10. A method according to claim 9, wherein the synthesis of said compound of formula III uses a palladium catalysed coupling step.

11. A method according to claim 10, wherein the palladium catalyst is Pd(PPh₃)₄, Pd(OCOCH₃)₂, PdCl₂ or Pd(dba)₃.

12. A method according to claim 10, wherein the coupling reaction is performed under microwave conditions.

13. A method according to claim 10, wherein the palladium catalyst is solid supported.

14. A compound of formula III

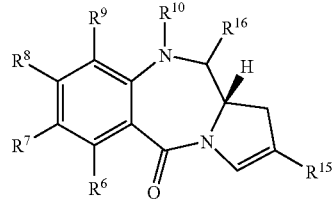

III and salts and solvates thereof, wherein:
R$^6$ and R$^9$ are independently selected from H, R, OH, OR, SH, SR, NH₂, NHR, NRR', nitro, Me₃Sn and halo;
R and R' are independently selected from optionally substituted C$_{1-12}$ alkyl, C$_{3-20}$ heterocyclyl and C$_{5-20}$ aryl groups;
the compound being a dimer with each monomer being of formula (III), where the R$^8$ groups of each monomer form together a dimer bridge having the formula —X—R"—X— linking the monomers, where R" is a $C_{3-12}$ alkylene group, which chain may be interrupted by one or more heteroatoms and/or aromatic rings, and each X is independently selected from O, S, or NH, and $R^7$ is selected from H, R, OH, OR, SH, SR, $NH_2$, NHR, NRR', nitro, $Me_3Sn$ and halo; or any pair of adjacent groups from $R^6$ to $R^9$ together form a group —O—$(CH_2)_p$—O—, where p is 1 or 2;

$R^{10}$ is a carbamate-based nitrogen protecting group;

$R^{16}$ is —O—$R^{11}$, where $R^{11}$ is an oxygen protecting group or H;

$R^{15}$ is an optionally substituted $C_{5-20}$ aryl group, wherein the optional substituents are independently selected from the group consisting of $C_{1-12}$ alkyl, $C_{3-12}$ cycloalkyl, $C_{3-20}$ heterocyclyl, $C_{5-20}$ aryl, halo, hydroxyl, —OR wherein R is a $C_{1-7}$ alkyl group or $C_{3-20}$ heterocyclyl group or $C_{5-10}$ aryl group, alkoxy, —CH$(OR^1)(OR^2)$ wherein $R^1$ is as defined above and $R^2$ is independently a $C_{1-7}$ alkyl group or $C_{3-20}$ heterocyclyl group or $C_{5-10}$ aryl group or $R^1$ and $R^2$ together with the two oxygen atoms to which they are attached form a heterocyclic ring having from 4 to 8 ring atoms, —CH$(OH)(OR^1)$ wherein $R^1$ is as defined above, ketal, hemiketal, oxo, thione, imino, formyl, acyl, carboxy, thiocarboxy, thiolocarboxy, —C(=NH)OH, —C(=NOH)OH, —C(=O)$OR^1$ wherein $R^1$ is as defined above, acyloxy, oxycarboyloxy, amino, amido, thioamido, acylamido, aminocarbonyloxy, ureido, guanidine, tetrazolyl, amindino, nitro, nitroso, azido, cyano, isocyano, cyanato, isocyanato, thiocyano, isothiocyano, sulfhydryl, thioether, disulfide, sulfine, sulfone, —S(=O)OH, $SO_2H$, —S(=O)$_2$OH, —$SO_3H$, sulfinate, sulfonate, sulfinyloxy, sulfonyloxy, sulfate, sulfamyl, sulfonamide, sulfamino, sulfonamino, sulfinamino, phosphino, phosphor, phosphinyl, phosphono, —P(=O)$(OR^{17})_2$ wherein $R^{17}$ is H or $C_{1-7}$ alkyl group or $C_{3-20}$ heterocyclyl group or $C_{5-20}$ aryl group, phosphonooxy, —PO(=O)$(OR^{17})_2$ wherein $R^{17}$ is as defined above, —OP(OH)$_2$, phosphate, phosphoramidite, and phosphoramidate; and wherein heteroatoms of the heterocyclyl groups and the optional heteroatoms of the alkylene groups are independently selected from the group consisting of N, S, and O.

15. A compound according to claim 14, wherein $R^{10}$ is Troc.

16. A compound according to claim 14, wherein $R^{11}$ is a silyl oxygen protecting group or THP.

17. A compound of formula I:

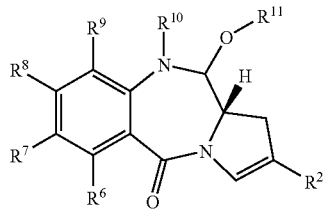

I for use in the synthesis of a compound of formula III:

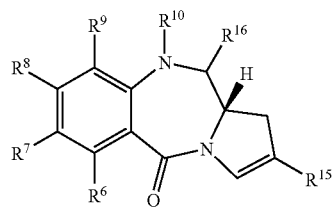

III wherein:

$R^6$ and $R^9$ are independently selected from H, R, OH, OR, SH, SR, $NH_2$, NHR, NRR', nitro, $Me_3Sn$ and halo;

R and R' are independently selected from optionally substituted $C_{1-12}$ alkyl, $C_{3-20}$ heterocyclyl and $C_{5-20}$ aryl groups;

$R^7$ is selected from H, R, OH, OR, SH, SR, $NH_2$, NHR, NRR', nitro, $Me_3Sn$ and halo, the compound of formula III being dimer with each monomer being of formula III, where the $R^8$ groups of each monomer form together a dimer bridge having the formula —X—R"—X— linking the monomers, where R" is a $C_{3-12}$ alkylene group, which chain may be interrupted by one or more heteroatoms and/or aromatic rings, and each X is independently selected from O, S, or NH;

or any pair of adjacent groups from $R^6$ to $R^9$ together form a group —O—$(CH_2)_p$—O—, where p is 1 or 2;

$R^{10}$ is a carbamate-based nitrogen protecting group, or either $R^{10}$ and $R^{16}$ together form a double bond between N10 and C11, or $R^{10}$ is H and $R^{16}$ is OH;

$R^{11}$ is an oxygen protecting group or H;

$R^2$ is a labile leaving group;

$R^{15}$ is an optionally substituted $C_{5-20}$ aryl group, wherein the optional substituents are independently selected from the group consisting of $C_{1-12}$ alkyl, $C_{3-12}$ cycloalkyl, $C_{3-20}$ heterocyclyl, $C_{5-20}$ aryl, halo, hydroxyl, —OR wherein R is a $C_{1-7}$ alkyl group or $C_{3-20}$ heterocyclyl group or $C_{5-10}$ aryl group, alkoxy, —CH$(OR^1)(OR^2)$ wherein $R^1$ is as defined above and $R^2$ is independently a $C_{1-7}$ alkyl group or $C_{3-20}$ heterocyclyl group or $C_{5-10}$ aryl group or $R^1$ and $R^2$ together with the two oxygen atoms to which they are attached form a heterocyclic ring having from 4 to 8 ring atoms, —CH$(OH)(OR^1)$ wherein $R^1$ is as defined above, ketal, hemiketal, oxo, thione, imino, formyl, acyl, carboxy, thiocarboxy, thiolocarboxy, —C(=NH)OH, —C(=NOH)OH, —C(=O)$OR^1$ wherein $R^1$ is as defined above, acyloxy, oxycarboyloxy, amino, amido, thioamido, acylamido, aminocarbonyloxy, ureido, guanidine, tetrazolyl, amindino, nitro, nitroso, azido, cyano, isocyano, cyanato, isocyanato, thiocyano, isothiocyano, sulfhydryl, thioether, disulfide, sulfine, sulfone, —S(=O)OH, $SO_2H$, —S(=O)$_2$OH, —$SO_3H$, sulfinate, sulfonate, sulfinyloxy, sulfonyloxy, sulfate, sulfamyl, sulfonamide, sulfamino, sulfonamino, sulfinamino, phosphino, phosphor, phosphinyl, phosphono, —P(=O)$(OR^{17})_2$ wherein $R^{17}$ is —H or $C_{1-7}$ alkyl group or $C_{3-20}$ heterocyclyl group or $C_{5-20}$ aryl group, phosphonooxy, —PO(=O)$(OR^{17})_2$ wherein $R^{17}$ is as defined above, —OP(OH)$_2$, phosphate, phosphoramidite, and phosphoramidate; and wherein heteroatoms of the heterocyclyl groups and the optional heteroatoms of the alkylene groups are independently selected from the group consisting of N, S, and O.

18. A compound according to claim 6, wherein $R^7$ is OR.

19. A compound according to claim 6, wherein $R^7$ is OMe.

20. A compound according to claims 1 wherein $R^{15}$ is a $C_{5-20}$ aryl group optionally substituted with a substituent selected from the group consisting of R, OH, OR, $NH_2$, NHR, NRR', ON, C(=O)H, C(=O)OH and halo.

21. A compound according to claim 1, wherein $R^{15}$ is a $C_{5-20}$ aryl group substituted by OR.

22. A compound according to claim 1, wherein $R^{15}$ is a $C_{5-20}$ aryl group substituted by OMe.

23. A compound according to claim 1, wherein $R^6$ is H, $R^7$ is OMe, X is O, R" is $(CH_2)_3$, $R^9$ is H, $R^{10}$ and $R^{16}$ together form a double bond between N10 and C11, and $R^{15}$ is para-methoxyphenyl.

24. The compound of claim 1, wherein R" is a $C_{3-12}$alkylene group interrupted by one or more heteroatoms, wherein the one or more heteroatoms are independently selected from the group consisting of O, S, and N.

25. A compound of the following formula:
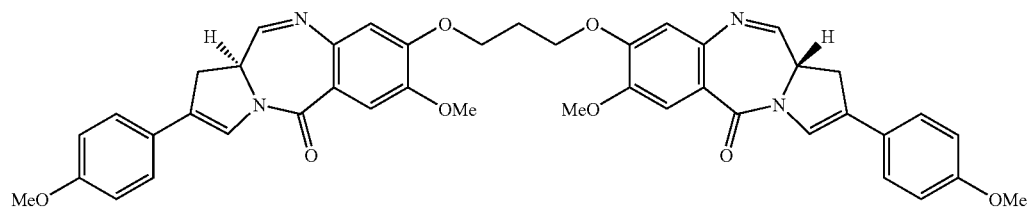
or a pharmaceutically acceptable salt thereof.
26. The compound of claim 1, wherein R and R' are unsubstituted.
27. The compound of claim 1, wherein $R^{15}$ is an unsubstituted $C_{5-20}$ aryl group.
28. The compound of claim 1, wherein $R^{15}$ is a singly substituted $C_{5-20}$ aryl group.
* * * * *